(12) United States Patent
Song et al.

(10) Patent No.: US 11,479,596 B2
(45) Date of Patent: Oct. 25, 2022

(54) FUSION PROTEIN COMPRISING THYROTROPIN RECEPTOR VARIANTS AND USE THEREOF

(71) Applicants: YUHAN CORPORATION, Seoul (KR); INDUSTRY-ACADEMIC COOPERATION FOUNDATION, YONSEI UNIVERSITY, Seoul (KR)

(72) Inventors: Moo Young Song, Gyeonggi-do (KR); Taejin Yoon, Gyeonggi-do (KR); Jung-Sun Lee, Seoul (KR); Byung Hyun Choi, Gyeonggi-do (KR); In Hwan Lim, Gyeonggi-do (KR); Man Sil Park, Gyeonggi-do (KR); Jin-Hyoung Lee, Gyeonggi-do (KR); Hyoung Sig Seo, Gyeonggi-do (KR); Hyeon Woo Kang, Gyeonggi-do (KR); Sung Ho Kim, Seoul (KR); Eun Jig Lee, Seoul (KR); Jin Sook Yoon, Seoul (KR); Cheol Ryong Ku, Seoul (KR)

(73) Assignees: YUHAN CORPORATION, Seoul (KR); INDUSTRY-ACADEMIC COOPERATION FOUNDATION, YONSEI UNIVERSITY, Seoul (KR)

( * ) Notice: Subject to any disclaimer, the term of this patent is extended or adjusted under 35 U.S.C. 154(b) by 0 days.

(21) Appl. No.: 17/256,296

(22) PCT Filed: Jul. 24, 2019

(86) PCT No.: PCT/KR2019/009177
§ 371 (c)(1),
(2) Date: Dec. 28, 2020

(87) PCT Pub. No.: WO2020/022776
PCT Pub. Date: Jan. 30, 2020

(65) Prior Publication Data
US 2021/0221869 A1 Jul. 22, 2021

(30) Foreign Application Priority Data
Jul. 25, 2018 (KR) .................. 10-2018-0086437

(51) Int. Cl.
*A61K 38/17* (2006.01)
*A61K 47/68* (2017.01)
(Continued)

(52) U.S. Cl.
CPC .......... *C07K 14/72* (2013.01); *A61K 38/1796* (2013.01); *A61K 47/64* (2017.08);
(Continued)

(58) Field of Classification Search
CPC A61K 38/1796; A61K 47/64; A61K 47/6811; C07K 14/72; C07K 2319/30
See application file for complete search history.

(56) References Cited

U.S. PATENT DOCUMENTS 7,297,482 B2 * 11/2007 Anderson .............. C12N 15/62
435/6.12
8,722,618 B2 * 5/2014 Jacobs ................... A61P 11/06
435/235.1
(Continued)

FOREIGN PATENT DOCUMENTS

KR 100897938 B1 5/2009
WO 2000005345 A1 2/2000
(Continued)

OTHER PUBLICATIONS

Bartalena, L., "Diagnosis and management of Graves disease: a global overview", "Nat Rev Endocrinol", Dec. 2013, pp. 724-734, vol. 9, Publisher: Macmillan Publishers Limited.
(Continued)

*Primary Examiner* — Jeffrey E. Russel
(74) *Attorney, Agent, or Firm* — Hultquist, PLLC; Steven J. Hultquist

(57) ABSTRACT

Disclosed are a fusion protein comprising a thyrotropin receptor (TSHR) fragment and the use thereof. More specifically, disclosed are a fusion protein comprising a TSHR fragment comprising an extracellular domain of a wild-type TSHR and having a substitution of an amino acid at specific position and an immunoglobulin Fc region or a carboxy-terminal cap (C-CAP), and the use thereof. The fusion
(Continued)

protein has improved pharmaceutical efficacy, in-vivo persistence and protein stability and a pharmaceutical composition containing the fusion protein as an active ingredient is useful as a therapeutic agent or diagnostic reagent for the alleviation of Graves' disease and Graves' ophthalmopathy.

9 Claims, 8 Drawing Sheets

Specification includes a Sequence Listing.

(51) Int. Cl.
    *C07K 14/72*     (2006.01)
    *C07K 19/00*     (2006.01)
    *A61K 47/64*     (2017.01)
    *A61K 38/00*     (2006.01)

(52) U.S. Cl.
    CPC .......... *A61K 47/6811* (2017.08); *A61K 38/00* (2013.01); *C07K 2319/30* (2013.01)

(56) References Cited

U.S. PATENT DOCUMENTS

| | | | |
|---|---|---|---|
| 2009/0170163 A1* | 7/2009 | Shen | C07K 14/001 435/69.51 |
| 2016/0115239 A1* | 4/2016 | Morrison | A61P 35/00 424/85.4 |

FOREIGN PATENT DOCUMENTS

| | | | |
|---|---|---|---|
| WO | 2006016121 A1 | 2/2006 | |
| WO | 2015189543 A2 | 12/2015 | |
| WO | WO-2018158310 A1 * | 9/2018 | ............ A61P 5/06 |

OTHER PUBLICATIONS

Chazenbalk, G., et al., "Engineering the Human Thyrotropin Receptor Ectodomain from a Non-secreted Form to a Secreted, Highly Immunoreactive Glycoprotein That Neutralizes Autoantibodies in Graves' Patients' Sera", "The Journal of Biological Chemistry", Jul. 25, 1997, pp. 18959-18965, vol. 272, No. 30.

Cundiff, J., et al., "Studies Using Recombinant Fragments of Human TSH Receptor Reveal Apparent Diversity in the Binding Specifications of Antibodies That Block TSH Binding to Its Receptor or Stimullate Thyroid Hormone Production", "The Journal of Clinical Endocrinology & Metabolism", 2001, pp. 4254-4260, vol. 86, No. 9.

Mihaesco, C., et al., "Papain Digestion Fragments of Human IgM Globulins", "Journal of Experimental Medicine", 1968, pp. 431-453, vol. 127.

NCBI, "GenBank accession; thyroid stimulatory hormone receptor [*Homo sapiens*]", "NCBI", Jan. 14, 1995, pp. No. AAA61236.1.

Tan, L., et al., "Influence of the hinge region on complement activation, C1q binding, and segmental flexibility in chimeric human immunoglobulins", "Proc. Natl. AdaD. Sci. USA", Jan. 1990, pp. 162-166, vol. 87, No. 1.

Weetman, A., "Grave's Disease", "The New England Journal of Medicine", Oct. 26, 2000, pp. 1236-1248, vol. 343.

\* cited by examiner

[Fig. 1]
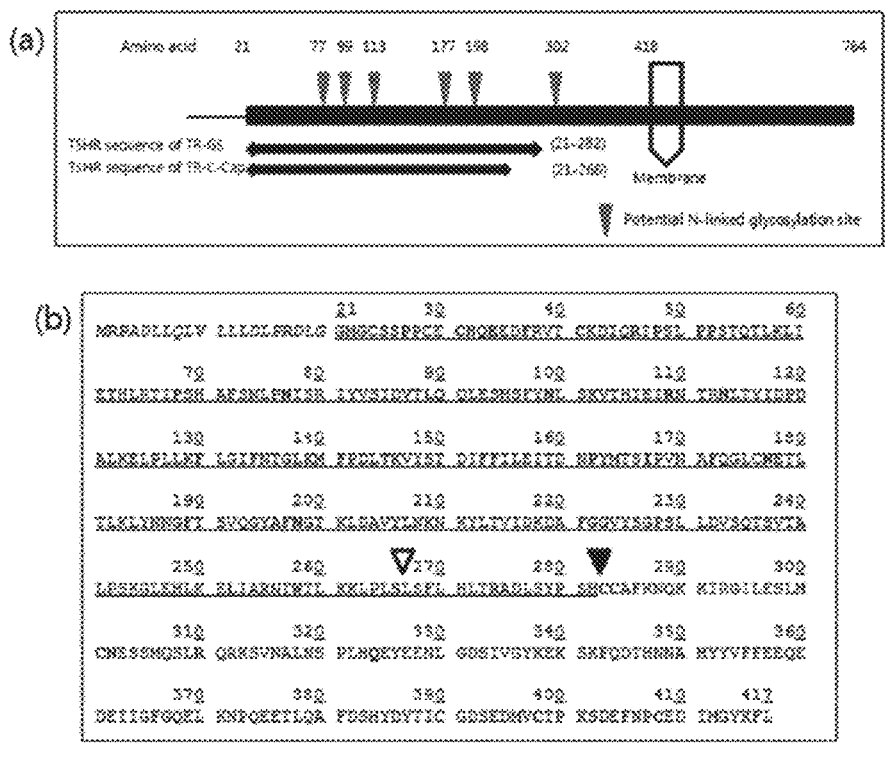
SEQ ID NO: 1
[Fig. 2]
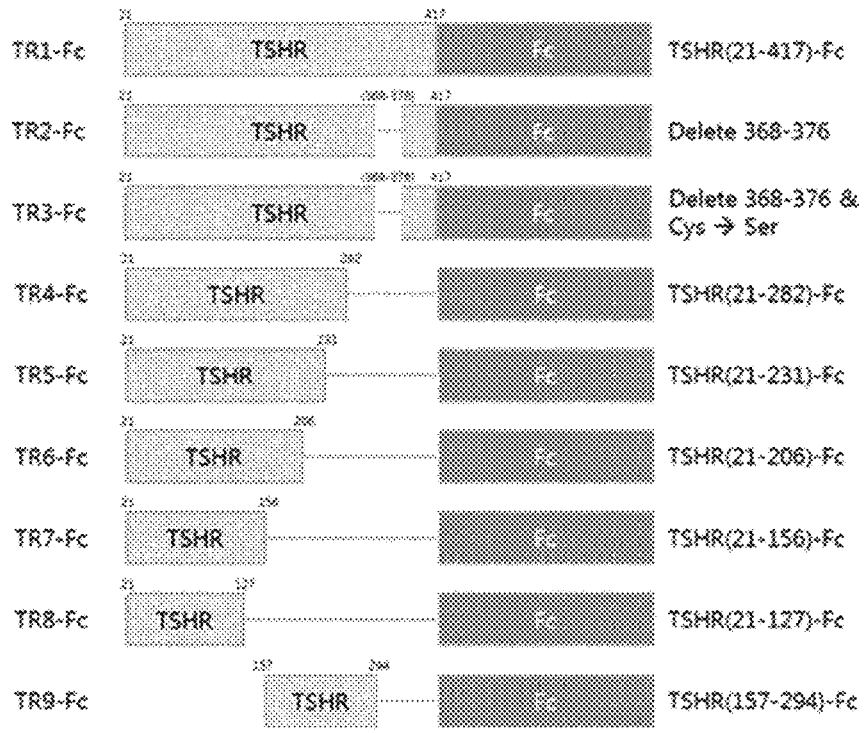

[Fig. 3]

| Candidate group | Production amount (mg/L) | TSH binding | M22 binding ability (IC50: µg/ml) | M22 neutralization cell assay (IC50: µg/ml) |
|---|---|---|---|---|
| TR1-Fc | 1.6 | ++ | >500 | >100 |
| TR3-Fc | 1 | - | 423 | 56 |
| TR4-Fc | 5.1 | - | 5.6 | 20 |
| TR8-Fc | 17 | - | NB | NT |
| TR9-Fc | 11 | - | NB | NT |

[Fig. 4]

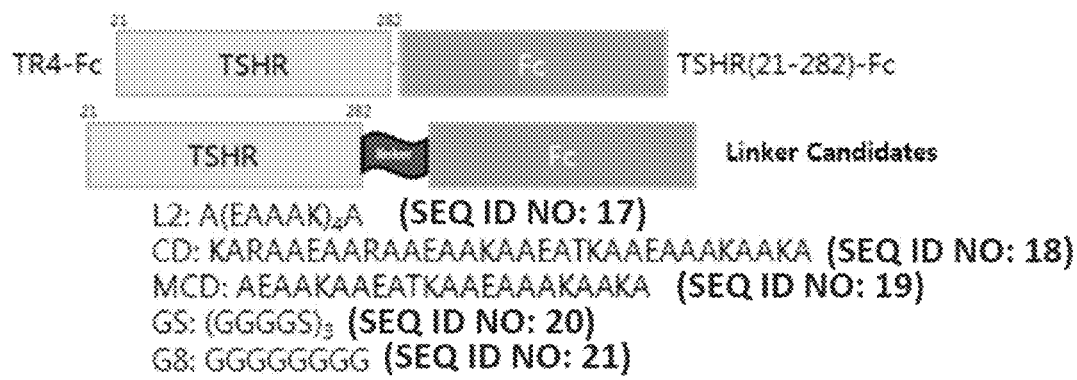

L2: A(EAAAK)₄A (SEQ ID NO: 17)
CD: KARAAEAARAAEAAKAAEATKAAEAAAKAAKA (SEQ ID NO: 18)
MCD: AEAAKAAEATKAAEAAAKAAKA (SEQ ID NO: 19)
GS: (GGGGS)₃ (SEQ ID NO: 20)
G8: GGGGGGGG (SEQ ID NO: 21)

[Fig. 5]

| Candidate group | Production amount (mg/L) | TSH binding | M22 binding ability (IC50: µg/ml) | M22 neutralization cell assay (IC50: µg/ml) |
|---|---|---|---|---|
| TR4-Fc | 5.1 | - | 5.6 | 20 |
| TR-L2 | 16 | - | 1.3 | 4.9 |
| TR-CD | 32 | - | 0.6 | 5~11 |
| TR-MCD | 17 | - | 1.3 | 6~10 |
| TR-GS | 28 | - | 0.6 | 3~6 |
| TR-G8 | 16 | - | 12 | 38 |

[Fig. 6]
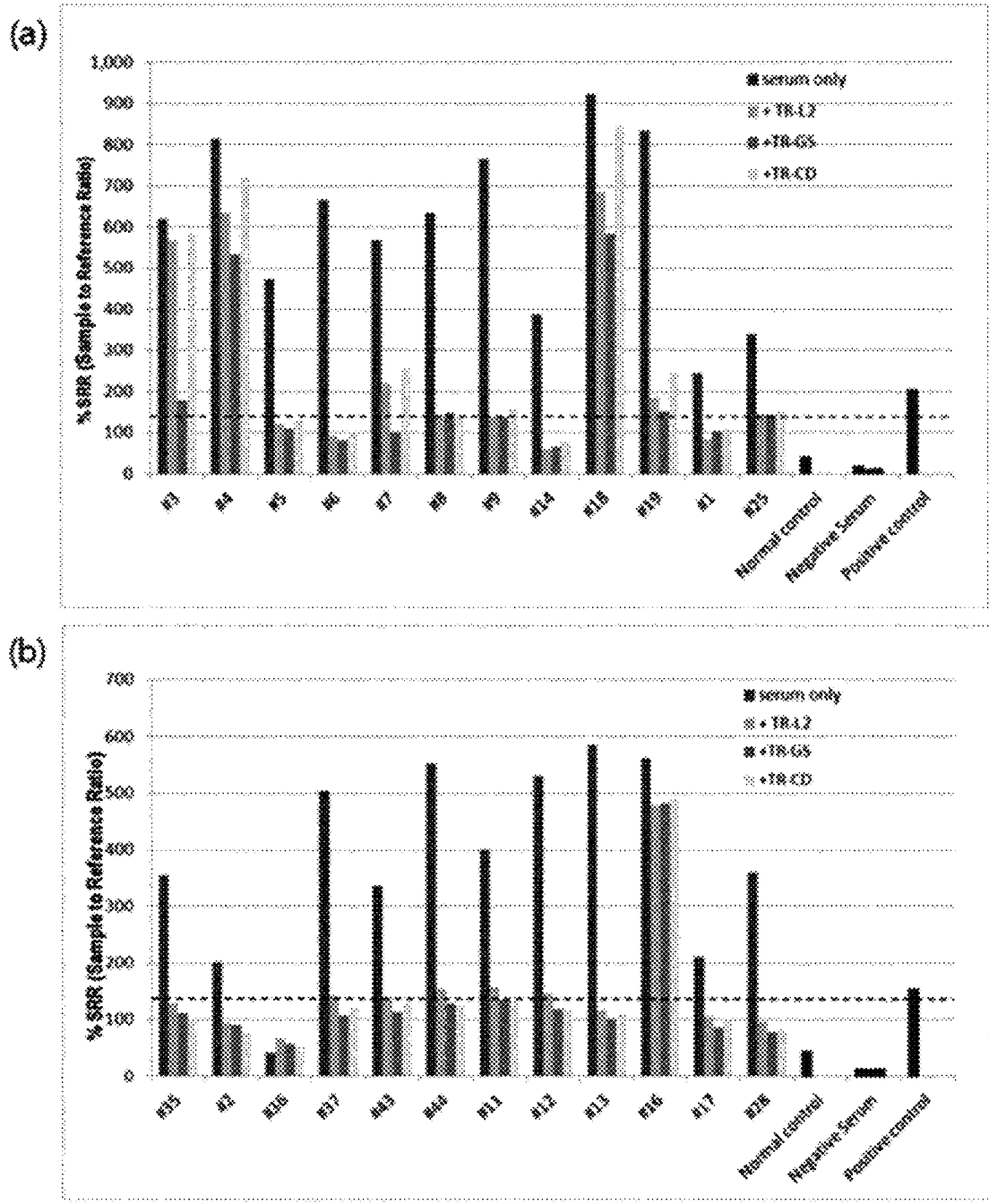

[Fig. 7]
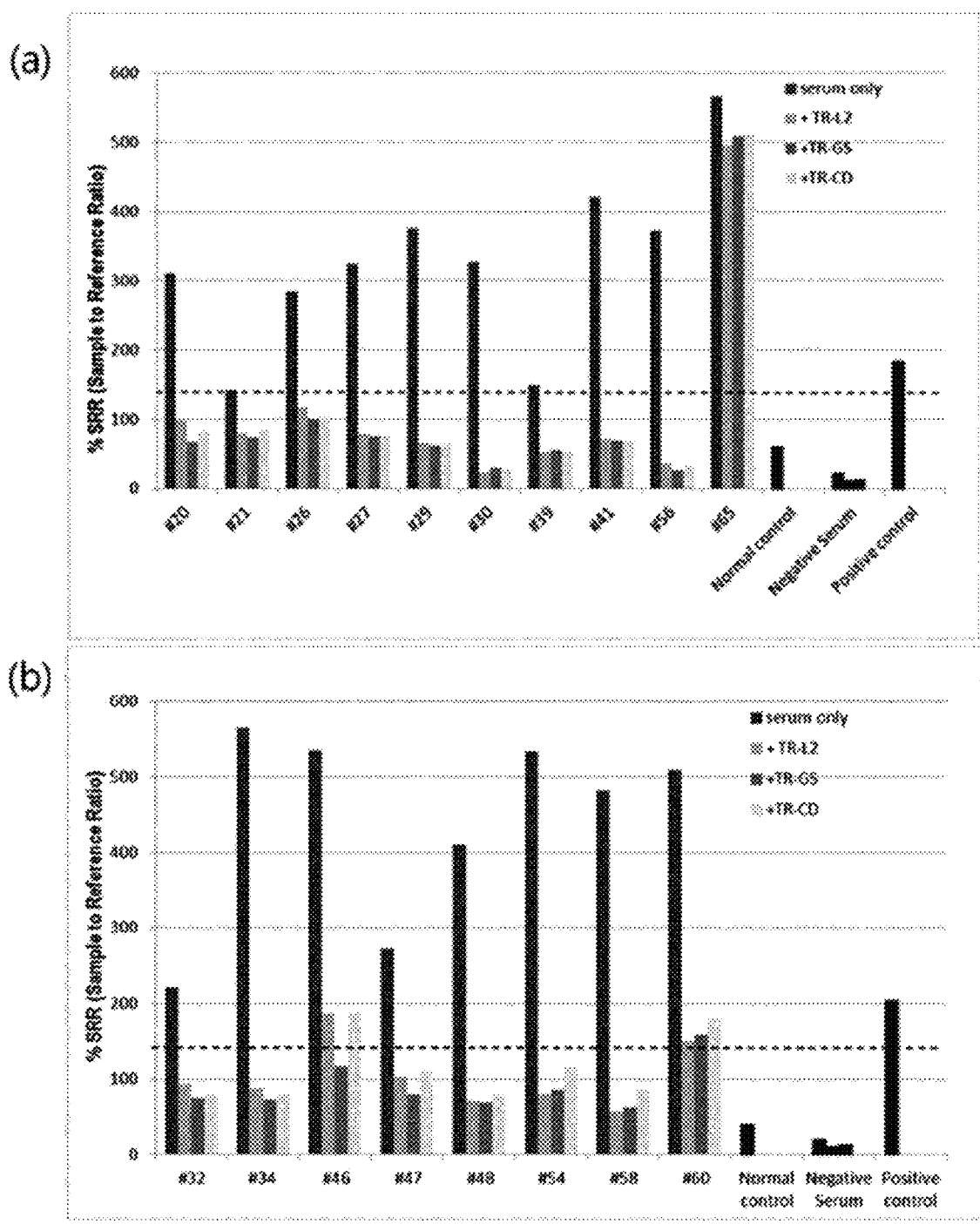

[Fig. 8]
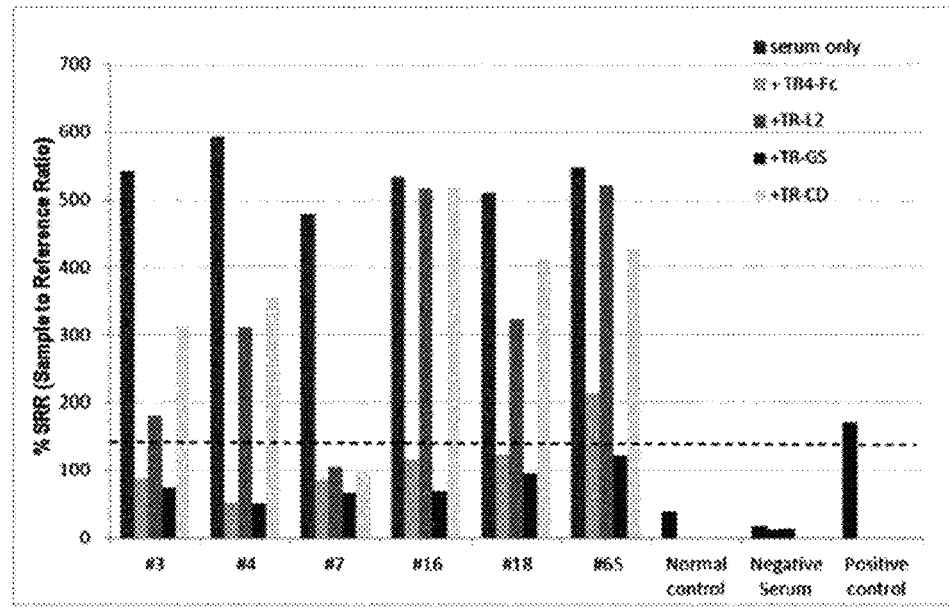
[Fig. 9]
| Candidate group | All blood samples (n=42) | | Blood samples un-reacted at 5 ug/mL (n=6) | |
|---|---|---|---|---|
| | 2.5 µg/mL | 5 µg/mL | 10 µg/mL | 20 µg/mL |
| TR4-Fc | 19/34 (56%) | - | 5/6 (83%) | 6/6 (100%) |
| TR-L2 | 19/34 (56%) | 28/42 (67%) | 1/6 (17%) | 6/6 (100%) |
| TR-GS | 25/34 (74%) | 34/42 (81%) | 6/6 (100%) | 6/6 (100%) |
| TR-CD | 18/34 (53%) | 31/42 (74%) | 1/6 (17%) | 6/6 (100%) |
[Fig. 10]
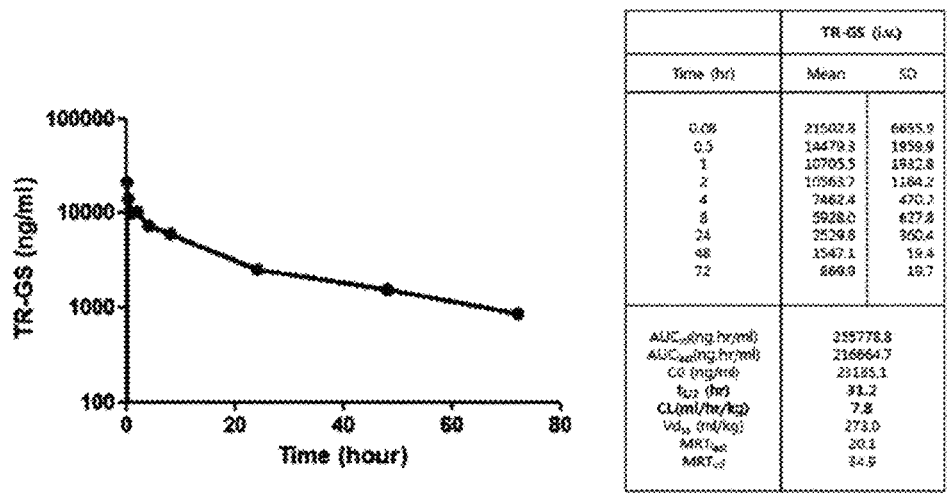

[Fig. 11]
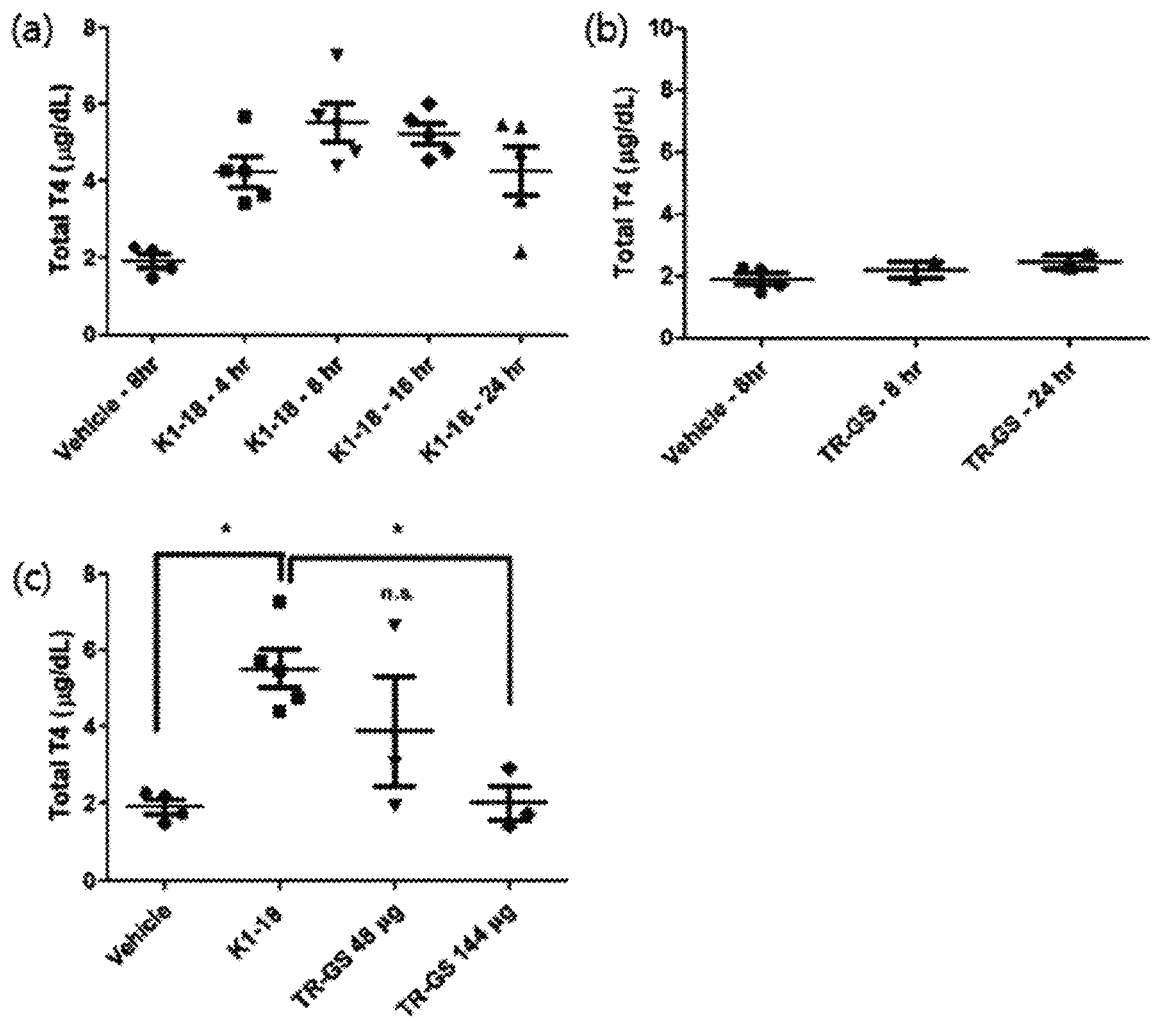
[Fig. 12]
| Candidates | C-Cap Sequences | Reactivity |
|---|---|---|
| #1 | YRENVFKLLPQLTYLDGYDRDDKE (SEQ ID NO: 23) | + |
| #2 | DRENVFKLLPQLTYLYGYDRDDKE (SEQ ID NO: 24) | + |
| #3 | YRENSFKLLPQLTYLDGYDRDDKE (SEQ ID NO: 25) | +++ |
| #4 | YRESVFKLLPQLTYLDGYDRDDKE (SEQ ID NO: 26) | + |
| #5 | YRENSFKLLPQLTYLEGYDRDDKE (SEQ ID NO: 27) | +++ |
| #6 | YRESVFKLLPQLTYLEGYDRDDKE (SEQ ID NO: 28) | + |

[Fig. 13]
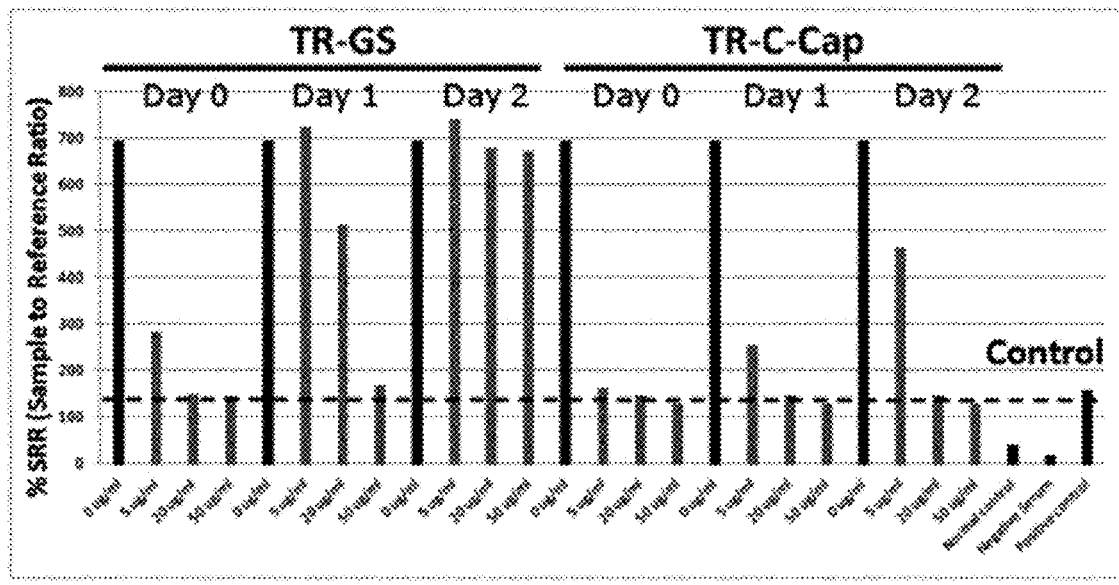
[Fig. 14]
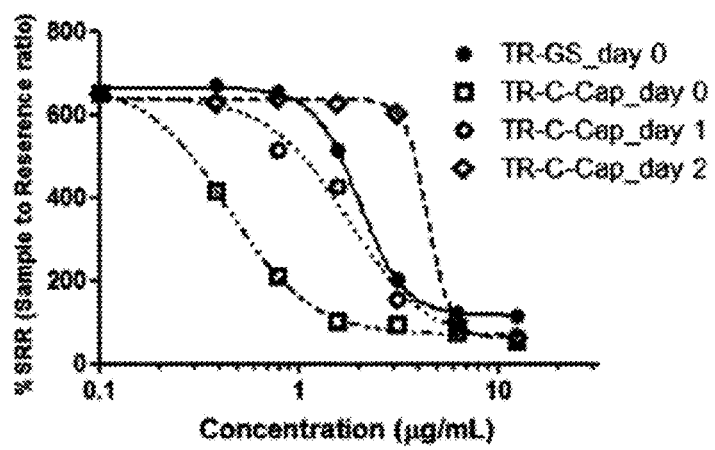
| | TR-GS_day 0 | TR-C-Cap_day 0 | TR-C-Cap_day 1 | TR-C-Cap_day2 |
|---|---|---|---|---|
| IC50 (µg/mL) | 2.015 | 0.4439 | 1.782 | 4.469 |
| $R^2$ | 0.9993 | 0.9986 | 0.9877 | 0.9991 |

[Fig. 15]
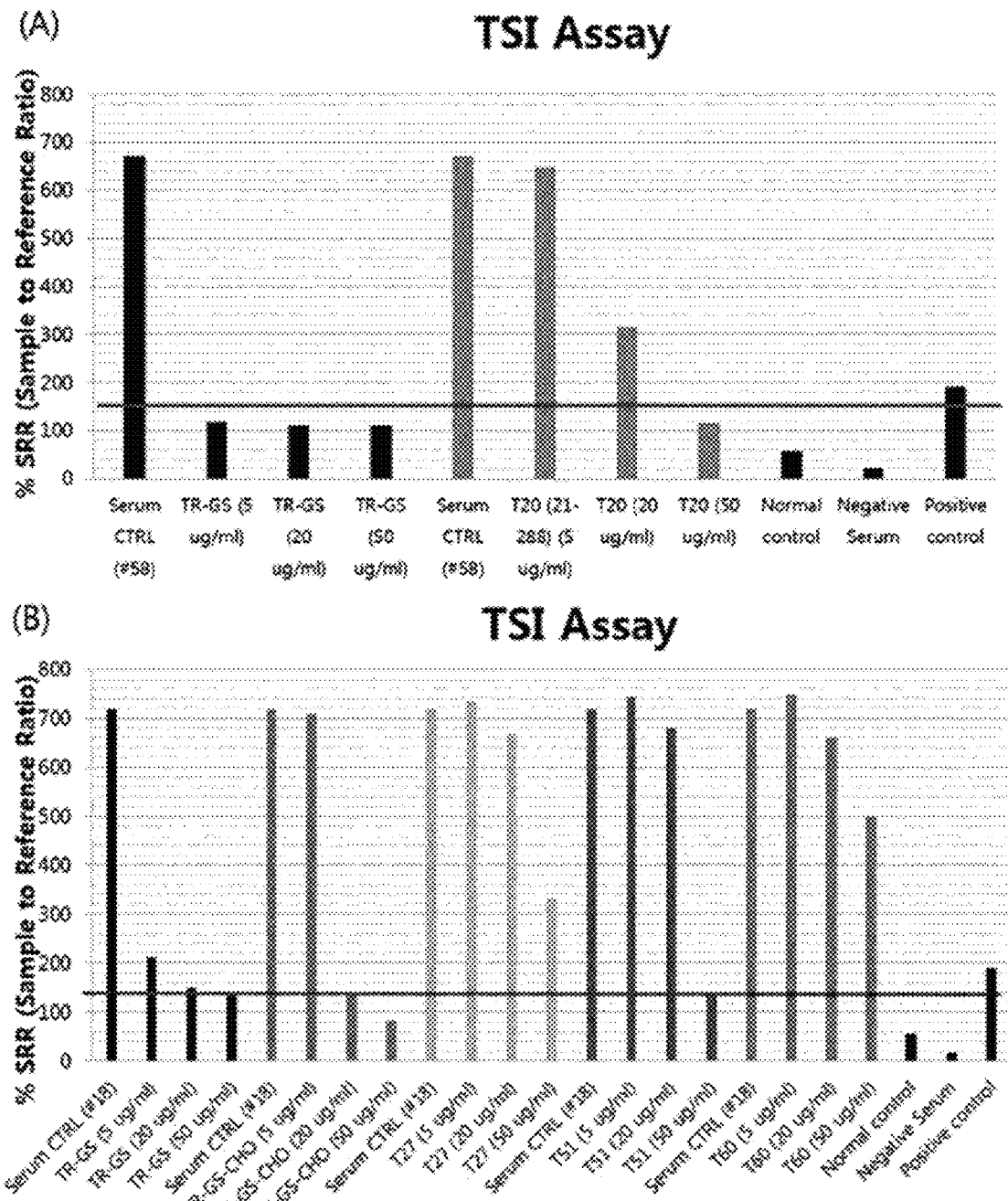

FUSION PROTEIN COMPRISING THYROTROPIN RECEPTOR VARIANTS AND USE THEREOF

CROSS-REFERENCE TO RELATED APPLICATIONS

This application is a U.S. national phase under the provisions of 35 U.S.C. § 371 of International Patent Application No. PCT/KR2019/009177 filed Jul. 24, 2019, which in turn claims priority under 35 U.S.C. § 119 of Korean Patent Application No. 10-2018-0086437 filed Jul. 25, 2018. The disclosure of such international patent application is hereby incorporated herein by reference in its entirety, for all purposes.

REFERENCE TO SEQUENCE LISTING SUBMITTED VIA EFS-WEB

This application includes an electronically submitted sequence listing in .txt format. The .txt file contains a sequence listing entitled "546_SeqListing_ST25.txt" created on Dec. 28, 2020 and is 83,058 bytes in size. The sequence listing contained in this .txt file is part of the specification and is hereby incorporated by reference herein in its entirety.

FIELD OF THE INVENTION

The present invention relates to a fusion protein comprising a thyrotropin receptor (TSHR) fragment having improved in-vivo persistence, protein stability and pharmacological activity, and the use thereof. More specifically, the present invention relates to a fusion protein comprising a TSHR fragment comprising an extracellular domain of a wild-type TSHR, and an immunoglobulin Fc region or a carboxy-terminal cap (C-CAP) and the use thereof for the treatment or prevention of Graves' disease.

BACKGROUND OF THE INVENTION

The production of normal thyroid hormone is regulated by thyroid-stimulating hormone. The thyroid-stimulating hormone secreted from the hypothalamus binds to the thyroid-stimulating hormone receptor in the thyroid tissue cells and thereby synthesizes thyroid hormone through a series of signaling processes with G proteins in the thyroid cells. The synthesized hormone conducts the functions thereof while circulating throughout the body. However, when excessive hormone is produced, the expression of thyroid-stimulating hormone in the hypothalamus is suppressed, thus resulting in inhibition of synthesis of thyroid hormone.

Meanwhile, Graves' disease results from fundamental defects in the immune system and is caused by autoantibodies that bind to the thyrotropin receptor (TSHR). In most cases, autoantibodies specific to thyrotropin receptors (TSHRs) bind to the thyrotropin receptors, resulting in hyperthyroidism. In addition, in some cases, autoantibodies bind to thyrotropin receptors, resulting in hypothyroidism which suppresses the effects of the binding of thyroid hormone (TSH). Graves' disease is an autoimmune disease caused by autoantibodies that induce over-production of thyroid hormone, that is, hyperthyroidism (Weetman A P, N Engl. J Med 2000; 343; 1236-1248, Bartalena L, Nat Rev Endocrinol 2013; 9; 724-734).

Generally, methods such as the use of non-selective thyroid function inhibitors or the removal of thyroid tissue through radioactive isotopes or surgical operation have been used for the treatment of Graves' disease. However, the use of thyroid function inhibitors entails a high risk of recurrence, and the removal of thyroid tissue may have a problem in that body homeostasis should be maintained because continuous administration of thyroid hormone is required. Graves ophthalmopathy has been reported to develop in 50% of patients with Graves' disease. The main cause of Graves' ophthalmopathy has not been elucidated. However, since the thyrotropin receptor (TSHR) was reported to be expressed in the orbital fibroblasts of patients with Graves' ophthalmopathy, autoantibodies specific to the thyrotropin receptor are known to play an important role in ophthalmopathy.

Thus, it is considered that symptoms of Graves' disease can be reduced by inhibiting the binding of autoantibodies to the thyrotropin receptor, which is the cause of Graves' disease. Nevertheless, no method of selectively inhibiting the binding of these autoantibodies to the receptor has been developed. Considering the diversity of autoantibodies to thyrotropin receptor, fusion proteins using the thyrotropin receptor itself are considered to be the best possible selective binding substances. The expression of the available structure of the thyrotropin receptor was compared by sequentially cutting the end of the ectodomain of the thyrotropin receptor in 1997 (Chazenbalk G D et al. J Biol Chem (1997) 272(30); 18959-65). Among TSHR-261, TSHR-289 and TSHR-309, the smallest one, TSHR-261, showed the best ability to bind to autoantibodies of the blood of Graves' disease patients and then neutralize the same. However, the patent by the same authors (WO 2000005345 A1) shows that TSHR-261 is relatively less stable compared to large-sized substances such as TSH1R-289 and TSHR-309. For this reason, the recent patent (WO 2015189543 A2) discloses the introduction of various point mutations in order to enhance thermostability of TSHR-260 and thereby improve the half-life at the same temperature. However, the half-life failed to reach the level at which the blood half-life is satisfactory for use as a therapeutic agent.

No previous research has made on fusion proteins for the supplementation of the additional functions other than the expression of ectodomain fragments of TSHR substances. In particular, it is critical to increase the blood half-life in order to inhibit the selective binding of autoantibodies associated with the development of therapeutic drugs, but no research on fusion proteins for this purpose has been reported to date. Also, no studies on fusion proteins aimed at improving the poor thermostability of TSHR-261 have been reported. In the patent for prior studies using thyrotropin receptors (WO 2000005345A1), there has not been reported any case where a new function is added by fusing the protein sequence of the thyrotropin receptor with different protein sequences.

As a result of intensive efforts to improve the in-vivo half-life and thermostability of TSHR, the present inventors have found that, when the Fc of immunoglobulin IgG is bound to the thyrotropin receptor fragment, or the protein called "C-Cap" is bound to the C-terminal of the thyrotropin receptor fragment, the blood half-life is increased or thermostability at 37° C. of the thyrotropin receptor is enhanced, and binding of the thyrotropin autoantibodies to the thyrotropin receptor is inhibited without affecting the production of thyroid hormone by the thyroid-stimulating hormone. Based on this finding, the present invention has been completed.

SUMMARY OF THE INVENTION

Therefore, it is one object of the present invention to provide a fusion protein comprising a TSHR fragment containing a portion of an extracellular domain in a wild-type TSHR and an immunoglobulin Fc region or a carboxy-terminal cap (C-Cap).

It is another object of the present invention to provide a nucleic acid encoding the fusion protein, a recombinant vector comprising the nucleic acid, and a recombinant cell introduced with the vector.

It is another object of the present invention to provide a method for producing the fusion protein.

It is yet another object of the present invention to provide a pharmaceutical composition containing the fusion protein for treating or preventing Graves' disease.

In accordance with one aspect of the present invention, provided is a fusion protein comprising an immunoglobulin Fc region or a carboxy-terminal cap (C-CAP) bound to the following TSHR fragment: (i) a fragment from the amino acid at position 21 to the amino acid at position 282 of a TSHR represented by an amino acid sequence of SEQ ID NO: 1; or (ii) a fragment from the amino acid at position 21 to the amino acid at position 266 of the TSHR represented by the amino acid sequence of SEQ ID NO: 1.

In accordance with another aspect of the present invention, provided is a nucleic acid encoding the fusion protein and a recombinant vector comprising the nucleic acid.

In accordance with another aspect of the present invention, provided are a recombinant cell introduced with the recombinant vector and a method of producing the fusion protein using the recombinant cell.

In accordance with another aspect of the present invention, provided is a pharmaceutical composition for treating or preventing Graves' disease comprising the fusion protein.

In accordance with another aspect of the present invention, provided is a pharmaceutical composition comprising the fusion protein for use in a method of treating or preventing Graves' disease.

In accordance with another aspect of the present invention, provided is a method for treating or preventing Graves' disease by administering a pharmaceutical composition comprising the fusion protein.

In accordance with another aspect of the present invention, provided is composition for diagnosing Graves' disease comprising the fusion protein.

In accordance with another aspect of the present invention, provided is a method for diagnosing Graves' disease by using a composition comprising the fusion protein.

BRIEF DESCRIPTION OF THE DRAWINGS

FIG. 1 in (a) shows a schematic diagram illustrating the amino acid sequence of the human thyrotropin receptor, and in (b) shows the ectodomain amino acid sequence of the human thyrotropin receptor;

FIG. 2 is a schematic diagram illustrating fusion proteins of immunoglobulin Fc using the ectodomain amino acid sequence of the human thyrotropin receptor, wherein the cysteine amino acid is substituted with serine at positions 391, 398 and 408 in TR3-Fc;

FIG. 3 shows the results of measurement of production amounts of Fc fusion proteins of various thyrotropin receptors in HEK293 cells, binding of expressed fusion proteins to thyroid-stimulating hormone and binding ability thereof to the thyrotropin receptor autoantibodies (M22);

FIG. 4 is a schematic diagram illustrating fusion proteins inserted with linkers based on the TR4-Fc fusion protein and the amino acid sequences of the used linkers;

FIG. 5 shows the results of evaluation of the production amounts of TR4-Fc fusion proteins for respective linkers, the binding ability thereof to thyroid hormone, the binding ability thereof to autoantibodies and the autoantibody-neutralizing ability thereof;

FIG. 6 in (a) and (b) shows the results of determination of the autoantibody-neutralizing effect of 5 μg/ml of a linker-inserted fusion protein in the blood of a patient with Graves' disease, wherein the measurement is carried out using a Thyretain TSI assay kit and % SRR less than 140 is considered to be negative;

FIG. 7 in (a) and (b) shows the results of determination of the autoantibody-neutralizing effect of 5 μg/ml of a linker-inserted fusion protein in the blood of a patient with Graves' disease, wherein the measurement is carried out using a Thyretain TSI assay kit and % SRR less than 140 is considered to be negative;

FIG. 8 shows the results of determination of the reactivity to six patient blood samples which did not decrease to negative at 5 μg/mL using 10 μg/mL of fusion proteins;

FIG. 9 shows the summary of evaluation of the neutralization efficacy of patient blood samples wherein only TR-GS exhibits neutralization efficacy in all the blood samples at the concentration of 10 μg/mL, and all the fusion proteins exhibit neutralization efficacy in 42 blood samples at a concentration of 20 μg/mL, and 6 blood samples #3, #4, #7, #16, #18 and #65 which were not found to be neutralized at 5 μg/mL were found to contain a large amount of autoantibodies therein;

FIG. 10 shows the result of pharmacokinetic evaluation of TR-GS fusion proteins expressed in CHO cells;

FIG. 11 in (a) shows the result of measurement of the concentration of the total amount of T4 (thyroid hormone) as a marker in the blood after intravenous administration of 0.3 mg/Kg of K1-18 (thyrotropin receptor autoantibody) to C57BL/6 mice to find the change in thyroid-stimulating hormone due to the thyrotropin receptor autoantibody, in (b) shows the result of determination of the effects on the total amount of T4 as a marker after intravenous administration of TR-GS (7.2 mg/Kg) as a fusion protein to C57BL/6 mice, and in (c) shows the result of determination of the effects on the total amount of T4 as a marker, 8 hours after administration of TR-GS (48 μg: 2.4 mg/Kg, 144 μg: 7.2 mg/Kg) as a fusion protein, and 30 minutes after peritoneal administration of 0.3 mg/Kg of K1-18 (thyrotropin receptor autoantibody) as a fusion protein to C57BL/6 mice, wherein statistical analysis is performed using the one-way ANOVA method and * means $p<0.01$;

FIG. 12 shows the reactivity associated with the autoantibody neutralization effect measured using a Thyretain TSI assay kit with regard to fusion proteins expressed with six C-cap candidate group sequences through substitution of an amino acid forming a hydrogen bond (underlined Y: tyrosine, D: glutamic acid) necessary for C-cap functions, as well as amino acid capable of inducing an additional hydrogen bond, based on the amino acid sequence (#1) derived from the C-Cap of the human pp32 sequence;

FIG. 13 shows the result of comparison of thermostability between TR-GS and TR-C-Cap fusion proteins, wherein the neutralization effects of autoantibodies using patient blood sample #18 were measured using the Thyretain TSI assay kit, the TR-GS and TR-C-Cap materials were used after storage at 37° C. for 0 (in case of a material stored at −70°), 1 and 2 days, and the results obtained using 5, 20 and 50 μg/mL of fusion proteins are shown by bar graphs;

FIG. 14 shows the results of autoantibody neutralization effects of fusion proteins at low concentrations (0.39 to 12.5 μg/mL) measured using patient blood #18 and a Thyretain TSI assay kit in order to determine accurate IC50 values of TR-GS and TR-C-Cap, respectively; and FIG. 15 in (A) shows the results of determination of the reactivity associated with the autoantibody neutralization effect of TR-GS and TSHR 21-288-Fc fusion proteins measured using the Thyretain TSI assay kit, and in (B) shows the results of determination of the reactivity associated with the autoantibody neutralization effect of TSHR 1-260-Fc, TSHR 21-262-Fc, and TSHR 21-260-Fc fusion proteins measured using the Thyretain TSI assay kit.

DETAILED DESCRIPTION OF THE EMBODIMENTS

Unless defined otherwise, all technical and scientific terms used herein have the same meanings as appreciated by those skilled in the field to which the present invention pertains. In general, the nomenclature used herein is well-known in the art and is ordinarily used.

Among general various long-acting technologies for increasing the half-life of proteins, Fc fusion technology is most widely used due to the prolonged in-vivo half-life and less concern about side effects such as toxicity or induction of immune responses. In order to develop Fc-fused TSHR fragments as drugs for long-acting therapy, the following requirements should be satisfied.

First, the decrease in in-vitro activity due to fusion should be small. In general, the activity of small proteins such as chemokines is known to greatly depend on the fusion sites and the type of linkers when fused with relatively large Fc. Thus, the activity of the TSHR fragment and Fc fusion protein may vary depending on whether or not it is fused or where the fusion occurs.

Second, when taking into consideration the fact that most biopharmaceuticals may cause immunogenicity in patients, the risk of immunogenicity by fusion linkers or mutants should be low.

Third, there should be no stability-associated problems caused by fusion position or mutation introduction.

Fourth, an undesired immune response may result in dependence on the type (isotype) of fused immunoglobulin, so an alternative thereto is needed.

The present inventors have attempted to improve the physiological activity and physical properties of TSHR in consideration of these requirements. As a result, the present inventors have found that, when using a portion of the TSHR ectodomain as a fragment, or introducing a mutation at a specific site and binding an immunoglobulin Fc region thereto, the activity of TSHR was increased, the degree of in-vivo exposure and in-vivo half-life were increased, and the pharmacological efficacy was improved.

That is, in one embodiment of the present invention, a fusion protein comprising the following thyrotropin receptor mutant and an immunoglobulin Fc region or a carboxy-terminal cap (C-Cap) is prepared:

(1) a fragment from the amino acid at position 21 to the amino acid at position 417 of a TSHR represented by an amino acid sequence of SEQ ID NO: 1; (2) a deletion of the amino acid at position 368 to the amino acid at position 376 in the fragment from the amino acid at position 21 to the amino acid at position 417 of the TSHR represented by the amino acid sequence of SEQ ID NO: 1; (3) at least one mutation selected from the group consisting of a deletion of the amino acid at position 368 to the amino acid at position 376, a substitution of cysteine at position 391 with serine, a substitution of cysteine at position 398 with serine, and a substitution of cysteine at position 408 with serine in the fragment from the amino acid at position 21 to the amino acid at position 417 of the TSHR represented by the amino acid sequence of SEQ ID NO: 1; (4) a fragment from the amino acid at position 21 to the amino acid at position 282 of the TSHR represented by the amino acid sequence of SEQ ID NO: 1; (5) a fragment from the amino acid at position 21 to the amino acid at position 266 of the TSHR represented by the amino acid sequence of SEQ ID NO: 1; (6) a fragment from the amino acid at position 21 to the amino acid at position 231 of the TSHR represented by the amino acid sequence of SEQ ID NO: 1; (7) a fragment from the amino acid at position 21 to the amino acid at position 206 of the TSHR represented by the amino acid sequence of SEQ ID NO: 1; (8) a fragment from the amino acid at position 21 to the amino acid at position 156 of the TSHR represented by the amino acid sequence of SEQ ID NO: 1; (9) a fragment from the amino acid at position 21 to the amino acid at position 127 of TSHR represented by the amino acid sequence of SEQ ID NO: 1; (10) a fragment from the amino acid at position 157 to the amino acid at position 294 of the TSHR represented by the amino acid sequence of SEQ ID NO: 1; and (11) at least one mutation selected from the group consisting of a substitution of aspartic acid at position 43 with alanine, a substitution of glutamic acid at position 61 with alanine and a substitution of lysine at position 250 with alanine in the fragment from the amino acid at position 21 to the amino acid at position 282 of the TSHR represented by the amino acid sequence of SEQ ID NO: 1.

The specific amino acid sequences of fusion proteins are shown in Table 1 below.

TABLE 1

Amino acid sequences of TSHR mutants

| SEQ ID NO | Name | Amino acid sequence |
|---|---|---|
| 2 | TSHR 21-417 | GMGCSSPPCECHQEEDFRVTCKDIQRIPSLPPSTQTLKLI ETHLRTIPSHAFSNLPNISRIYVSIDVTLQQLESHSFYNLS KVTHIEIRNTRNLTYIDPDALKELPLLKFLGIFNTGLKMF PDLTKVYSTDIFFILEITDNPYMTSIPVNAFQGLCNETLT LKLYNNGFTSVQGYAFNGTKLDAVYLNKNKYLTVIDK DAFGGVYSGPSLLDVSQTSVTALPSKGLEHLKELIARN TWTLKKLPLSLSFLHLTRADLSYPSHCCAFKNQKKIRGI LESLMCNESSMQSLRQRKSVNALNSPLHQEYEENLGDS IVGYKEKSKFQDTHNNAHYYVFFEEQEDEIIGFGQELK NPQEETLQAFDSHYDYTICGDSEDMVCTPKSDEFNPCE DIMGYKFL |

TABLE 1 -continued

Amino acid sequences of TSHR mutants

| SEQ ID NO | Name | Amino acid sequence |
|---|---|---|
| 3 | TSHR 21-417 Δ368-376 | GMGCSSPPCECHQEEDFRVTCKDIQRIPSLPPSTQTLKLI ETHLRTIPSHAFSNLPNISRIYVSIDVTLQQLESHSFYNLS KVTHIEIRNTRNLTYIDPDALKELPLLKFLGIFNTGLKMF PDLTKVYSTDIFFILEITDNPYMTSIPVNAFQGLCNETLT LKLYNNGFTSVQGYAFNGTKLDAVYLNKNKYLTVIDK DAFGGVYSGPSLLDVSQTSVTALPSKGLEHLKELIARN TWTLKKLPLSLSFLHLTRADLSYPSHCCAFKNQKKIRGI LESLMCNESSMQSLRQRKSVNALNSPLHQEYEENLGDS IVGYKEKSKFQDTHNNAHYYVFFEEQEDEIIGFGTLQAF DSHYDYTICGDSEDMVCTPKSDEFNPCEDIMGYKFL |
| 4 | TSHR 21-417 Δ368 376-C391S/C398S/C408S | GMGCSSPPCECHQEEDFRVTCKDIQRIPSLPPSTQTLKLI ETHLRTIPSHAFSNLPNISRIYVSIDVTLQQLESHSFYNLS KVTHIEIRNTRNLTYIDPDALKELPLLKFLGIFNTGLKMF PDLTKVYSTDIFFILEITDNPYMTSIPVNAFQGLCNETLT LKLYNNGFTSVQGYAFNGTKLDAVYLNKNKYLTVIDK DAFGGVYSGPSLLDVSQTSVTALPSKGLEHLKELIARN TWTLKKLPLSLSFLHLTRADLSYPSHCCAFKNQKKIRGI LESLMCNESSMQSLRQRKSVNALNSPLHQEYEENLGDS IVGYKEKSKFQDTHNNAHYYVFFEEQEDEIIGFGTLQAF DSHYDYTISGDSEDMVSTPKSDEFNPSEDIMGYKFL |
| 5 | TSHR 21-282 | GMGCSSPPCECHQEEDFRVTCKDIQRIPSLPPSTQTLKLI ETHLRTIPSHAFSNLPNISRIYVSIDVTLQQLESHSFYNLS KVTHIEIRNTRNLTYIDPDALKELPLLKFLGIFNTGLKMP DLTKVYSTDIFFILEITDNPYMTSIPVNAFQGLCNETLTL KLYNNGFTSVQGYAFNGTKLDAVYLNKNKYLTVIDKD AFGGVYSGPSLLDVSQTSVTALPSKGLEHLKELIARNT WTLKKLPLSLSFLHLTRADLSYP SH |
| 6 | TSHR 21-266 | GMGCSSPPCECHQEEDFRVTCKDIQRIPSLPPSTQTLKLI ETHLRTIPSHAFSNLPNISRIYVSIDVTLQQLESHSFYNLS KVTHIEIRNTRNLTYIDPDALKELPLLKFLGIFNTGLKMF PDLTKVYSTDIFFILEITDNPYMTSIPVNAFQGLCNETLT LKLYNNGFTSVQGYAFNGTKLDAVYLNKNKYLTVIDK DAFGGVYSGPSLLDVSQTSVTALPSKGLEHLKELIARN TWTLKKLPLS |
| 7 | TSHR 21-231 | GMGCSSPPCECHQEEDFRVTCKDIQRIPSLPPSTQTLKLI ETHLRTIPSHAFSNLPNISRIYVSIDVTLQQLESHSFYNLS KVTHIEIRNTRNLTYIDPDALKELPLLKFLGIFNTGLKMF PDLTKVYSTDIFFILEITDNPYMTSIPVNAFQGLCNETLT LKLYNNGFTSVQGYAFNGTKLDAVYLNKNKYLTVIDK DAFGGVYSGPSLL |
| 8 | 206 TSHR 21-206 | GMGCSSPPCECHQEEDFRVTCKDIQRIPSLPPSTQTLKLI ETHLRTIPSHAFSNLPNISRIYVSIDVTLQQLESHSFYNLS KVTHIEIRNTRNLTYIDPDALKELPLLKFLGIFNTGLKMF PDLTKVYSTDIFFILEITDNPYMTSIPVNAFQGLCNETLT LKLYNNGFTSVQGYAFNGTKLDAVY |
| 9 | TSHR 21-156 | GMGCSSPPCECHQEEDFRVTCKDIQRIPSLPPSTQTLKLI ETHLRTIPSHAFSNLPNISRIYVSIDVTLQQLESHSFYNLS KVTHIEIRNTRNLTYIDPDALKELPLLKFLGIFNTGLKMF PDLTKVYSTDIFFIL |
| 10 | TSHR 21-127 | GMGCSSPPCECHQEEDFRVTCKDIQRIPSLPPSTQTLKLI ETHLRTIPSHAFSNLPNISRIYVSIDVTLQQLESHSFYNLS KVTHIEIRNTRNLTYIDPDALKELPL |
| 11 | TSHR 157-294 | EITDNPYMTSIPVNAFQGLCNETLTLKLYNNGFTSVQG YAFNGTKLDAVYLNKNKYLTVIDKDAFGGVYSGPSLL DVSQTSVTALPSKGLEHLKELIARNTWTLKKLPLSLSFL HLTRADLSYPSHCCAFKNQKKIRG |
| 12 | TSHR 21-282 D43A | GMGCSSPPCECHQEEDFRVTCKAIQRIPSLPPSTQTLKLI ETHLRTIPSHAFSNLPNISRIYVSIDVTLQQLESHSFYNLS KVTHIEIRNTRNLTYIDPDALKELPLLKFLGIFNTGLKMP DLTKVYSTDIFFILEITDNPYMTSIPVNAFQGLCNETLTL KLYNNGFTSVQGYAFNGTKLDAVYLNKNKYLTVIDKD AFGGVYSGPSLLDVSQTSVTALPSKGLEHLKELIARNT WTLKKLPLSLSFLHLTRADLSYP SH |

TABLE 1 -continued

Amino acid sequences of TSHR mutants

| SEQ ID NO | Name | Amino acid sequence |
|---|---|---|
| 13 | TSHR 21-282 E61A | GMGCSSPPCECHQEEDFRVTCKDIQRIPSLPPSTQTLKLI ATHLRTIPSHAFSNLPNISRIYVSIDVTLQQLESHSFYNLS KVTHIEIRNTRNLTYIDPDALKELPLLKFLGIFNTGLKMP DLTKVYSTDIFFILEITDNPYMTSIPVNAFQGLCNETLTL KLYNNGFTSVQGYAFNGTKLDAVYLNKNKYLTVIDKD AFGGVYSGPSLLDVSQTSVTALPSKGLEHLKELIARNT WTLKKLPLSLSFLHLTRADLSYP SH |
| 14 | TSHR 21-282 D43A/E61A | GMGCSSPPCECHQEEDFRVTCKAIQRIPSLPPSTQTLKLI ATHLRTIPSHAFSNLPNISRIYVSIDVTLQQLESHSFYNLS KVTHIEIRNTRNLTYIDPDALKELPLLKFLGIFNTGLKMP DLTKVYSTDIFFILEITDNPYMTSIPVNAFQGLCNETLTL KLYNNGFTSVQGYAFNGTKLDAVYLNKNKYLTVIDKD AFGGVYSGPSLLDVSQTSVTALPSKGLEHLKELIARNT WTLKKLPLSLSFLHLTRADLSYP SH |
| 15 | TSHR 21-282 K250A | GMGCSSPPCECHQEEDFRVTCKDIQRIPSLPPSTQTLKLI ETHLRTIPSHAFSNLPNISRIYVSIDVTLQQLESHSFYNLS KVTHIEIRNTRNLTYIDPDALKELPLLKFLGIFNTGLKMP DLTKVYSTDIFFILEITDNPYMTSIPVNAFQGLCNETLTL KLYNNGFTSVQGYAFNGTKLDAVYLNKNKYLTVIDKD AFGGVYSGPSLLDVSQTSVTALPSKGLEHLAELIARNT WTLKKLPLSLSFLHLTRADLSYP SH |
| 16 | TSHR 21-282 D43A/E61A/K250A | GMGCSSPPCECHQEEDFRVTCKAIQRIPSLPPSTQTLKLI ATHLRTIPSHAFSNLPNISRIYVSIDVTLQQLESHSFYNLS KVTHIEIRNTRNLTYIDPDALKELPLLKFLGIFNTGLKMP DLTKVYSTDIFFILEITDNPYMTSIPVNAFQGLCNETLTL KLYNNGFTSVQGYAFNGTKLDAVYLNKNKYLTVIDKD AFGGVYSGPSLLDVSQTSVTALPSKGLEHLAELIARNT WTLKKLPLSLSFLHLTRADLSYP SH |

Fragments of the TSHR ectodomain were produced with various lengths and fused with the Fc regions of the immunoglobulin (FIGS. 1 and 2). The results of analysis of the M22 autoantibody neutralization rate of the TSHR fragments thus produced showed that, among the TSHR fragments, specific fragments had considerably excellent neutralization activity (FIG. 3).

In addition, it was found that thermostability at 37° C. was improved when some fragments of the TSHR ectodomains were fused with the carboxy-terminal cap (C-Cap) (FIGS. 12 to 13).

Accordingly, in one aspect, the present invention is directed to a fusion protein comprising an immunoglobulin Fc region or a carboxy-terminal cap (C-Cap) bound to a thyrotropin receptor (TSHR) fragment comprising the following mutation of (a) a fragment from the amino acid at position 21 to the amino acid at position 282 of the TSHR represented by the amino acid sequence of SEQ ID NO: 1, or (b) a fragment from the amino acid at position 21 to the amino acid at position 266 of the TSHR represented by the amino acid sequence of SEQ ID NO: 1.

The TSHR has been found to be an autoantigen of Graves' disease. Antibodies against TSHR are known to stimulate or inhibit the thyrotropin receptor (TSHR) expressed in the thyroid cell membrane, similar to the thyroid-stimulating hormone, and thereby to induce Graves' disease. In the present invention, the wild-type TSHR is represented by SEQ ID NO: 1.

SEQ ID NO: 1: TSHR full amino acid sequence
MRPADLLQLVLLLDLPRDLGGMGCSSPPCECHQEEDFRVTCKDIQRIPSL

PPSTQTLKLIETHLRTIPSHAFSNLPNISRIYVSIDVTLQQLESHSFYNL

-continued

SKVTHIEIRNTRNLTYIDPDALKELPLLKFLGIFNTGLKMFPDLTKVYST

DIFFILEITDNPYMTSIPVNAFQGLCNETLTLKLYNNGFTSVQGYAFNGT

KLDAVYLNKNKYLTVIDKDAFGGVYSGPSLLDVSQTSVTALPSKGLEHLK

ELIARNTWTLKKLPLSLSFLHLTRADLSYPSHCCAFKNQKKIRGILESLM

CNESSMQSLRQRKSVNALNSPLHQEYEENLGDSIVGYKEKSKFQDTHNNA

HYYVFFEEQEDEIIGFGQELKNPQEETLQAFDSHYDYTICGDSEDMVCTP

KSDEFNPCEDIMGYKFLRIVVWFVSLLALLGNVFVLLILLTSHYKLNVPR

FLMCNLAFADFCMGMYLLLIASVDLYTHSEYYNHAIDWQTGPGCNTAGFF

TVFASELSVYTLTVITLERWYAITFAMRLDRKIRLRHACAIMVGGWVCCF

LLALLPLVGISSYAKVSICLPMDTETPLALAYIVFVLTLNIVAFVIVCCC

YVKIYITVRNPQYNPGDKDTKIAKRMAVLIFTDFICMAPISFYALSAILN

KPLITVSNSKILLVLFYPLNSCANPFLYAIFTKAFQRDVFILLSKFGICK

RQAQAYRGQRVPPKNSTDIQVQKVTHDMRQGLHNMEDVYELIENSHLTPK

KQGQISEEYMQTVL

In one embodiment, the TSHR mutant may comprise a fragment from the amino acid at position 21 to the amino acid at position 282 of the TSHR represented by the amino acid sequence of SEQ ID NO: 1. The TSHR mutant may comprise, for example, a sequence represented by SEQ ID NO: 5.

In another embodiment, the TSHR mutant may comprise a fragment from the amino acid at position 21 to the amino acid at position 266 of the TSHR represented by the amino acid sequence of SEQ ID NO: 1. The TSHR mutant may comprise, for example, a sequence represented by SEQ ID NO: 6.

As used herein, the term "Fc region" means a protein that does not comprise the heavy-chain variable region and the light-chain variable region of the immunoglobulin and the light-chain constant region 1 (CL1), and the Fc region may be at least one Fc region selected from the group consisting of IgG1, IgG2, IgG3, IgG4, and IgD, or a fragment thereof or a hybrid Fc comprising a combination thereof.

In one embodiment, the hybrid Fc may comprise, for example, an IgD hinge region and a CH2 N-terminal region+ IG4 CH2 and CH3 regions, for example, a sequence represented by SEQ ID NO: 22. For example, the hybrid Fc can be the same hybrid Fc form disclosed as in Korean Patent No. 0897938, which is incorporated herein by reference.

```
SEQ ID NO: 22: IgG4 Fc
ESKYGPPCPPCPAPEFLGGPSVFLFPPKPKDTLMISRTPEVTCVVVDVSQ

EDPEVQFNWYVDGVEVHNAKTKPREEQFNSTYRVVSVLTVLHQDWLNGKE

YKCKVSNKGLPSSIEKTISKAKGQPREPQVYTLPPSQEEMTKNQVSLTCL

VKGFYPSDIAVEWESNGQPENNYKTTPPVLDSDGSFFLYS

RLTVDKSRWQ EGNVFSCSVM HEALHNHYTQ KSLSLSLGK
```

In another embodiment, the Fc region may be at least one Fc region selected from the group consisting of IgG1, IgG2, IgG3, and IgG4, or a fragment thereof or a hybrid Fc comprising a combination thereof.

The Fc region may comprise the entire Fc region constituting the immunoglobulin, and may often comprise a fragment thereof or an Fc region mutant. The Fc region may also comprise a Fc region mutant having a substitution of some amino acids or a combination with different kinds of Fc regions. The Fc region mutant can be modified to prevent cleavage in the hinge region. In addition, the Fc hinge sequence may have a partial substitution of the amino acid sequence in order to reduce antibody-dependent cell-mediated cytotoxicity (ADCC) or complement-dependent cytotoxicity (CDC). In addition, the hinge sequence of Fc may have a partial substitution of the amino acid sequence in order to suppress rearrangement of the Fab region. Furthermore, the lysine (K) at the C-terminus in the Fc region can be removed.

In addition, the Fc fragment of the present invention may be in the form of a wild-type sugar chain, a sugar chain increased compared to the wild type, a sugar chain decreased compared to the wild type, or a form from which a sugar chain is removed. The increase, decrease or removal of the sugar chain can be performed by a conventional method known in the art such as a chemical method, an enzymatic method, and a genetic-engineering method using microorganisms.

As used herein, the term "Fc fragment" is a term of the corresponding field used to describe a protein portion or a protein-folding structure that is regularly found at the carboxy terminal of an immunoglobulin. Fc fragments can be isolated from Fab fragments of monoclonal antibodies using enzymatic digestion such as papain digestion as an incomplete process (Mihaesco C et al., Journal of Experimental Medicine, 1968, Vol 127, 453). The Fc fragment combines with a Fab fragment (comprising an antigen-binding domain) to constitute a whole antibody, meaning a complete antibody. The Fc fragment consists of the carboxyl termini of antibody heavy chains. Each of the chains in the Fc fragment is about 220-265 amino acids in length, and the chains are often linked through disulfide bonds. Fc fragments often contain one or more independent structural folds or functional subdomains.

The term "Fc partial fragment" refers to a domain comprising less than the entire Fc fragment of an antibody, which retains a sufficient structure to have the same activity as the Fc fragment, comprising Fc[gamma]-receptor-binding activity. Thus, an Fc partial fragment may lack part or all of a hinge region, part or all of a CH2 domain, part or all of a CH3 domain, and/or part or all of a CH4 domain, depending on the isotype of the antibody from which the Fc partial domain is derived. An example of the Fc partial fragment comprises a molecule comprising the upper, core and lower hinge regions of IgG3 plus the CH2 domain (Tan, L K, et al., Proc Natl Acad Sci USA. 1990 January; 87(1): 162-166).

An Fc fragment also comprises respective heavy-chain constant region domains (e.g., CHI, CH2, CH3 and CH4 domains) and hinge regions of the different immunoglobulin classes and subclasses. Thus, human Fc partial domains of the present invention comprise the CHI domains of IgG1, IgG2, IgG3, IgG4, IgM, IgA1, IgA2, IgD and IgE, the CH2 domains of IgG1, IgG2, IgG3, IgG4, IgM, IgA1, IgA2, IgD and IgE, the CH3 domains of IgG1, IgG2, IgG3, IgG4, IgM, IgA1, IgA2, IgD and IgE, the CH4 domains of IgM and IgE, and the hinge regions of IgG1, IgG2, IgG3, IgG4, IgM, IgA1, IgA2, IgD and IgE. The corresponding Fc fragments in other species will depend on the immunoglobulins present in the species and the naming thereof.

Preferably, the Fc fragments according to the present invention comprise CHI, CH2 and hinge domains of IgG1 and the hinge domain of IgG2. The Fc fragment according to the present invention may further comprise a combination of one or more of these domains and hinges.

The immunoglobulin Fc region may have a structure in which the N-terminus of the Fc region is directly linked to the C-terminus of the TSHR fragment or is linked thereto via a linker. When the immunoglobulin Fc region is directly linked to the TSHR fragment, for example, the immunoglobulin Fc region according to the present invention may have a structure in which the N terminus of the Fc region of SEQ ID NO: 22 is linked to the C terminus of the TSHR fragment of SEQ ID NO: 5. The linking between TSHR and Fc is preferably a form in which the N-terminus of the Fc region is linked to the C-terminus of the TSHR.

When the linking is carried out via a linker, the linker may be linked to the N-terminus, C-terminus or free radical of the TSHR fragment and may be linked to the N-terminus, C-terminus or free radical of the Fc fragment. When the linker is a peptide linker, the link can occur at any site. For example, the linker may be linked to the C-terminus of the TSHR fragment and the N-terminus of the Fc region of the immunoglobulin.

In the case in which the linker and the Fc are bound to each other after being separately expressed, the linker may be a crosslinking agent known in the art. Examples of the crosslinking agent may comprise, but are not limited to, N-hydroxysuccinimide esters such as 1,1-bis(diazoacetyl)-2-phenylethane, glutaraldehyde or 4-azidosalicylic acid, imidoesters comprising disuccinimidyl ester such as 3,3'-dithiobis(succinimidylpropionate), or bifunctional maleimides such as bis-N-maleimido-1,8-octane.

In addition, the linker may be a peptide. Specifically, the linker may be a peptide comprising glycine and serine residues and consisting of 10 to 35 amino acid residues, more preferably a peptide comprising alanine, glutamic acid, threonine, lysine and arginine residues, and consisting of 35 amino acid residues, and most preferably any one peptide selected from the group consisting of SEQ ID NOS: 17 to 21, but is not limited thereto. Preferred linker sequences in the present invention are shown in Table 2 below.

TABLE 2

Linker sequence

| SEQ ID NO | Name | Linker sequence |
|---|---|---|
| 17 | L2 | A(EAAAK)₄A |
| 18 | CD | KARAAEAARAAEAAKAAEATKAAEAAAKAAKA |
| 19 | MCD | AEAAKAAEATKAAEAAAKAAKA |
| 20 | GS | (GGGGS)₃ |
| 21 | G8 | GGGGGGGG |

A specific example according to the present invention comprises a structure in which the immunoglobulin Fc region is linked to the TSHR fragment through a linker comprising the sequence of (GGGGS)₃ (SEQ ID NO: 20). The example shows that the activity of the fusion protein comprising the TSHR fragment bound to the immunoglobulin Fc via a linker comprising the sequence shown in SEQ ID NO: 20 is excellent (FIGS. 6 to 10).

In the present invention, the carboxy-terminal cap (C-Cap) can be used without any limitation as long as it is derived from a capping motif that induces structural stabilization of proteins. Preferably, the carboxy-terminal cap is derived from leucine repetition protein PP32 and more preferably, the carboxy-terminal cap comprises the amino acid sequence represented by any one selected from the group consisting of SEQ ID NOS: 23 to 28, but is not limited thereto.

In the present invention, the C-Cap may be characterized in that a hydrogen donor amino acid and a hydrogen acceptor amino acid for the formation of an additional hydrogen bond are substituted in the sequence.

In the present invention, the fusion protein may further comprise a linker and a tag for purification at the carboxy-terminus of the C-Cap.

Preferred C-Cap sequences according to the present invention are shown in Table 3.

TABLE 3

C-Cap sequence

| SEQ ID NO | Name | Linker sequence |
|---|---|---|
| 23 | #1 | YRENVFKLLPQLTYLDGYDRDDKE |
| 24 | #2 | DRENVFKLLPQLTYLYGYDRDDKE |
| 25 | #3 | YRENSFKLLPQLTYLDGYDRDDKE |
| 26 | #4 | YRESVFKLLPQLTYLDGYDRDDKE |
| 27 | #5 | YRENSFKLLPQLTYLEGYDRDDKE |
| 28 | #6 | YRESVFKLLPQLTYLEGYDRDDKE |

In the present invention, the fusion protein may be represented by the amino acid sequence of SEQ ID NO: 29 or 30.

SEQ ID NO: 29: TSHR(21-282)-GS(Linker)-Fc
GMGCSSPPCECHQEEDFRVTCKDIQRIPSLPPSTQTLKLIETHLRTIPSH

AFSNLPNISRIYVSIDVTLQQLESHSFYNLSKVTHIEIRNTRNLTYIDPD

ALKELPLLKFLGIFNTGLKMFPDLTKVYSTDIFFILEITDNPYMTSIPVN

AFQGLCNETLTLKLYNNGFTSVQGYAFNGTKLDAVYLNKNKYLTVIDKDA

FGGVYSGPSLLDVSQTSVTALPSKGLEHLKELIARNTWTLKKLPLSLSFL

HLTRADLSYPSHGGGGSGGGGSGGGGSESKYGPPCPPCPAPEFLGGPSVF

LFPPKPKDTLMISRTPEVTCVVVDVSQEDPEVQFNWYVDGVEVHNAKTKP

REEQFNSTYRVVSVLTVLHQDWLNGKEYKCKVSNKGLPSSIEKTISKAKG

QPREPQVYTLPPSQEEMTKNQVSLTCLVKGFYPSDIAVEWESNGQPENNY

KTTPPVLDSDGSFFLYSRLTVDKSRWQEGNVFSCSVMHEALHNHYTQKSL

SLSLGK

SEQ ID NO: 30:: TSHR(21-266)-C-Cap-Linker-6xHis
GMGCSSPPCECHQEEDFRVTCKDIQRIPSLPPSTQTLKLIETHLRTIPSH

AFSNLPNISRIYVSIDVTLQQLESHSFYNLSKVTHIEIRNTRNLTYIDPD

ALKELPLLKFLGIFNTGLKMFPDLTKVYSTDIFFILEITDNPYMTSIPVN

AFQGLCNETLTLKLYNNGETSVQGYAFNGTKLDAVYLNKNKYLTVIDKDA

FGGVYSGPSLLDVSQTSVTALPSKGLEHLKELIARNTWTLKKLPLS<u>YREN</u>

<u>SFKLLPQLTYLDGYDRDDKE</u>GGGSGGGSHHHHHHHH

In another aspect, the present invention is directed to a nucleic acid encoding the fusion protein comprising the TSHR fragment or a recombinant vector comprising the nucleic acid.

The fusion protein comprising the TSHR fragment can be recombinantly produced by isolating the nucleic acid encoding the fusion protein comprising the TSHR fragment. The nucleic acid is isolated and inserted into a replicable vector to conduct further cloning or further expression. Based on this, in another aspect, the present invention is directed to a vector comprising the nucleic acid.

As used herein, the term "nucleic acid" is intended to encompass both DNA (gDNA and cDNA) and RNA molecules, and nucleotides, which are basic constituent units of the nucleic acid, comprise naturally derived nucleotides as well as analogues having modified sugar or base moieties. The sequence of nucleic acid encoding the fusion protein comprising the TSHR fragment according to the present invention can be varied. Such variation comprises addition, deletion, or non-conservative substitution or conservative substitution of nucleotides.

The nucleic acid according to the present invention is also interpreted to comprise a nucleotide sequence showing substantial identity with the sequence. The term "sequence showing substantial identity" means a sequence that shows an identity of at least 80%, more preferably, at least 90%, most preferably at least 95%, when aligning the sequence of the present invention so as to correspond to the other sequence as highly as possible and analyzing the aligned sequence using an algorithm commonly used in the art.

The DNA encoding the fusion protein comprising the TSHR fragment is easily isolated and synthesized using a conventional process.

As used herein, the term "vector" refers to a means for expressing target genes in host cells and comprises: plasmid vectors; cosmid vectors; and viral vectors such as bacteriophage vectors, adenovirus vectors, retroviral vectors and adeno-associated viral vectors. Acceptable vector components generally comprise, but are not limited to, one or more of the following components: signal sequences, replication origins, one or more marker genes, enhancer elements, promoters and transcription termination sequences.

The nucleic acid encoding the fusion protein comprising the TSHR fragment in the vector is operatively linked to a promoter.

The term "operatively linked" means a functional linkage between a nucleic acid expression control sequence (e.g., promoter, signal sequence or array of transcription regulator binding site) and another nucleic acid sequence, and this enables the control sequence to regulate transcription and/or translation of the other nucleic acid sequence.

When a prokaryotic cell is used as a host, the vector generally comprises a potent promoter capable of conducting transcription (such as a tac promoter, lac promoter, lacUV5 promoter, 1pp promoter, pLλ promoter, pRλ promoter, racy promoter, amp promoter, recA promoter, SP6 promoter, trp promoter, or T7 promoter), a ribosome-binding site to initiate translation, and a transcription/translation termination sequence. In addition, when a eukaryotic cell is used as a host, the vector comprises, for example, a promoter (e.g., a metallothionein promoter, a β-actin promoter, a human hemoglobin promoter and a human muscle creatine promoter) derived from the genome of mammalian cells, or a promoter derived from an animal virus (e.g., adenovirus late promoter, vaccinia virus 7.5K promoter, SV40 promoter, cytomegalovirus (CMV) promoter, HSV tk promoter, mouse breast tumor virus (MMTV) promoter, HIV LTR promoter, Moloney virus promoter, Epstein-Barr virus (EBV) promoter, and Rous sarcoma virus (RSV) promoter), and generally has a polyadenylation sequence as a transcription termination sequence.

Optionally, the vector may be fused with another sequence in order to facilitate purification of the fusion protein comprising a TSHR fragment expressed therefrom. The sequence to be fused comprises, for example, glutathione S-transferase (Pharmacia, USA), maltose-binding protein (NEB, USA), FLAG (IBI, USA), 6×His (hexahistidine; Qiagen, USA) and the like.

The vector comprises antibiotic-resistant genes commonly used in the art as selectable markers, and examples thereof comprise genes resistant to ampicillin, gentamycin, carbenicillin, chloramphenicol, streptomycin, kanamycin, geneticin, neomycin and tetracycline.

In another aspect, the present invention is directed to a recombinant cell introduced with the recombinant vector described above and a method for producing the fusion protein using the recombinant cell. The cell may be a prokaryotic, yeast or higher eukaryotic cell, but is not limited thereto.

In the present invention, the method for producing the fusion protein comprises: (a) culturing the recombinant cell to express the fusion protein; and (b) recovering the expressed fusion protein.

*Escherichia coli*, strains of the genus *Bacillus* such as *Bacillus subtilis* and *Bacillus thuringiensis*, and prokaryotic host cells such *Streptomyces, Pseudomonas* (for example, *Pseudomonas putida*), *Proteus mirabilis* and *Staphylococcus* (for example, *Staphylococcus carnosus*) can be used.

Interest in animal cells is the greatest, and examples of useful host cell lines comprise, but are not limited to, COS-7, BHK, CHO, CHOK1, DXB-11, DG-44, CHO/−DHFR, CV1, COS-7, HEK293, BHK, TM4, VERO, HELA, MDCK, BRL 3A, W138, Hep G2, SK-Hep, MMT, TRI, MRC 5, FS4, 3T3, RIN, A549, PC12, K562, PER.C6, SP2/0, NS-0, U20S, or HT1080.

Most preferred host cells that can be used in the present invention comprise, but are not limited to, immortal hybridoma cells, NS/0 myeloma cells, 293 cells, Chinese hamster ovary cells (CHO cells), HeLa cells, CAP cells (human amniotic fluid-derived cells) and COS cells.

The cells can be cultured in various media. Any commercially available medium can be used as a culture medium without limitation. All other essential supplements known to those skilled in the art may be contained in appropriate concentrations. Culture conditions, such as temperature, pH, etc., have already been used for expression along with the selected host cells, which will be apparent to those skilled in the art.

The recovery of the fusion protein comprising the TSHR fragment can be carried out, for example, by removing impurities through centrifugation or ultrafiltration, and purifying the resulting product, for example, using affinity chromatography. Other additional purification techniques, such as anion or cation exchange chromatography, hydrophobic interaction chromatography, hydroxyl apatite chromatography and the like may be used.

Meanwhile, the present invention aims to identify whether or not a fusion protein can actually effectively neutralize an autoantibody in a blood sample of a patient with Graves' disease.

That is, in another example of the present invention, it was identified whether or not an autoantibody was neutralized in a blood sample of a patient with Graves' disease at different concentrations of the fusion protein. As a result, it was found that the fusion protein at a concentration of 10 μg/ml exhibited a satisfactory autoantibody-neutralizing effect in all blood samples of patients with Graves' disease (FIGS. 6 to 9).

Accordingly, in another aspect, the present invention is directed to a pharmaceutical composition for treating or preventing Graves' disease containing the fusion protein comprising the TSHR fragment.

The pharmaceutical composition may comprise a therapeutically effective amount of a TSHR fragment-containing fusion protein and a pharmaceutically acceptable carrier. The "pharmaceutically acceptable carrier" is a substance that can be added to the active ingredient to help formulate or stabilize the formulation and does not cause significantly harmful toxic effects to patients.

The "carrier" is a carrier or diluent that does not impair biological activities or properties and does not irritate a patient. Acceptable pharmaceutical carriers for compositions, which are formulated into liquid solutions, are sterilized and biocompatible, and examples thereof comprise saline, sterile water, Ringer's solution, buffered saline, albumin injection solutions, dextrose solutions, maltodextrin solutions, glycerol, ethanol and mixtures of one or more thereof. If necessary, other conventional additives such as antioxidants, buffers and bacteriostatic agents may be added. In addition, diluents, dispersants, surfactants, binders and lubricants can be additionally added to formulate injectable solutions such as aqueous solutions, suspensions and emulsions, pills, capsules, granules or tablets.

Pharmaceutically acceptable carriers comprise sterile aqueous solutions or dispersions and sterile powders for the extemporaneous preparation of sterile injectable solutions or dispersions. The use of such media and agents for pharmaceutical active substances is well known in the art. The composition is preferably formulated for parenteral injection. The composition may be formulated as a solution, microemulsion, liposome, or other ordered structures suitable for high drug concentrations. The carrier can be, for example, a solvent or dispersion medium containing water, ethanol, a polyol (such as glycerol, propylene glycol and liquid polyethylene glycol) and a suitable mixture thereof. In some cases, the composition may comprise isotonic agents, for example, sugars, polyalcohols such as mannitol, sorbitol or sodium chloride. Sterile injectable solutions may be prepared by incorporating a required amount of the active compound in an appropriate solvent, optionally together with one of the ingredients described above or a combination thereof, followed by sterile microfiltration. In general, dispersions are prepared by incorporating the active compound into a basic dispersion medium and a sterile vehicle containing other necessary ingredients selected from among those described above. In the case of sterile powders for the preparation of sterile injectable solutions, some preparation methods involve vacuum drying and freeze-drying (lyophilizing) to produce powders of the active ingredient and any additional desired ingredients from a pre-sterilized and filtered solution thereof.

Specifically, the pharmaceutical composition may comprise, but are not limited to, a formulation material to modify, maintain or preserve the pH, osmolality, viscosity, transparency, color, isotonicity, odor, sterility, stability, dissolution or release rate, adsorption or transmission thereof. Suitable formulation materials comprise, but are not limited to, amino acids (such as glycine, glutamine, asparagine, arginine or lysine), antimicrobials, antioxidants (such as ascorbic acid, sodium sulfite or sodium bisulfite), buffers (such as borate, bicarbonate, tris-HCl, citrate, phosphate or other organic acids), bulking agents (such as mannitol or glycine), chelating agents [such as ethylenediaminetetraacetic acid (EDTA)], complexing agents (such as caffeine, polyvinylpyrrolidone, beta-cyclodextrin or hydroxypropyl-beta-cyclodextrin), fillers, monosaccharides, disaccharides and other carbohydrates (such as glucose, mannose, or dextrin), proteins (such as serum albumin, gelatin, or immunoglobulin), colorants, flavors, diluents, emulsifiers, hydrophilic polymers (such as, polyvinylpyrrolidone), low-molecular-weight polypeptides, salt-formation-inhibiting ions (such as sodium), preservatives (such as benzalkonium chloride, benzoic acid, salicylic acid, thimerosal, phenethyl alcohol, methylparaben, propylparaben, chlorhexidine, sorbic acid or hydrogen peroxide), solvents (such as glycerin, propylene glycol or polyethylene), sugar alcohols (such as mannitol or sorbitol), suspension agents, surfactants or wetting agents [such as Pluronics, PEG, sorbitan ester, polysorbate such as polysorbate 20 or polysorbate 80, triton, tromethamine, lecithin, cholesterol or tyloxapol], stability enhancers (such as sucrose or sorbitol), tonicity enhancers (such as an alkali metal halide, preferably sodium chloride or potassium chloride; or mannitol or sorbitol), delivery vehicles, diluents, excipients and/or pharmaceutical adjuvants.

The present invention also relates to a composition for treating or preventing a thyrotropin receptor-associated disease comprising a TSHR-fragment-containing fusion protein as an active ingredient, or a method for treating a thyrotropin receptor-associated disease comprising administering a TSHR-fragment-containing fusion protein to a subject in need of treatment.

The thyrotropin receptor-associated disease may for example comprise Graves' disease or Graves' ophthalmopathy.

The TSHR-fragment-containing fusion protein can be administered via any route. For example, the protein can be administered to animals through any appropriate means, directly (e.g., through injection, graft or local administration, or topical administration to the tissue site) or systemically (e.g., parenterally or orally).

When the composition is provided parenterally, such as through intravenous, subcutaneous, ophthalmic, intraperitoneal, intramuscular, oral, rectal, intraorbital, intracerebral, intracranial, intraspinal, intraventricular, intrathecal, intracisternal, intracapsular, intranasal or aerosol administration, it may comprise a portion of an aqueous or physiologically compatible body fluid suspension or solution. Accordingly, since a carrier or vehicle is physiologically acceptable, it can be added to the fusion protein and delivered to a patient. Thus, the composition may generally comprise a physiological saline as a carrier like body fluid for formulation.

The frequency of administration will depend on the pharmacokinetic parameters of the TSHR-fragment-containing fusion protein in the formulation that is used. Typically, the clinician may conduct administration in a dose that achieves the desired effect. Thus, it can be administered as a single dose, as two or more doses (which may or may not contain the same amount of the target fusion protein) with a time interval therebetween, or as a continuous infusion through a graft device or catheter. Additional refinement of an appropriate dosage is routinely conducted by those skilled in the art and falls within the scope of work routinely conducted by them.

The unit dosage ranges from 0.01 µg/kg body weight to 100 mg/kg body weight in humans, specifically 1 µg/kg body weight to 30 mg/kg body weight. Although the content defined above is the optimum amount, it may vary depending on the type of disease to be treated and the presence of side effects, and the optimal dosage may be determined through conventional experiments. The administration of the fusion protein can be carried out by periodic bolus injections, or continuous intravenous, subcutaneous or intraperitoneal administration from an external reservoir (e.g., intravenous bag) or an internal reservoir (e.g., a bioerodible implant).

The frequency of administration depends on the severity of the condition. The frequency can range from three times per week to once every week or two weeks.

Optionally, the TSHR-fragment-containing fusion protein can be administered to a subject receptor along with other biologically active molecules. However, the optimal combination of the fusion protein and other molecules, administration form and dosage may be determined through routine experimentation well known in the art.

The term "therapeutically effective amount" as used herein refers to an amount which is sufficient for treating a disease at a reasonable benefit/risk ratio applicable to all medical treatments and means the amount of the TSHR-fragment-containing fusion protein according to the present invention. The exact amount may be varied depending on a variety of factors comprising, but not limited to, ingredients and physical properties of the therapeutic composition, the intended patient population, and individual patient considerations, and can be easily determined by those skilled in the art. When thoroughly taking into consideration these factors, it is important to administer a minimal amount sufficient to achieve maximum efficacy without side effects, and this dosage can be easily determined by those skilled in the art.

The dosage of the pharmaceutical composition of the present invention is not particularly limited, but depends on a variety of factors comprising health conditions and the body weight of patient, the severity of disease, the type of drug, the administration route and the administration period. The composition may be administered in a single dose or multiple doses daily to mammals comprising rats, mice, domestic animals, humans and the like, via a typically acceptable route, for example, orally, rectally, intravenously, subcutaneously, intrauterinely or intracerebrovascularly.

In another embodiment of the present invention, the amount of autoantibody in the sample was measured through ELISA using the TSHR fusion protein developed in the present invention (FIG. 15). That is, the fusion protein of the present invention can be used for neutralization of autoantibody as well as for the diagnosis of Graves' disease through measurement of the amount of autoantibody in the sample.

Accordingly, in another aspect, the present invention is directed to a composition for diagnosing Graves' disease comprising the TSHR-fragment-containing fusion protein.

Accordingly, in another aspect, the present invention is directed to a kit for diagnosing Graves' disease comprising the composition for diagnosing Graves' disease.

In the present invention, the kit may comprise various buffers, washing solutions and labeling materials, if necessary.

Unless defined otherwise, all technical and scientific terms used herein have the same meanings as those appreciated by those skilled in the field to which the present invention pertains. Repeated descriptions of the same technical configurations and operations as those of the prior art will be omitted.

EXAMPLE

Hereinafter, the present invention will be described in more detail with reference to specific examples. However, it will be obvious to those skilled in the art that the present invention is not limited to the following examples and a variety of modifications and alterations are possible without departing from the ideas and scope of the present invention.

Preparation Example 1. Preparation and Purification of Fusion Proteins Containing TSHR Mutants Preparation Example 1-1. Production of Protein Expression Vector In order to increase the biological activity of thyrotropin receptor mutants, various combinations of fusion proteins mutants bound to Fc or C-Cap were designed as shown in Table 4.

TABLE 4

TSHR mutant fusion protein structures

| SEQ ID NO | Name | Linker | Fusion protein |
|---|---|---|---|
| 2 | TSHR 21-417 (TR1-Fc) | Absence | IgG4-Fc (SEQ ID NO 22) |
| 3 | TSHR 21-417 Δ368-376 (TR2-Fc) | Absence | IgG4-Fc (SEQ ID NO 22) |
| 4 | TSHR 21-417 Δ368-376 C3915/C3985/C4085 (TR3-Fc) | Absence | IgG4-Fc (SEQ ID NO 22) |
| 5 | TSHR 21-282 (TR4-Fc) | Absence | IgG4-Fc (SEQ ID NO 22) |
| 7 | TSHR 21-231 (TR5-Fc) | Absence | IgG4-Fc (SEQ ID NO 22) |
| 8 | TSHR 21-206 (TR6-Fc) | Absence | IgG4-Fc (SEQ ID NO 22) |
| 9 | TSHR 21-156 (TR7-Fc) | Absence | IgG4-Fc (SEQ ID NO 22) |
| 10 | TSHR 21-127 (TR8-Fc) | Absence | IgG4-Fc (SEQ ID NO 22) |
| 11 | TSHR 157-294 (TR-9-Fc) | Absence | IgG4-Fc (SEQ ID NO 22) |
| 12 | TSHR 21-282 D43A (N01) | Absence | IgG4-Fc (SEQ ID NO 22) |
| 13 | TSHR 21-282 E61A (N02) | Absence | IgG4-Fc (SEQ ID NO 22) |
| 14 | TSHR 21-282 D43A/E61A (N03) | Absence | IgG4-Fc (SEQ ID NO 22) |
| 15 | TSHR 21-282 K250A (N04) | Absence | IgG4-Fc (SEQ ID NO 22) |
| 16 | TSHR 21-282 D43A/E61A/K250A (N05) | Absence | IgG4-Fc (SEQ ID NO 22) |

TABLE 4 -continued

TSHR mutant fusion protein structures

| SEQ ID NO | Name | Linker | Fusion protein |
|---|---|---|---|
| 29 | TSHR 21-282-GS-Fc (TR-GS) | (GGGGS)3 (SEQ ID NO 20) | IgG4-Fc (SEQ ID NO 22) |
| 30 | TSHR 21-266-C-Cap (TR-C-Cap) | Absence | C-Cap #5 (SEQ ID NO 27) |
| 31 | TSHR 21-282-L2-Fc (TR-L2) | A(EAAAk)4A (SEQ ID NO 17) | IgG4-Fc (SEQ ID NO 22) |
| 32 | TSHR 21-282-CD-Fc (TR-CD) | KARAAEAARA AEAAKAAEAT KAAEAAAKA AKA (SEQ ID NO 18) | IgG4-Fc (SEQ ID NO 22) |
| 33 | TSHR 21-282-MCD-Fc (TR-MCD) | AEAAKAAEAT KAAEAAAKA AKA (SEQ ID NO 19) | IgG4-Fc (SEQ ID NO 22) |
| 34 | TSHR 21-282-G8-Fc (TR-G8) | GGGGGGGG (SEQ ID NO 21) | IgG4-Fc (SEQ ID NO 22) |
| 35 | TSHR 21-266-C-Cap #1 | Absence | C-Cap #1 (SEQ ID NO 23) |
| 36 | TSHR 21-266-C-Cap #2 | Absence | C-Cap #2 (SEQ ID NO 24) |
| 37 | TSHR 21-266-C-Cap #3 | Absence | C-Cap #3 (SEQ ID NO 25) |
| 38 | TSHR 21-266-C-Cap #4 | Absence | C-Cap #4 (SEQ ID NO 26) |
| 39 | TSHR 21-266-C-Cap #6 | Absence | C-Cap #6 (SEQ ID NO 28) |

Based on each amino acid sequence of the thyrotropin receptor mutant protein, a nucleotide sequence encoding the same was synthesized by Bioneer Corp. NheI and NotI restriction enzyme sequences were added to the 5' and 3' ends of each nucleotide sequence encoding the thyrotropin receptor mutant protein. A start codon for protein translation and an induction sequence to secrete the expressed protein outside the cell were inserted after the restriction enzyme sequence at the 5' end. A stop codon was inserted after the nucleotide sequence encoding each thyrotropin receptor mutant protein. Nucleotide sequences respectively encoding thyrotropin receptor mutant proteins were cloned into the pcDNA3.1-empty expression vector using two restriction enzymes, NheI and NotI. The pcDNA3.1-empty expression vector was obtained from Invitrogen Corporation (USA) and is an expression vector having a simple structure comprising a CMV promoter, a pUC-derived replication origin, an SV40-derived replication origin and an ampicillin-resistant gene.

Preparation Example 1-2. Production of Plasmid DNA for Protein Expression

Each expression vector was transformed into E. coli TOP10 competent cells (Thermo Fisher Scientific) to obtain a large amount of plasmid DNA used for expression. Each expression vector was transduced in E. coli with weakened cell walls through heat shock and plated on LB plates to obtain colonies. The obtained colonies were inoculated on LB medium and cultured for 16 hours to obtain 100 µl of each E. coli having the expression vector in the cell. The obtained E. coli was centrifuged to remove the culture medium, and P1, P2, and P3 solutions (QIAGEN, cat. No.: 12963) were added to break the cell walls and thereby obtain a DNA suspension from which protein and DNA were separated. The plasmid DNA was purified from the obtained suspension using a Qiagen DNA purification column. The eluted DNA was identified by agarose gel electrophoresis and the concentration and purity thereof were measured using a nano drop device (Thermo Scientific, Nanodrop Lite) and then used for expression.

Preparation Example 1-3. Expression of Mutant Proteins in HEK293 Cells

A human cell line was transformed with each plasmid DNA. Each plasmid DNA was transfected into 293F cells (FreeStyle 293-F, Thermo Fisher Scientific) cultured in FreeStyle 293 medium (Life technologies) using a PEI solution (Polyplus Co. Ltd., cat. no.: 101-10N). The mixture of DNA and PEI solution was mixed with suspended cells using Freestyle 293 (Invitrogen) expression medium and cultured for 24 hours, and then 10% select Soytone stock was added at 0.5% (v/v) thereto. After 5 days of culture, cells were removed by centrifugation to obtain a supernatant containing a thyrotropin receptor (TSHR) mutant protein.

Preparation Example 1-4. Expression of Mutant Proteins in CHO Cells

A human cell line was transformed with each plasmid DNA. Each plasmid DNA was transfected into CHO-S cells (FreeStyle CHO-S, Thermo Fisher Scientific) cultured in TransFx-C medium (HyClone) using a FectoPro DNA transfection reagent solution (Polyplus Co. Ltd., cat. no.: 116-010). The mixture of DNA and FectoPro solution was mixed with suspended cells using TransFx-C(HyClone) expression medium and cultured for 4 hours and then 10% select Soytone stock was added at 0.5% (v/v) thereto. After 5 days of culture, cells were removed by centrifugation to obtain a supernatant containing a thyrotropin receptor (TSHR) mutant protein.

Preparation Example 1-5. Purification of Fusion Protein Fused with Thyrotropin Receptor (TSHR) Mutant Protein and Fc Region A protein A affinity chromatography column (GE Healthcare) was equilibrated with a 20 mM sodium phosphate (pH 7.2) buffer. The culture supernatant containing TSHR-Fc protein was filtered through a 0.2 μm filter and then loaded onto a Protein A affinity chromatography column. The column was washed with 20 mM sodium phosphate buffer and eluted with 100 mM glycine (pH 3.3) buffer, and then the protein eluted with 1 M Tris buffer was neutralized. Proteins obtained through Protein A affinity chromatography were again purified using a Poros HQ (Life Technologies) anion chromatography column. The Poros HQ anion chromatography column was equilibrated with a 50 mM Tris (pH 8.0) buffer and then the protein eluted through Protein A affinity chromatography was loaded. After washing the column with 50 mM Tris (pH 8.0) buffer, a 50 mM Tris (pH 8.0) buffer containing 1 M sodium chloride was flowed at a concentration gradient and the eluted fractions were analyzed. Each fraction was analyzed under SDS-PAGE reduction conditions to collect a portion of high purity TSHR-Fc proteins and then dialyzed overnight with final buffer 1×PBS at 4° C. and at pH 7.4. After dialysis, the resulting solution was concentrated at 2,500 rpm and 4° C. using a 30,000 MW cutoff centrifugal filter. The concentration of the concentrated TSHR-Fc protein was measured using a NanoDrop device (Thermo Scientific).

Preparation Example 1-6. Purification of Thyrotropin Receptor (TSHR) C-Cap Mutant Fusion Protein A Ni-Sepharose (GE-17-3712-02, GE Healthcare) column was equilibrated with 20 mM sodium phosphate (pH 7.2) and 0.5 M sodium chloride buffer. The culture supernatant containing TR-C-Cap protein was filtered through a 0.2 μm filter and loaded onto a Ni-Sepharose column. The column was washed with 20 mM sodium phosphate buffer (pH 7.2), 0.5 M sodium chloride and 10 to 50 mM imidazole buffer, and eluted with 20 mM sodium phosphate buffer (pH 7.2), 0.5 M sodium chloride and 0.5 M imidazole buffer. Each fraction was analyzed under SDS-PAGE reduction conditions to collect a portion of high-purity TR-C-Cap proteins and then dialyzed overnight with final buffer 1×PBS at 4° C. and at pH 7.4. After dialysis, the resulting solution was concentrated at 2,500 rpm and 4° C. using a 10,000 MW cutoff centrifugal filter. The concentration of the concentrated TR-Fc protein was measured using a NanoDrop device (Thermo Scientific).

Experimental Example 1. Results of Measurement of Activity of Fusion Protein

Experimental Example 1-1. Measurement Method

1) Determination of M22 Antibody-Blocking Activity

The activity of blocking the M22 antibody by the fusion protein prepared by the method to was evaluated using an KRONUS ELISA Kit (KRONUS, USA).

Fusion proteins were serially diluted 2-fold at a concentration from 20 μg/mL to 0.039 μg/mL to prepare 10 serial dilution samples. In addition, 45 μL of the 10 serial dilution samples, a standard material and 60 μL of a peroxide-M22 antibody were reacted and allowed to stand at room temperature for 90 minutes, and 75 μL of a starting solution and 75 μL of a blocking reaction-completed sample were added to the 96-well plate. After being allowed to stand at room temperature for 90 minutes, the solution in the 96-well plate was completely removed and washed three times, and 100 μL of a TMB coloring solution was added thereto. After being allowed to stand at room temperature for 25 minutes, the reaction solution was added with 50 μL of a stop solution and analyzed at A450 nm.

2) Identification of TSH-Blocking Activity

The activity of blocking the TSH antibody by the fusion protein prepared by the method was evaluated using an EAGLE ELISA Kit (EAGLE, USA).

Fusion proteins were serially diluted 2-fold at a concentration from 100 μg/mL to 0.195 μg/mL to prepare 10 serial dilution samples. In addition, 60 μL of the 10 serial dilution samples, a standard material and 60 μL of a TSH complex were reacted and allowed to stand at room temperature for 90 minutes, and 50 μL of a starting solution and 100 μL of the blocking reaction-completed sample were added to the 96-well plate. After being allowed to stand at room temperature for 120 minutes, the solution in the 96-well plate was completely removed and washed three times, and then 100 μL of an SA-POD conjugate was added thereto. After being allowed to stand at room temperature for 60 minutes, the solution in the 96-well plate was completely removed and washed three times, and 100 μL of a TMB coloring solution was added thereto. After being allowed to stand at room temperature for 20 minutes, the reaction solution was added with 50 μL of a stop solution and analyzed at A450 nm.

Experimental Example 1-2. Results of Measurement of Activity According to Type of TSHR Mutant IC50 values for M22 antibodies and the TSH-blocking activity of the TSHR mutant-fusion proteins TR1-Fc, TR2-Fc, TR3-Fc, TR4-Fc, TR5-Fc, TR6-Fc, TR7-Fc, TR8-Fc, TR9-Fc, N01, N02, N03, N04 and N05 prepared in Preparation Example above were measured by the method of Experimental Example 1.

The results showed that, except for fusion proteins that were not expressed, TR1-Fc, TR3-Fc, TR4-Fc, TR8-Fc and TR9-Fc were expressed, and TR4-Fc was the most active (FIG. 3).

Also, the results of measurement of IC50 values of N01, N02, N03, N04 and N05 showed that none of N01 to N05 exhibited TSH-blocking activity, and N01 showed an IC50 value of 3.0 μg/ml against the M22 antibody, while N02 to N05 did not exhibit reactivity at all.

The reactivity of TR-C-Cap #1, TR-C-Cap #2, TR-C-Cap #3, TR-C-Cap #4, TR-C-Cap #5 and TR-C-Cap #6 was observed. As a result, TR-C-Cap #3 and TR-C-Cap #5 were observed to exhibit excellent reactivity (FIG. 12).

Experimental Example 1-3. Measurement Results of Activity According to Type of Linker IC50 values for M22 antibodies and TSH-blocking activity of TR4-Fc, TR-L2, TR-CD, TR-MCD, TR-GS and TR-G8 prepared in Preparation Example above were measured by the method of Experimental Example 1.

The results showed that none of the fusion proteins exhibited TSH-blocking activity and that the linker-bound fusion proteins had higher IC50 values for M22 antibodies than TR4-Fc to which the linker was not bound (FIG. 5).

Experimental Example 2. Identification of Neutralization Reactivity of Blood of GD/GO Patients

Experimental Example 2-1. Measurement Method

The neutralization reactivity of autoantibody present in the blood of patients with Graves' disease (GD) and Graves' ophthalmopathy (GO) by the mutant fusion proteins prepared according to Preparation Example above was evaluated using a Thyretain TSI Reporter Bioassay kit (Quidel, USA). 100 μL of a cell adhesion solution was added to a 96-well plate (black, clear bottom, poly-lysine treated) and allowed to stand on a clean bench for 10 minutes. The CHO-MC4 cells provided in the kit prepared in a cell growth solution were uniformly added at 100 μL to a 96-well plate (black, clear bottom, poly-lysine treated) and then cultured in a $CO_2$ incubator for 15-18 hours.

The prepared fusion proteins on the following day were prepared at concentrations of 2.5, 5, 10, 20 μg/mL and the like, and reacted with the selected patient blood at 37° C. for 1 hour. Then, the 96-well plate provided with CHO-MC4 cells prepared the day before were washed twice with the reaction buffer provided in the kit, and 100 μL of a mixture of the prepared patient blood and mutant TSHR-Fc was added thereto. The 96-well plate containing the mixture was incubated in a $CO_2$ incubator for 3 hours. After adding 75 μL of a luciferase substrate solution, the mixture was incubated at 25° C. for 10 minutes and then measured with a luminometer. Finally, when the value of % SRR (sample to reference ratio %) was less than 140, it was considered negative.

Experimental Example 2-2. Identification of Neutralization Reactivity of TSHR Mutant-Fc Fusion Protein A total of 42 blood samples were reacted with TR4-Fc, TR-L2, TR-GS and TR-CD. It was identified that, when fusion proteins were used at 2.5 μg/ml, they were respectively capable of neutralizing 19, 19, 25 and 18 blood samples (FIGS. 6 and 7).

Among the 42 blood samples, 6 blood samples were not neutralized at the concentration of 5 μg/mL of all candidate materials due to high autoantibody concentrations. When the six blood samples mentioned above were reacted with a concentration of 10 μg/mL of blood samples, TR-GS neutralized all of the six blood samples, TR4-Fc neutralized only five blood samples, and TR-L2 and TR-CD each neutralized only one blood sample (FIGS. 8 and 9). This indicates that TR-GS showed the best neutralizing effect among the fusion proteins mentioned above.

Experimental Example 2-3. Identification of Neutralization Reactivity of TSHR Mutant-C-Cap Fusion Protein In order to identify the blood neutralization reaction of the TR-C-Cap mutant, #18 blood having a large amount of autoantibody was selected and subjected to experimentation. The blood was reacted with TR-GS and TR-C-Cap, and respective fusion proteins were stored at 37° C. for 1 day and 2 days and comparatively used. When using the fusion proteins at 5, 20 and 50 μg/mL, TR-C-Cap exhibited a neutralization effect even after 2 days of storage at 37° C., but TR-GS exhibited a remarkably reduced neutralization effect even after 1 day at 37° C. (FIG. 13). In order to accurately measure the IC50 value, the neutralization effect was measured at 0.39 to 12.5 μg/mL. As a result, it was confirmed that TR-GS had IC50 of 2.015 μg/mL (37 degrees, 0 days) and TR-C-Cap had IC50 of 0.4439, 1.782, and 4.469 μg/mL (37 degrees, 0 days, 1 day and 2 days), respectively. (FIG. 14). Therefore, it was identified that the thermostability at 37° C. was enhanced by the introduction of C-Cap.

Experimental Example 3: Measurement of Pharmacokinetics of Fusion Proteins

Experimental Example 3-1. Measurement Method of Pharmacokinetics 8-week-old female C57BL/6 mice purchased from Orient BIO (Korea) were weighed on the drug treatment day and grouped (n=3 per blood collection time), the sample (TR-GS) was intravenously administered at a dosage of 2 mg/mL/kg and blood samples were collected 5 minutes, 30 minutes, and 1, 2, 4, 8, 24, 48 and 72 hours after drug administration. In order to measure the concentration of TR-GS in the blood, an in-house ELISA method having immunoreactivity to TSHR and IgG4 Fc was used for the present experimentation. The concentrations of the samples in the blood were measured up to 72 hours after subcutaneous injection into mice.

Experimental Example 3-2. Results of Measurement of Pharmacokinetic Activity In order to evaluate the pharmacokinetics of the TR-GS fusion protein, the concentration of TR-GS in the blood was measured up to 72 hours after intravenous injection into mice.

As a result, as shown in FIG. 10, the half-life of TR-GS previously expressed in HEK cells was 5.6 hours, whereas the half-life of TR-GS expressed in CHO cells was 31.2 hours (FIG. 10).

Experimental Example 4. Evaluation of Neutralizing Effect of Fusion Proteins in Mouse

Experimental Example 4-1. Evaluation Method of Neutralizing Effect in Mouse 20 to 22 g of 8 to 10-week-old female C57BL/6 mice (Orient BIO, Korea) were used. K1-18 as an autoantibody was intraperitoneally administered to 6 μg/head (0.3 mg/kg). After 30 minutes, TR-GS was intravenously administered at 48 μg/head (2.4 mg/kg) or 144 μg/head (7.2 mg/kg). The total amount of T4 in the blood was measured using a total T4 ELISA kit (Sigma-Aldrich, USA).

Experimental Example 4-2. Identification of Neutralization Efficacy of K1-18 and TR-GS It was found that the total T4 concentration in the blood after administration of K1-18 was increased more than 2 times compared to that of the vehicle, and that the concentration was the highest at 8 hours and then gradually decreased (FIG. 11 in (a)).

Meanwhile, the total T4 concentration measured at 8 hours and 24 hours after administration of TR-GS (144 μg/head (7.2 mg/kg)) showed no change compared to the vehicle (FIG. 11 in (b)). Accordingly, the increase of total T4 concentration in mouse blood was found to be due to K1-18 (thyrotropin receptor autoantibody), without being directly affected by TR-GS, the fusion protein.

As a result of identification of the autoantibody neutralization effect by TR-GS through measurement of total T4 8 hours after K1-18 administration, K1-18 administration group was observed to increase the total T4 by 2.5 times or more (one-way ANOVA, $p<0.01$), compared to the vehicle, whereas TR-GS reduced the total T4 at two concentrations; in particular, TR-GS reduced the total T4 to a level similar to the vehicle when administered with 144 μg/head (7.2 mg/kg) of TR-GS (one-way ANOVA, $p<0.01$) (FIG. 11 in (c)). This indicates that the thyroid-stimulating effect resulting from the thyrotropin receptor autoantibody can be eliminated or reduced by the fusion protein.

Experimental Example 5. Measurement of Thyrotropin Receptor Autoantibody Using Fusion Protein Experimental Example 5-1. ELISA Measurement Test Method K1-18, a thyrotropin receptor autoantibody, was diluted to 1 μg/mL (or M11 antibody was diluted to 0.1 μg/mL) in 1×PBS and coated on an ELISA plate overnight at 4° C. After washing 4 times with 1×PBST (wash buffer, 0.05% Tween 20 in PBS buffer), the cells were blocked with blocking buffer (3% BSA in 1×PBST buffer) for 2 hours at 25° C. and each well of the Elisa plate was washed three times with a wash buffer. Fusion proteins were each prepared down to a minimum of 1 μg/mL or less from 8 μg/mL through serial 2-fold dilution. The dilution buffer used herein was 1% BSA in PBS buffer. The prepared respective samples were injected at 100 μL into ELISA wells and were incubated at 25° C. for 2 hours such that they were capable of binding to K1-18 (or M22). Then, all wells were washed again three times with wash buffer, and then human IgG4-Fc-HRP (1/2000 dilution buffer) was prepared, injected at 100 μL into wells and incubated at 25° C. for 1 hour. After washing three times with wash buffer, a TMB solution [TMB detection reagent (Bio-Rad, 172-1066)] was prepared, injected at 100 μL into ELISA wells and incubated at 25° C. for 8 minutes. In order to complete the color development, 100 μL of a stop solution (1M $H_2SO_4$) was added to each well to complete the entire color reaction. Then, the ELISA plate was transferred to a measurement instrument (Perkin Elmer Wallac Victor3 1420 multilabel counter) and absorbance at 450 nm was measured.

The results showed that the concentration of the autoantibody in the sample can be determined by quantitative measurement and thus can be used for the diagnosis of diseases.

Experimental Example 5-2. Method of ELISA Measurement Using Patient Blood and Fusion Protein The total amount of thyrotropin receptor autoantibody present in a patient's blood can be measured by coating the patient's blood on ELISA, instead of K1-18 (or M22), and using the fusion protein. It was found that, using the method comprising directly binding a small fluorescent molecule (e.g., Alexa Fluor 450) to the fusion protein and measuring the fluorescence of the small fluorescent molecule without treatment with a secondarily used antibody for measurement (human IgG4-Fc-HRP), the total amount of autoantibody in the patient's blood could be measured and be then used for the diagnosis of diseases.

Experimental Example 5-3. Measurement Method Using Protein G/A Bead

In the case of the fusion protein, TR-C-Cap, the desired tag (e.g., His-tag, flag tag) sequence can be added to the C-terminus of the protein. The TR-C-Cap fusion protein can be directly bound using a bead (e.g., a His-tag bead) to which this tag can bind, the thyrotropin receptor autoantibodies in the blood can be directly bound thereto, and the total amount thereof can be measured. The TR-C-Cap bound to the bead binds to the Fab region of the autoantibody and binds to an antibody (e.g., human IgG-Fc-HRP, human IgG-Fc-Alexa450) capable of recognizing the externally exposed Fc region, thus making measurement possible.

Experimental Example 6. Comparison of Performance Between Fusion Protein Fragments The neutralizing effects of the Fc fusion protein of the known TSHR fragment and the Fc fusion protein of the TSHR fragment developed in the present invention were measured using the Thyretain TSI assay kit.

As a result, as can be seen from FIG. 15 in (A), T20 in which Fc was fused to TSHR21-288 protein similar to known TSHR21-289 protein had no autoantibody-neutralizing effect at a concentration of 5 μg/ml, whereas TR-GS in which Fc was fused with the TSHR21-282 fragment developed in the present invention had a remarkable autoantibody-neutralizing effect even at 5 μg/ml.

Furthermore, it was found that even the fusion proteins in which Fc was fused to TSHR1-260 (T27), TSRH21-262 (T51) and TSHR21-260 (T60) protein fragments similar to known TSHR21-261 (FIG. 15 in (B)) had no autoantibody-neutralizing effect (FIG. 15 in (B)).

Although specific configurations of the present invention have been described in detail, those skilled in the art will appreciate that this detailed description is provided as preferred embodiments and should not be construed as limiting the scope of the present invention. Therefore, the substantial scope of the present invention is defined by the accompanying filed claims and equivalents thereto.

INDUSTRIAL APPLICABILITY

It was found that the fusion protein comprising a TSHR fragment according to the present invention does not bind to thyroid-stimulating hormone (TSH), maintains the binding with thyrotropin receptor autoantibodies, and exhibits improved productivity and in-vivo persistence, as well as enhanced thermostability at 37° C. The pharmaceutical composition containing the fusion protein comprising the TSHR fragment can be used as a diagnostic and therapeutic agent for Graves' disease.

The invention claimed is:

1. A fusion protein comprising an immunoglobulin Fc region comprising the sequence of SEQ ID NO: 22 or a carboxyl terminal cap (C-CAP) comprising any one amino acid sequence selected from the group consisting of SEQ ID NOS: 23 to 28 bound to the following thyrotropin receptor (TSHR) fragment:
   (i) a fragment from amino acid at position 21 to amino acid at position 282 of a TSHR represented by an amino acid sequence of SEQ ID NO: 1; or
   (ii) a fragment from amino acid at position 21 to amino acid at position 266 of the TSHR represented by the amino acid sequence of SEQ ID NO: 1.

2. The fusion protein according to claim 1, wherein the TSHR fragment is bound to the immunoglobulin Fc region via a linker represented by any one selected from the group consisting of SEQ ID NOS: 17 to 21.

3. The fusion protein according to claim 1, wherein the fusion protein comprises an amino acid sequence represented by SEQ ID NO: 29 or 30.

4. A nucleic acid encoding a fusion protein comprising an immunoglobulin Fc region comprising the sequence of SEQ ID NO: 22 or a carboxyl terminal cap (C-CAP) comprising any one amino acid sequence selected from the group consisting of SEQ ID NOS: 23 to 28 bound to the following thyrotropin receptor (TSHR) fragment:
   (i) a fragment from amino acid at position 21 to amino acid at position 282 of a TSHR represented by an amino acid sequence of SEQ ID NO: 1; or
   (ii) a fragment from amino acid at position 21 to amino acid at position 266 of the TSHR represented by the amino acid sequence of SEQ ID NO: 1.

5. A recombinant vector comprising the nucleic acid according to claim 4.

6. A recombinant cell introduced with the recombinant vector according to claim 5.

7. A method for producing a fusion protein comprising an immunoglobulin Fc region or a carboxyl terminal cap (C-CAP) bound to a thyrotropin receptor (TSHR) fragment, the method comprising:
   (a) culturing the recombinant cell according to claim 6 to express the fusion protein; and
   (b) recovering the expressed fusion protein.

8. A pharmaceutical composition for treating or preventing Graves' disease comprising the fusion protein according to claim 1.

9. A composition for diagnosing Graves' disease comprising the fusion protein according to claim 1.

* * * * *

SEQUENCE LISTING

```
<160> NUMBER OF SEQ ID NOS: 39

<210> SEQ ID NO 1
<211> LENGTH: 764
<212> TYPE: PRT
<213> ORGANISM: Artificial Sequence
<220> FEATURE:
<223> OTHER INFORMATION: Synthetic Construct

<400> SEQUENCE: 1

Met Arg Pro Ala Asp Leu Leu Gln Leu Val Leu Leu Leu Asp Leu Pro
1               5                   10                  15

Arg Asp Leu Gly Gly Met Gly Cys Ser Ser Pro Pro Cys Glu Cys His
                20                  25                  30

Gln Glu Glu Asp Phe Arg Val Thr Cys Lys Asp Ile Gln Arg Ile Pro
            35                  40                  45

Ser Leu Pro Pro Ser Thr Gln Thr Leu Lys Leu Ile Glu Thr His Leu
    50                  55                  60

Arg Thr Ile Pro Ser His Ala Phe Ser Asn Leu Pro Asn Ile Ser Arg
65                  70                  75                  80

Ile Tyr Val Ser Ile Asp Val Thr Leu Gln Gln Leu Glu Ser His Ser
                85                  90                  95

Phe Tyr Asn Leu Ser Lys Val Thr His Ile Glu Ile Arg Asn Thr Arg
            100                 105                 110

Asn Leu Thr Tyr Ile Asp Pro Asp Ala Leu Lys Glu Leu Pro Leu Leu
        115                 120                 125

Lys Phe Leu Gly Ile Phe Asn Thr Gly Leu Lys Met Phe Pro Asp Leu
    130                 135                 140

Thr Lys Val Tyr Ser Thr Asp Ile Phe Phe Ile Leu Glu Ile Thr Asp
145                 150                 155                 160

Asn Pro Tyr Met Thr Ser Ile Pro Val Asn Ala Phe Gln Gly Leu Cys
                165                 170                 175

Asn Glu Thr Leu Thr Leu Lys Leu Tyr Asn Asn Gly Phe Thr Ser Val
            180                 185                 190

Gln Gly Tyr Ala Phe Asn Gly Thr Lys Leu Asp Ala Val Tyr Leu Asn
        195                 200                 205

Lys Asn Lys Tyr Leu Thr Val Ile Asp Lys Asp Ala Phe Gly Gly Val
    210                 215                 220

Tyr Ser Gly Pro Ser Leu Leu Asp Val Ser Gln Thr Ser Val Thr Ala
225                 230                 235                 240

Leu Pro Ser Lys Gly Leu Glu His Leu Lys Glu Leu Ile Ala Arg Asn
                245                 250                 255

Thr Trp Thr Leu Lys Lys Leu Pro Leu Ser Leu Ser Phe Leu His Leu
            260                 265                 270

Thr Arg Ala Asp Leu Ser Tyr Pro Ser His Cys Cys Ala Phe Lys Asn
        275                 280                 285

Gln Lys Lys Ile Arg Gly Ile Leu Glu Ser Leu Met Cys Asn Glu Ser
    290                 295                 300

Ser Met Gln Ser Leu Arg Gln Arg Lys Ser Val Asn Ala Leu Asn Ser
305                 310                 315                 320

Pro Leu His Gln Glu Tyr Glu Glu Asn Leu Gly Asp Ser Ile Val Gly
```

-continued

```
                    325                 330                 335
Tyr Lys Glu Lys Ser Lys Phe Gln Asp Thr His Asn Asn Ala His Tyr
                340                 345                 350
Tyr Val Phe Phe Glu Glu Gln Glu Asp Glu Ile Ile Gly Phe Gly Gln
                355                 360                 365
Glu Leu Lys Asn Pro Gln Glu Thr Leu Gln Ala Phe Asp Ser His
                370                 375                 380
Tyr Asp Tyr Thr Ile Cys Gly Asp Ser Glu Asp Met Val Cys Thr Pro
385                 390                 395                 400
Lys Ser Asp Glu Phe Asn Pro Cys Glu Asp Ile Met Gly Tyr Lys Phe
                405                 410                 415
Leu Arg Ile Val Val Trp Phe Val Ser Leu Leu Ala Leu Leu Gly Asn
                420                 425                 430
Val Phe Val Leu Leu Ile Leu Leu Thr Ser His Tyr Lys Leu Asn Val
                435                 440                 445
Pro Arg Phe Leu Met Cys Asn Leu Ala Phe Ala Asp Phe Cys Met Gly
                450                 455                 460
Met Tyr Leu Leu Leu Ile Ala Ser Val Asp Leu Tyr Thr His Ser Glu
465                 470                 475                 480
Tyr Tyr Asn His Ala Ile Asp Trp Gln Thr Gly Pro Gly Cys Asn Thr
                485                 490                 495
Ala Gly Phe Phe Thr Val Phe Ala Ser Glu Leu Ser Val Tyr Thr Leu
                500                 505                 510
Thr Val Ile Thr Leu Glu Arg Trp Tyr Ala Ile Thr Phe Ala Met Arg
                515                 520                 525
Leu Asp Arg Lys Ile Arg Leu Arg His Ala Cys Ala Ile Met Val Gly
                530                 535                 540
Gly Trp Val Cys Cys Phe Leu Leu Ala Leu Leu Pro Leu Val Gly Ile
545                 550                 555                 560
Ser Ser Tyr Ala Lys Val Ser Ile Cys Leu Pro Met Asp Thr Glu Thr
                565                 570                 575
Pro Leu Ala Leu Ala Tyr Ile Val Phe Val Leu Thr Leu Asn Ile Val
                580                 585                 590
Ala Phe Val Ile Val Cys Cys Cys Tyr Val Lys Ile Tyr Ile Thr Val
                595                 600                 605
Arg Asn Pro Gln Tyr Asn Pro Gly Asp Lys Asp Thr Lys Ile Ala Lys
                610                 615                 620
Arg Met Ala Val Leu Ile Phe Thr Asp Phe Ile Cys Met Ala Pro Ile
625                 630                 635                 640
Ser Phe Tyr Ala Leu Ser Ala Ile Leu Asn Lys Pro Leu Ile Thr Val
                645                 650                 655
Ser Asn Ser Lys Ile Leu Leu Val Leu Phe Tyr Pro Leu Asn Ser Cys
                660                 665                 670
Ala Asn Pro Phe Leu Tyr Ala Ile Phe Thr Lys Ala Phe Gln Arg Asp
                675                 680                 685
Val Phe Ile Leu Leu Ser Lys Phe Gly Ile Cys Lys Arg Gln Ala Gln
                690                 695                 700
Ala Tyr Arg Gly Gln Arg Val Pro Pro Lys Asn Ser Thr Asp Ile Gln
705                 710                 715                 720
Val Gln Lys Val Thr His Asp Met Arg Gln Gly Leu His Asn Met Glu
                725                 730                 735
Asp Val Tyr Glu Leu Ile Glu Asn Ser His Leu Thr Pro Lys Lys Gln
                740                 745                 750
```

Gly Gln Ile Ser Glu Glu Tyr Met Gln Thr Val Leu
          755                 760

<210> SEQ ID NO 2
<211> LENGTH: 397
<212> TYPE: PRT
<213> ORGANISM: Artificial Sequence
<220> FEATURE:
<223> OTHER INFORMATION: Synthetic Construct

<400> SEQUENCE: 2

Gly Met Gly Cys Ser Ser Pro Pro Cys Glu Cys His Gln Glu Glu Asp
1               5                   10                  15

Phe Arg Val Thr Cys Lys Asp Ile Gln Arg Ile Pro Ser Leu Pro Pro
            20                  25                  30

Ser Thr Gln Thr Leu Lys Leu Ile Glu Thr His Leu Arg Thr Ile Pro
        35                  40                  45

Ser His Ala Phe Ser Asn Leu Pro Asn Ile Ser Arg Ile Tyr Val Ser
    50                  55                  60

Ile Asp Val Thr Leu Gln Gln Leu Glu Ser His Ser Phe Tyr Asn Leu
65                  70                  75                  80

Ser Lys Val Thr His Ile Glu Ile Arg Asn Thr Arg Asn Leu Thr Tyr
                85                  90                  95

Ile Asp Pro Asp Ala Leu Lys Glu Leu Pro Leu Leu Lys Phe Leu Gly
            100                 105                 110

Ile Phe Asn Thr Gly Leu Lys Met Phe Pro Asp Leu Thr Lys Val Tyr
        115                 120                 125

Ser Thr Asp Ile Phe Phe Ile Leu Glu Ile Thr Asp Asn Pro Tyr Met
    130                 135                 140

Thr Ser Ile Pro Val Asn Ala Phe Gln Gly Leu Cys Asn Glu Thr Leu
145                 150                 155                 160

Thr Leu Lys Leu Tyr Asn Asn Gly Phe Thr Ser Val Gln Gly Tyr Ala
                165                 170                 175

Phe Asn Gly Thr Lys Leu Asp Ala Val Tyr Leu Asn Lys Asn Lys Tyr
            180                 185                 190

Leu Thr Val Ile Asp Lys Asp Ala Phe Gly Gly Val Tyr Ser Gly Pro
        195                 200                 205

Ser Leu Leu Asp Val Ser Gln Thr Ser Val Thr Ala Leu Pro Ser Lys
    210                 215                 220

Gly Leu Glu His Leu Lys Glu Leu Ile Ala Arg Asn Thr Trp Thr Leu
225                 230                 235                 240

Lys Lys Leu Pro Leu Ser Leu Ser Phe Leu His Leu Thr Arg Ala Asp
                245                 250                 255

Leu Ser Tyr Pro Ser His Cys Cys Ala Phe Lys Asn Gln Lys Lys Ile
            260                 265                 270

Arg Gly Ile Leu Glu Ser Leu Met Cys Asn Glu Ser Ser Met Gln Ser
        275                 280                 285

Leu Arg Gln Arg Lys Ser Val Asn Ala Leu Asn Ser Pro Leu His Gln
    290                 295                 300

Glu Tyr Glu Glu Asn Leu Gly Asp Ser Ile Val Gly Tyr Lys Glu Lys
305                 310                 315                 320

Ser Lys Phe Gln Asp Thr His Asn Asn Ala His Tyr Tyr Val Phe Phe
                325                 330                 335

Glu Glu Gln Glu Asp Glu Ile Ile Gly Phe Gly Gln Glu Leu Lys Asn
            340                 345                 350

```
Pro Gln Glu Glu Thr Leu Gln Ala Phe Asp Ser His Tyr Asp Tyr Thr
        355                 360                 365

Ile Cys Gly Asp Ser Glu Asp Met Val Cys Thr Pro Lys Ser Asp Glu
    370                 375                 380

Phe Asn Pro Cys Glu Asp Ile Met Gly Tyr Lys Phe Leu
385             390                 395

<210> SEQ ID NO 3
<211> LENGTH: 388
<212> TYPE: PRT
<213> ORGANISM: Artificial Sequence
<220> FEATURE:
<223> OTHER INFORMATION: Synthetic Construct

<400> SEQUENCE: 3

Gly Met Gly Cys Ser Ser Pro Cys Glu Cys His Gln Glu Glu Asp
1               5                   10                  15

Phe Arg Val Thr Cys Lys Asp Ile Gln Arg Ile Pro Ser Leu Pro Pro
            20                  25                  30

Ser Thr Gln Thr Leu Lys Leu Ile Glu Thr His Leu Arg Thr Ile Pro
        35                  40                  45

Ser His Ala Phe Ser Asn Leu Pro Asn Ile Ser Arg Ile Tyr Val Ser
    50                  55                  60

Ile Asp Val Thr Leu Gln Gln Leu Glu Ser His Ser Phe Tyr Asn Leu
65                  70                  75                  80

Ser Lys Val Thr His Ile Glu Ile Arg Asn Thr Arg Asn Leu Thr Tyr
            85                  90                  95

Ile Asp Pro Asp Ala Leu Lys Glu Leu Pro Leu Leu Lys Phe Leu Gly
            100                 105                 110

Ile Phe Asn Thr Gly Leu Lys Met Phe Pro Asp Leu Thr Lys Val Tyr
        115                 120                 125

Ser Thr Asp Ile Phe Phe Ile Leu Glu Ile Thr Asp Asn Pro Tyr Met
    130                 135                 140

Thr Ser Ile Pro Val Asn Ala Phe Gln Gly Leu Cys Asn Glu Thr Leu
145                 150                 155                 160

Thr Leu Lys Leu Tyr Asn Asn Gly Phe Thr Ser Val Gln Gly Tyr Ala
                165                 170                 175

Phe Asn Gly Thr Lys Leu Asp Ala Val Tyr Leu Asn Lys Asn Lys Tyr
            180                 185                 190

Leu Thr Val Ile Asp Lys Asp Ala Phe Gly Gly Val Tyr Ser Gly Pro
        195                 200                 205

Ser Leu Leu Asp Val Ser Gln Thr Ser Val Thr Ala Leu Pro Ser Lys
    210                 215                 220

Gly Leu Glu His Leu Lys Glu Leu Ile Ala Arg Asn Thr Trp Thr Leu
225                 230                 235                 240

Lys Lys Leu Pro Leu Ser Leu Ser Phe Leu His Leu Thr Arg Ala Asp
                245                 250                 255

Leu Ser Tyr Pro Ser His Cys Cys Ala Phe Lys Asn Gln Lys Lys Ile
            260                 265                 270

Arg Gly Ile Leu Glu Ser Leu Met Cys Asn Glu Ser Ser Met Gln Ser
        275                 280                 285

Leu Arg Gln Arg Lys Ser Val Asn Ala Leu Asn Ser Pro Leu His Gln
    290                 295                 300

Glu Tyr Glu Glu Asn Leu Gly Asp Ser Ile Val Gly Tyr Lys Glu Lys
305                 310                 315                 320
```

-continued

Ser Lys Phe Gln Asp Thr His Asn Asn Ala His Tyr Tyr Val Phe Phe
            325                 330                 335

Glu Glu Gln Glu Asp Glu Ile Ile Gly Phe Gly Thr Leu Gln Ala Phe
            340                 345                 350

Asp Ser His Tyr Asp Tyr Thr Ile Cys Gly Asp Ser Glu Asp Met Val
            355                 360                 365

Cys Thr Pro Lys Ser Asp Glu Phe Asn Pro Cys Glu Asp Ile Met Gly
            370                 375                 380

Tyr Lys Phe Leu
385

<210> SEQ ID NO 4
<211> LENGTH: 388
<212> TYPE: PRT
<213> ORGANISM: Artificial Sequence
<220> FEATURE:
<223> OTHER INFORMATION: Synthetic Construct

<400> SEQUENCE: 4

Gly Met Gly Cys Ser Ser Pro Pro Cys Glu Cys His Gln Glu Glu Asp
1               5                   10                  15

Phe Arg Val Thr Cys Lys Asp Ile Gln Arg Ile Pro Ser Leu Pro Pro
                20                  25                  30

Ser Thr Gln Thr Leu Lys Leu Ile Glu Thr His Leu Arg Thr Ile Pro
        35                  40                  45

Ser His Ala Phe Ser Asn Leu Pro Asn Ile Ser Arg Ile Tyr Val Ser
    50                  55                  60

Ile Asp Val Thr Leu Gln Gln Leu Glu Ser His Ser Phe Tyr Asn Leu
65                  70                  75                  80

Ser Lys Val Thr His Ile Glu Ile Arg Asn Thr Arg Asn Leu Thr Tyr
                85                  90                  95

Ile Asp Pro Asp Ala Leu Lys Glu Leu Pro Leu Leu Lys Phe Leu Gly
            100                 105                 110

Ile Phe Asn Thr Gly Leu Lys Met Phe Pro Asp Leu Thr Lys Val Tyr
        115                 120                 125

Ser Thr Asp Ile Phe Phe Ile Leu Glu Ile Thr Asp Asn Pro Tyr Met
130                 135                 140

Thr Ser Ile Pro Val Asn Ala Phe Gln Gly Leu Cys Asn Glu Thr Leu
145                 150                 155                 160

Thr Leu Lys Leu Tyr Asn Asn Gly Phe Thr Ser Val Gln Gly Tyr Ala
                165                 170                 175

Phe Asn Gly Thr Lys Leu Asp Ala Val Tyr Leu Asn Lys Asn Lys Tyr
            180                 185                 190

Leu Thr Val Ile Asp Lys Asp Ala Phe Gly Gly Val Tyr Ser Gly Pro
        195                 200                 205

Ser Leu Leu Asp Val Ser Gln Thr Ser Val Thr Ala Leu Pro Ser Lys
210                 215                 220

Gly Leu Glu His Leu Lys Glu Leu Ile Ala Arg Asn Thr Trp Thr Leu
225                 230                 235                 240

Lys Lys Leu Pro Leu Ser Leu Ser Phe Leu His Leu Thr Arg Ala Asp
                245                 250                 255

Leu Ser Tyr Pro Ser His Cys Cys Ala Phe Lys Asn Gln Lys Lys Ile
            260                 265                 270

Arg Gly Ile Leu Glu Ser Leu Met Cys Asn Glu Ser Ser Met Gln Ser
        275                 280                 285

```
Leu Arg Gln Arg Lys Ser Val Asn Ala Leu Asn Ser Pro Leu His Gln
        290                 295                 300

Glu Tyr Glu Glu Asn Leu Gly Asp Ser Ile Val Gly Tyr Lys Glu Lys
305                 310                 315                 320

Ser Lys Phe Gln Asp Thr His Asn Asn Ala His Tyr Tyr Val Phe Phe
                325                 330                 335

Glu Glu Gln Glu Asp Glu Ile Ile Gly Phe Gly Thr Leu Gln Ala Phe
            340                 345                 350

Asp Ser His Tyr Asp Tyr Thr Ile Ser Gly Asp Ser Glu Asp Met Val
        355                 360                 365

Ser Thr Pro Lys Ser Asp Glu Phe Asn Pro Ser Glu Asp Ile Met Gly
    370                 375                 380

Tyr Lys Phe Leu
385

<210> SEQ ID NO 5
<211> LENGTH: 261
<212> TYPE: PRT
<213> ORGANISM: Artificial Sequence
<220> FEATURE:
<223> OTHER INFORMATION: Synthetic Construct

<400> SEQUENCE: 5

Gly Met Gly Cys Ser Ser Pro Pro Cys Glu Cys His Gln Glu Glu Asp
1               5                   10                  15

Phe Arg Val Thr Cys Lys Asp Ile Gln Arg Ile Pro Ser Leu Pro Pro
            20                  25                  30

Ser Thr Gln Thr Leu Lys Leu Ile Glu Thr His Leu Arg Thr Ile Pro
        35                  40                  45

Ser His Ala Phe Ser Asn Leu Pro Asn Ile Ser Arg Ile Tyr Val Ser
    50                  55                  60

Ile Asp Val Thr Leu Gln Gln Leu Glu Ser His Ser Phe Tyr Asn Leu
65                  70                  75                  80

Ser Lys Val Thr His Ile Glu Ile Arg Asn Thr Arg Asn Leu Thr Tyr
                85                  90                  95

Ile Asp Pro Asp Ala Leu Lys Glu Leu Pro Leu Leu Lys Phe Leu Gly
            100                 105                 110

Ile Phe Asn Thr Gly Leu Lys Met Pro Asp Leu Thr Lys Val Tyr Ser
        115                 120                 125

Thr Asp Ile Phe Phe Ile Leu Glu Ile Thr Asp Asn Pro Tyr Met Thr
130                 135                 140

Ser Ile Pro Val Asn Ala Phe Gln Gly Leu Cys Asn Glu Thr Leu Thr
145                 150                 155                 160

Leu Lys Leu Tyr Asn Asn Gly Phe Thr Ser Val Gln Gly Tyr Ala Phe
                165                 170                 175

Asn Gly Thr Lys Leu Asp Ala Val Tyr Leu Asn Lys Asn Lys Tyr Leu
            180                 185                 190

Thr Val Ile Asp Lys Asp Ala Phe Gly Gly Val Tyr Ser Gly Pro Ser
        195                 200                 205

Leu Leu Asp Val Ser Gln Thr Ser Val Thr Ala Leu Pro Ser Lys Gly
    210                 215                 220

Leu Glu His Leu Lys Glu Leu Ile Ala Arg Asn Thr Trp Thr Leu Lys
225                 230                 235                 240

Lys Leu Pro Leu Ser Leu Ser Phe Leu His Leu Thr Arg Ala Asp Leu
                245                 250                 255
```

-continued

Ser Tyr Pro Ser His
              260

<210> SEQ ID NO 6
<211> LENGTH: 246
<212> TYPE: PRT
<213> ORGANISM: Artificial Sequence
<220> FEATURE:
<223> OTHER INFORMATION: Synthetic Construct

<400> SEQUENCE: 6

Gly Met Gly Cys Ser Ser Pro Pro Cys Glu Cys His Gln Glu Glu Asp
1               5                   10                  15

Phe Arg Val Thr Cys Lys Asp Ile Gln Arg Ile Pro Ser Leu Pro Pro
            20                  25                  30

Ser Thr Gln Thr Leu Lys Leu Ile Glu Thr His Leu Arg Thr Ile Pro
        35                  40                  45

Ser His Ala Phe Ser Asn Leu Pro Asn Ile Ser Arg Ile Tyr Val Ser
    50                  55                  60

Ile Asp Val Thr Leu Gln Gln Leu Glu Ser His Ser Phe Tyr Asn Leu
65                  70                  75                  80

Ser Lys Val Thr His Ile Glu Ile Arg Asn Thr Arg Asn Leu Thr Tyr
                85                  90                  95

Ile Asp Pro Asp Ala Leu Lys Glu Leu Pro Leu Leu Lys Phe Leu Gly
            100                 105                 110

Ile Phe Asn Thr Gly Leu Lys Met Phe Pro Asp Leu Thr Lys Val Tyr
        115                 120                 125

Ser Thr Asp Ile Phe Phe Ile Leu Glu Ile Thr Asp Asn Pro Tyr Met
    130                 135                 140

Thr Ser Ile Pro Val Asn Ala Phe Gln Gly Leu Cys Asn Glu Thr Leu
145                 150                 155                 160

Thr Leu Lys Leu Tyr Asn Asn Gly Phe Thr Ser Val Gln Gly Tyr Ala
                165                 170                 175

Phe Asn Gly Thr Lys Leu Asp Ala Val Tyr Leu Asn Lys Asn Lys Tyr
            180                 185                 190

Leu Thr Val Ile Asp Lys Asp Ala Phe Gly Gly Val Tyr Ser Gly Pro
        195                 200                 205

Ser Leu Leu Asp Val Ser Gln Thr Ser Val Thr Ala Leu Pro Ser Lys
    210                 215                 220

Gly Leu Glu His Leu Lys Glu Leu Ile Ala Arg Asn Thr Trp Thr Leu
225                 230                 235                 240

Lys Lys Leu Pro Leu Ser
                245

<210> SEQ ID NO 7
<211> LENGTH: 211
<212> TYPE: PRT
<213> ORGANISM: Artificial Sequence
<220> FEATURE:
<223> OTHER INFORMATION: Synthetic Construct

<400> SEQUENCE: 7

Gly Met Gly Cys Ser Ser Pro Pro Cys Glu Cys His Gln Glu Glu Asp
1               5                   10                  15

Phe Arg Val Thr Cys Lys Asp Ile Gln Arg Ile Pro Ser Leu Pro Pro
            20                  25                  30

Ser Thr Gln Thr Leu Lys Leu Ile Glu Thr His Leu Arg Thr Ile Pro

```
              35                  40                  45
Ser His Ala Phe Ser Asn Leu Pro Asn Ile Ser Arg Ile Tyr Val Ser
 50                  55                  60

Ile Asp Val Thr Leu Gln Gln Leu Glu Ser His Ser Phe Tyr Asn Leu
 65                  70                  75                  80

Ser Lys Val Thr His Ile Glu Ile Arg Asn Thr Arg Asn Leu Thr Tyr
                 85                  90                  95

Ile Asp Pro Asp Ala Leu Lys Glu Leu Pro Leu Leu Lys Phe Leu Gly
                100                 105                 110

Ile Phe Asn Thr Gly Leu Lys Met Phe Pro Asp Leu Thr Lys Val Tyr
                115                 120                 125

Ser Thr Asp Ile Phe Phe Ile Leu Glu Ile Thr Asp Asn Pro Tyr Met
130                 135                 140

Thr Ser Ile Pro Val Asn Ala Phe Gln Gly Leu Cys Asn Glu Thr Leu
145                 150                 155                 160

Thr Leu Lys Leu Tyr Asn Asn Gly Phe Thr Ser Val Gln Gly Tyr Ala
                165                 170                 175

Phe Asn Gly Thr Lys Leu Asp Ala Val Tyr Leu Asn Lys Asn Lys Tyr
                180                 185                 190

Leu Thr Val Ile Asp Lys Asp Ala Phe Gly Gly Val Tyr Ser Gly Pro
                195                 200                 205

Ser Leu Leu
    210

<210> SEQ ID NO 8
<211> LENGTH: 186
<212> TYPE: PRT
<213> ORGANISM: Artificial Sequence
<220> FEATURE:
<223> OTHER INFORMATION: Synthetic Construct

<400> SEQUENCE: 8

Gly Met Gly Cys Ser Ser Pro Pro Cys Glu Cys His Gln Glu Glu Asp
 1               5                  10                  15

Phe Arg Val Thr Cys Lys Asp Ile Gln Arg Ile Pro Ser Leu Pro Pro
                20                  25                  30

Ser Thr Gln Thr Leu Lys Leu Ile Glu Thr His Leu Arg Thr Ile Pro
                35                  40                  45

Ser His Ala Phe Ser Asn Leu Pro Asn Ile Ser Arg Ile Tyr Val Ser
 50                  55                  60

Ile Asp Val Thr Leu Gln Gln Leu Glu Ser His Ser Phe Tyr Asn Leu
 65                  70                  75                  80

Ser Lys Val Thr His Ile Glu Ile Arg Asn Thr Arg Asn Leu Thr Tyr
                 85                  90                  95

Ile Asp Pro Asp Ala Leu Lys Glu Leu Pro Leu Leu Lys Phe Leu Gly
                100                 105                 110

Ile Phe Asn Thr Gly Leu Lys Met Phe Pro Asp Leu Thr Lys Val Tyr
                115                 120                 125

Ser Thr Asp Ile Phe Phe Ile Leu Glu Ile Thr Asp Asn Pro Tyr Met
130                 135                 140

Thr Ser Ile Pro Val Asn Ala Phe Gln Gly Leu Cys Asn Glu Thr Leu
145                 150                 155                 160

Thr Leu Lys Leu Tyr Asn Asn Gly Phe Thr Ser Val Gln Gly Tyr Ala
                165                 170                 175

Phe Asn Gly Thr Lys Leu Asp Ala Val Tyr
```

-continued

<210> SEQ ID NO 9
<211> LENGTH: 136
<212> TYPE: PRT
<213> ORGANISM: Artificial Sequence
<220> FEATURE:
<223> OTHER INFORMATION: Synthetic Construct

<400> SEQUENCE: 9

Gly Met Gly Cys Ser Ser Pro Pro Cys Glu Cys His Gln Glu Glu Asp
1               5                   10                  15

Phe Arg Val Thr Cys Lys Asp Ile Gln Arg Ile Pro Ser Leu Pro Pro
            20                  25                  30

Ser Thr Gln Thr Leu Lys Leu Ile Glu Thr His Leu Arg Thr Ile Pro
        35                  40                  45

Ser His Ala Phe Ser Asn Leu Pro Asn Ile Ser Arg Ile Tyr Val Ser
    50                  55                  60

Ile Asp Val Thr Leu Gln Gln Leu Glu Ser His Ser Phe Tyr Asn Leu
65                  70                  75                  80

Ser Lys Val Thr His Ile Glu Ile Arg Asn Thr Arg Asn Leu Thr Tyr
                85                  90                  95

Ile Asp Pro Asp Ala Leu Lys Glu Leu Pro Leu Leu Lys Phe Leu Gly
            100                 105                 110

Ile Phe Asn Thr Gly Leu Lys Met Phe Pro Asp Leu Thr Lys Val Tyr
        115                 120                 125

Ser Thr Asp Ile Phe Phe Ile Leu
    130                 135

<210> SEQ ID NO 10
<211> LENGTH: 107
<212> TYPE: PRT
<213> ORGANISM: Artificial Sequence
<220> FEATURE:
<223> OTHER INFORMATION: Synthetic Construct

<400> SEQUENCE: 10

Gly Met Gly Cys Ser Ser Pro Pro Cys Glu Cys His Gln Glu Glu Asp
1               5                   10                  15

Phe Arg Val Thr Cys Lys Asp Ile Gln Arg Ile Pro Ser Leu Pro Pro
            20                  25                  30

Ser Thr Gln Thr Leu Lys Leu Ile Glu Thr His Leu Arg Thr Ile Pro
        35                  40                  45

Ser His Ala Phe Ser Asn Leu Pro Asn Ile Ser Arg Ile Tyr Val Ser
    50                  55                  60

Ile Asp Val Thr Leu Gln Gln Leu Glu Ser His Ser Phe Tyr Asn Leu
65                  70                  75                  80

Ser Lys Val Thr His Ile Glu Ile Arg Asn Thr Arg Asn Leu Thr Tyr
                85                  90                  95

Ile Asp Pro Asp Ala Leu Lys Glu Leu Pro Leu
            100                 105

<210> SEQ ID NO 11
<211> LENGTH: 138
<212> TYPE: PRT
<213> ORGANISM: Artificial Sequence
<220> FEATURE:
<223> OTHER INFORMATION: Synthetic Construct

<400> SEQUENCE: 11

```
Glu Ile Thr Asp Asn Pro Tyr Met Thr Ser Ile Pro Val Asn Ala Phe
1               5                   10                  15

Gln Gly Leu Cys Asn Glu Thr Leu Thr Leu Lys Leu Tyr Asn Asn Gly
            20                  25                  30

Phe Thr Ser Val Gln Gly Tyr Ala Phe Asn Gly Thr Lys Leu Asp Ala
        35                  40                  45

Val Tyr Leu Asn Lys Asn Lys Tyr Leu Thr Val Ile Asp Lys Asp Ala
    50                  55                  60

Phe Gly Gly Val Tyr Ser Gly Pro Ser Leu Leu Asp Val Ser Gln Thr
65                  70                  75                  80

Ser Val Thr Ala Leu Pro Ser Lys Gly Leu Glu His Leu Lys Glu Leu
                85                  90                  95

Ile Ala Arg Asn Thr Trp Thr Leu Lys Lys Leu Pro Leu Ser Leu Ser
            100                 105                 110

Phe Leu His Leu Thr Arg Ala Asp Leu Ser Tyr Pro Ser His Cys Cys
        115                 120                 125

Ala Phe Lys Asn Gln Lys Lys Ile Arg Gly
    130                 135
```

<210> SEQ ID NO 12
<211> LENGTH: 261
<212> TYPE: PRT
<213> ORGANISM: Artificial Sequence
<220> FEATURE:
<223> OTHER INFORMATION: Synthetic Construct

<400> SEQUENCE: 12

```
Gly Met Gly Cys Ser Ser Pro Pro Cys Glu Cys His Gln Glu Glu Asp
1               5                   10                  15

Phe Arg Val Thr Cys Lys Ala Ile Gln Arg Ile Pro Ser Leu Pro Pro
            20                  25                  30

Ser Thr Gln Thr Leu Lys Leu Ile Glu Thr His Leu Arg Thr Ile Pro
        35                  40                  45

Ser His Ala Phe Ser Asn Leu Pro Asn Ile Ser Arg Ile Tyr Val Ser
    50                  55                  60

Ile Asp Val Thr Leu Gln Gln Leu Glu Ser His Ser Phe Tyr Asn Leu
65                  70                  75                  80

Ser Lys Val Thr His Ile Glu Ile Arg Asn Thr Arg Asn Leu Thr Tyr
                85                  90                  95

Ile Asp Pro Asp Ala Leu Lys Glu Leu Pro Leu Leu Lys Phe Leu Gly
            100                 105                 110

Ile Phe Asn Thr Gly Leu Lys Met Pro Asp Leu Thr Lys Val Tyr Ser
        115                 120                 125

Thr Asp Ile Phe Phe Ile Leu Glu Ile Thr Asp Asn Pro Tyr Met Thr
    130                 135                 140

Ser Ile Pro Val Asn Ala Phe Gln Gly Leu Cys Asn Glu Thr Leu Thr
145                 150                 155                 160

Leu Lys Leu Tyr Asn Asn Gly Phe Thr Ser Val Gln Gly Tyr Ala Phe
                165                 170                 175

Asn Gly Thr Lys Leu Asp Ala Val Tyr Leu Asn Lys Asn Lys Tyr Leu
            180                 185                 190

Thr Val Ile Asp Lys Asp Ala Phe Gly Gly Val Tyr Ser Gly Pro Ser
        195                 200                 205

Leu Leu Asp Val Ser Gln Thr Ser Val Thr Ala Leu Pro Ser Lys Gly
    210                 215                 220
```

Leu Glu His Leu Lys Glu Leu Ile Ala Arg Asn Thr Trp Thr Leu Lys
225                 230                 235                 240

Lys Leu Pro Leu Ser Leu Ser Phe Leu His Leu Thr Arg Ala Asp Leu
            245                 250                 255

Ser Tyr Pro Ser His
            260

<210> SEQ ID NO 13
<211> LENGTH: 261
<212> TYPE: PRT
<213> ORGANISM: Artificial Sequence
<220> FEATURE:
<223> OTHER INFORMATION: Synthetic Construct

<400> SEQUENCE: 13

Gly Met Gly Cys Ser Ser Pro Pro Cys Glu Cys His Gln Glu Glu Asp
1               5                   10                  15

Phe Arg Val Thr Cys Lys Asp Ile Gln Arg Ile Pro Ser Leu Pro Pro
            20                  25                  30

Ser Thr Gln Thr Leu Lys Leu Ile Ala Thr His Leu Arg Thr Ile Pro
        35                  40                  45

Ser His Ala Phe Ser Asn Leu Pro Asn Ile Ser Arg Ile Tyr Val Ser
    50                  55                  60

Ile Asp Val Thr Leu Gln Gln Leu Glu Ser His Ser Phe Tyr Asn Leu
65                  70                  75                  80

Ser Lys Val Thr His Ile Glu Ile Arg Asn Thr Arg Asn Leu Thr Tyr
                85                  90                  95

Ile Asp Pro Asp Ala Leu Lys Glu Leu Pro Leu Leu Lys Phe Leu Gly
            100                 105                 110

Ile Phe Asn Thr Gly Leu Lys Met Pro Asp Leu Thr Lys Val Tyr Ser
        115                 120                 125

Thr Asp Ile Phe Phe Ile Leu Glu Ile Thr Asp Asn Pro Tyr Met Thr
    130                 135                 140

Ser Ile Pro Val Asn Ala Phe Gln Gly Leu Cys Asn Glu Thr Leu Thr
145                 150                 155                 160

Leu Lys Leu Tyr Asn Asn Gly Phe Thr Ser Val Gln Gly Tyr Ala Phe
                165                 170                 175

Asn Gly Thr Lys Leu Asp Ala Val Tyr Leu Asn Lys Asn Lys Tyr Leu
            180                 185                 190

Thr Val Ile Asp Lys Asp Ala Phe Gly Gly Val Tyr Ser Gly Pro Ser
        195                 200                 205

Leu Leu Asp Val Ser Gln Thr Ser Val Thr Ala Leu Pro Ser Lys Gly
210                 215                 220

Leu Glu His Leu Lys Glu Leu Ile Ala Arg Asn Thr Trp Thr Leu Lys
225                 230                 235                 240

Lys Leu Pro Leu Ser Leu Ser Phe Leu His Leu Thr Arg Ala Asp Leu
            245                 250                 255

Ser Tyr Pro Ser His
            260

<210> SEQ ID NO 14
<211> LENGTH: 261
<212> TYPE: PRT
<213> ORGANISM: Artificial Sequence
<220> FEATURE:
<223> OTHER INFORMATION: Synthetic Construct

<400> SEQUENCE: 14

Gly Met Gly Cys Ser Ser Pro Pro Cys Glu Cys His Gln Glu Glu Asp
1               5                   10                  15

Phe Arg Val Thr Cys Lys Ala Ile Gln Arg Ile Pro Ser Leu Pro Pro
                20                  25                  30

Ser Thr Gln Thr Leu Lys Leu Ile Ala Thr His Leu Arg Thr Ile Pro
            35                  40                  45

Ser His Ala Phe Ser Asn Leu Pro Asn Ile Ser Arg Ile Tyr Val Ser
        50                  55                  60

Ile Asp Val Thr Leu Gln Gln Leu Glu Ser His Ser Phe Tyr Asn Leu
65                  70                  75                  80

Ser Lys Val Thr His Ile Glu Ile Arg Asn Thr Arg Asn Leu Thr Tyr
                85                  90                  95

Ile Asp Pro Asp Ala Leu Lys Glu Leu Pro Leu Leu Lys Phe Leu Gly
                100                 105                 110

Ile Phe Asn Thr Gly Leu Lys Met Pro Asp Leu Thr Lys Val Tyr Ser
            115                 120                 125

Thr Asp Ile Phe Phe Ile Leu Glu Ile Thr Asp Asn Pro Tyr Met Thr
        130                 135                 140

Ser Ile Pro Val Asn Ala Phe Gln Gly Leu Cys Asn Glu Thr Leu Thr
145                 150                 155                 160

Leu Lys Leu Tyr Asn Asn Gly Phe Thr Ser Val Gln Gly Tyr Ala Phe
                165                 170                 175

Asn Gly Thr Lys Leu Asp Ala Val Tyr Leu Asn Lys Asn Lys Tyr Leu
                180                 185                 190

Thr Val Ile Asp Lys Asp Ala Phe Gly Gly Val Tyr Ser Gly Pro Ser
            195                 200                 205

Leu Leu Asp Val Ser Gln Thr Ser Val Thr Ala Leu Pro Ser Lys Gly
        210                 215                 220

Leu Glu His Leu Lys Glu Leu Ile Ala Arg Asn Thr Trp Thr Leu Lys
225                 230                 235                 240

Lys Leu Pro Leu Ser Leu Ser Phe Leu His Leu Thr Arg Ala Asp Leu
                245                 250                 255

Ser Tyr Pro Ser His
            260

<210> SEQ ID NO 15
<211> LENGTH: 261
<212> TYPE: PRT
<213> ORGANISM: Artificial Sequence
<220> FEATURE:
<223> OTHER INFORMATION: Synthetic Construct

<400> SEQUENCE: 15

Gly Met Gly Cys Ser Ser Pro Pro Cys Glu Cys His Gln Glu Glu Asp
1               5                   10                  15

Phe Arg Val Thr Cys Lys Asp Ile Gln Arg Ile Pro Ser Leu Pro Pro
                20                  25                  30

Ser Thr Gln Thr Leu Lys Leu Ile Glu Thr His Leu Arg Thr Ile Pro
            35                  40                  45

Ser His Ala Phe Ser Asn Leu Pro Asn Ile Ser Arg Ile Tyr Val Ser
        50                  55                  60

Ile Asp Val Thr Leu Gln Gln Leu Glu Ser His Ser Phe Tyr Asn Leu
65                  70                  75                  80

Ser Lys Val Thr His Ile Glu Ile Arg Asn Thr Arg Asn Leu Thr Tyr

```
            85                  90                  95
Ile Asp Pro Asp Ala Leu Lys Glu Leu Pro Leu Leu Lys Phe Leu Gly
            100                 105                 110

Ile Phe Asn Thr Gly Leu Lys Met Pro Asp Leu Thr Lys Val Tyr Ser
            115                 120                 125

Thr Asp Ile Phe Phe Ile Leu Glu Ile Thr Asp Asn Pro Tyr Met Thr
            130                 135                 140

Ser Ile Pro Val Asn Ala Phe Gln Gly Leu Cys Asn Glu Thr Leu Thr
145                 150                 155                 160

Leu Lys Leu Tyr Asn Asn Gly Phe Thr Ser Val Gln Gly Tyr Ala Phe
                165                 170                 175

Asn Gly Thr Lys Leu Asp Ala Val Tyr Leu Asn Lys Asn Lys Tyr Leu
                180                 185                 190

Thr Val Ile Asp Lys Asp Ala Phe Gly Gly Val Tyr Ser Gly Pro Ser
            195                 200                 205

Leu Leu Asp Val Ser Gln Thr Ser Val Thr Ala Leu Pro Ser Lys Gly
            210                 215                 220

Leu Glu His Leu Ala Glu Leu Ile Ala Arg Asn Thr Trp Thr Leu Lys
225                 230                 235                 240

Lys Leu Pro Leu Ser Leu Ser Phe Leu His Leu Thr Arg Ala Asp Leu
                245                 250                 255

Ser Tyr Pro Ser His
                260

<210> SEQ ID NO 16
<211> LENGTH: 261
<212> TYPE: PRT
<213> ORGANISM: Artificial Sequence
<220> FEATURE:
<223> OTHER INFORMATION: Synthetic Construct

<400> SEQUENCE: 16

Gly Met Gly Cys Ser Ser Pro Pro Cys Glu Cys His Gln Glu Glu Asp
1               5                   10                  15

Phe Arg Val Thr Cys Lys Ala Ile Gln Arg Ile Pro Ser Leu Pro Pro
            20                  25                  30

Ser Thr Gln Thr Leu Lys Leu Ile Ala Thr His Leu Arg Thr Ile Pro
        35                  40                  45

Ser His Ala Phe Ser Asn Leu Pro Asn Ile Ser Arg Ile Tyr Val Ser
    50                  55                  60

Ile Asp Val Thr Leu Gln Gln Leu Glu Ser His Ser Phe Tyr Asn Leu
65                  70                  75                  80

Ser Lys Val Thr His Ile Glu Ile Arg Asn Thr Arg Asn Leu Thr Tyr
                85                  90                  95

Ile Asp Pro Asp Ala Leu Lys Glu Leu Pro Leu Leu Lys Phe Leu Gly
            100                 105                 110

Ile Phe Asn Thr Gly Leu Lys Met Pro Asp Leu Thr Lys Val Tyr Ser
            115                 120                 125

Thr Asp Ile Phe Phe Ile Leu Glu Ile Thr Asp Asn Pro Tyr Met Thr
            130                 135                 140

Ser Ile Pro Val Asn Ala Phe Gln Gly Leu Cys Asn Glu Thr Leu Thr
145                 150                 155                 160

Leu Lys Leu Tyr Asn Asn Gly Phe Thr Ser Val Gln Gly Tyr Ala Phe
                165                 170                 175

Asn Gly Thr Lys Leu Asp Ala Val Tyr Leu Asn Lys Asn Lys Tyr Leu
```

```
            180                 185                 190
Thr Val Ile Asp Lys Asp Ala Phe Gly Gly Val Tyr Ser Gly Pro Ser
            195                 200                 205
Leu Leu Asp Val Ser Gln Thr Ser Val Thr Ala Leu Pro Ser Lys Gly
            210                 215                 220
Leu Glu His Leu Ala Glu Leu Ile Ala Arg Asn Thr Trp Thr Leu Lys
225                 230                 235                 240
Lys Leu Pro Leu Ser Leu Ser Phe Leu His Leu Thr Arg Ala Asp Leu
                245                 250                 255
Ser Tyr Pro Ser His
                260

<210> SEQ ID NO 17
<211> LENGTH: 22
<212> TYPE: PRT
<213> ORGANISM: Artificial Sequence
<220> FEATURE:
<223> OTHER INFORMATION: Synthetic Construct

<400> SEQUENCE: 17

Ala Glu Ala Ala Ala Lys Glu Ala Ala Ala Lys Glu Ala Ala Ala Lys
1               5                   10                  15

Glu Ala Ala Ala Lys Ala
            20

<210> SEQ ID NO 18
<211> LENGTH: 32
<212> TYPE: PRT
<213> ORGANISM: Artificial Sequence
<220> FEATURE:
<223> OTHER INFORMATION: Synthetic Construct

<400> SEQUENCE: 18

Lys Ala Arg Ala Ala Glu Ala Ala Arg Ala Ala Glu Ala Ala Lys Ala
1               5                   10                  15

Ala Glu Ala Thr Lys Ala Ala Glu Ala Ala Lys Ala Ala Lys Ala
            20                  25                  30

<210> SEQ ID NO 19
<211> LENGTH: 22
<212> TYPE: PRT
<213> ORGANISM: Artificial Sequence
<220> FEATURE:
<223> OTHER INFORMATION: Synthetic Construct

<400> SEQUENCE: 19

Ala Glu Ala Ala Lys Ala Ala Glu Ala Thr Lys Ala Ala Glu Ala Ala
1               5                   10                  15

Ala Lys Ala Ala Lys Ala
            20

<210> SEQ ID NO 20
<211> LENGTH: 15
<212> TYPE: PRT
<213> ORGANISM: Artificial Sequence
<220> FEATURE:
<223> OTHER INFORMATION: Synthetic Construct

<400> SEQUENCE: 20

Gly Gly Gly Gly Ser Gly Gly Gly Gly Ser Gly Gly Gly Gly Ser
1               5                   10                  15
```

```
<210> SEQ ID NO 21
<211> LENGTH: 8
<212> TYPE: PRT
<213> ORGANISM: Artificial Sequence
<220> FEATURE:
<223> OTHER INFORMATION: Synthetic Construct

<400> SEQUENCE: 21

Gly Gly Gly Gly Gly Gly Gly Gly
1               5

<210> SEQ ID NO 22
<211> LENGTH: 229
<212> TYPE: PRT
<213> ORGANISM: Artificial Sequence
<220> FEATURE:
<223> OTHER INFORMATION: Synthetic Construct

<400> SEQUENCE: 22

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225

<210> SEQ ID NO 23
<211> LENGTH: 24
<212> TYPE: PRT
<213> ORGANISM: Artificial Sequence
<220> FEATURE:
<223> OTHER INFORMATION: Synthetic Construct

<400> SEQUENCE: 23

Tyr Arg Glu Asn Val Phe Lys Leu Leu Pro Gln Leu Thr Tyr Leu Asp
1               5                   10                  15
```

Gly Tyr Asp Arg Asp Asp Lys Glu
            20

<210> SEQ ID NO 24
<211> LENGTH: 24
<212> TYPE: PRT
<213> ORGANISM: Artificial Sequence
<220> FEATURE:
<223> OTHER INFORMATION: Synthetic Construct

<400> SEQUENCE: 24

Asp Arg Glu Asn Val Phe Lys Leu Leu Pro Gln Leu Thr Tyr Leu Tyr
1               5                   10                  15

Gly Tyr Asp Arg Asp Asp Lys Glu
            20

<210> SEQ ID NO 25
<211> LENGTH: 24
<212> TYPE: PRT
<213> ORGANISM: Artificial Sequence
<220> FEATURE:
<223> OTHER INFORMATION: Synthetic Construct

<400> SEQUENCE: 25

Tyr Arg Glu Asn Ser Phe Lys Leu Leu Pro Gln Leu Thr Tyr Leu Asp
1               5                   10                  15

Gly Tyr Asp Arg Asp Asp Lys Glu
            20

<210> SEQ ID NO 26
<211> LENGTH: 24
<212> TYPE: PRT
<213> ORGANISM: Artificial Sequence
<220> FEATURE:
<223> OTHER INFORMATION: Synthetic Construct

<400> SEQUENCE: 26

Tyr Arg Glu Ser Val Phe Lys Leu Leu Pro Gln Leu Thr Tyr Leu Asp
1               5                   10                  15

Gly Tyr Asp Arg Asp Asp Lys Glu
            20

<210> SEQ ID NO 27
<211> LENGTH: 24
<212> TYPE: PRT
<213> ORGANISM: Artificial Sequence
<220> FEATURE:
<223> OTHER INFORMATION: Synthetic Construct

<400> SEQUENCE: 27

Tyr Arg Glu Asn Ser Phe Lys Leu Leu Pro Gln Leu Thr Tyr Leu Glu
1               5                   10                  15

Gly Tyr Asp Arg Asp Asp Lys Glu
            20

<210> SEQ ID NO 28
<211> LENGTH: 24
<212> TYPE: PRT
<213> ORGANISM: Artificial Sequence
<220> FEATURE:
<223> OTHER INFORMATION: Synthetic Construct

<400> SEQUENCE: 28

Tyr Arg Glu Ser Val Phe Lys Leu Leu Pro Gln Leu Thr Tyr Leu Glu

```
                1               5                   10                  15
Gly Tyr Asp Arg Asp Lys Glu
                20
```

<210> SEQ ID NO 29
<211> LENGTH: 506
<212> TYPE: PRT
<213> ORGANISM: Artificial Sequence
<220> FEATURE:
<223> OTHER INFORMATION: Synthetic Construct

<400> SEQUENCE: 29

```
Gly Met Gly Cys Ser Ser Pro Pro Cys Glu Cys His Gln Glu Asp
1               5                   10                  15

Phe Arg Val Thr Cys Lys Asp Ile Gln Arg Ile Pro Ser Leu Pro Pro
                20                  25                  30

Ser Thr Gln Thr Leu Lys Leu Ile Glu Thr His Leu Arg Thr Ile Pro
                35                  40                  45

Ser His Ala Phe Ser Asn Leu Pro Asn Ile Ser Arg Ile Tyr Val Ser
            50                  55                  60

Ile Asp Val Thr Leu Gln Gln Leu Glu Ser His Ser Phe Tyr Asn Leu
65                  70                  75                  80

Ser Lys Val Thr His Ile Glu Ile Arg Asn Thr Arg Asn Leu Thr Tyr
                        85                  90                  95

Ile Asp Pro Asp Ala Leu Lys Glu Leu Pro Leu Leu Lys Phe Leu Gly
                100                 105                 110

Ile Phe Asn Thr Gly Leu Lys Met Phe Pro Asp Leu Thr Lys Val Tyr
                115                 120                 125

Ser Thr Asp Ile Phe Phe Ile Leu Glu Ile Thr Asp Asn Pro Tyr Met
            130                 135                 140

Thr Ser Ile Pro Val Asn Ala Phe Gln Gly Leu Cys Asn Glu Thr Leu
145                 150                 155                 160

Thr Leu Lys Leu Tyr Asn Asn Gly Phe Thr Ser Val Gln Gly Tyr Ala
                165                 170                 175

Phe Asn Gly Thr Lys Leu Asp Ala Val Tyr Leu Asn Lys Asn Lys Tyr
                180                 185                 190

Leu Thr Val Ile Asp Lys Asp Ala Phe Gly Gly Val Tyr Ser Gly Pro
                195                 200                 205

Ser Leu Leu Asp Val Ser Gln Thr Ser Val Thr Ala Leu Pro Ser Lys
            210                 215                 220

Gly Leu Glu His Leu Lys Glu Leu Ile Ala Arg Asn Thr Trp Thr Leu
225                 230                 235                 240

Lys Lys Leu Pro Leu Ser Leu Ser Phe Leu His Leu Thr Arg Ala Asp
                245                 250                 255

Leu Ser Tyr Pro Ser His Gly Gly Gly Ser Gly Gly Gly Ser
                260                 265                 270

Gly Gly Gly Gly Ser Glu Ser Lys Tyr Gly Pro Pro Cys Pro Pro Cys
            275                 280                 285

Pro Ala Pro Glu Phe Leu Gly Gly Pro Ser Val Phe Leu Phe Pro Pro
            290                 295                 300

Lys Pro Lys Asp Thr Leu Met Ile Ser Arg Thr Pro Glu Val Thr Cys
305                 310                 315                 320

Val Val Val Asp Val Ser Gln Glu Asp Pro Glu Val Gln Phe Asn Trp
                        325                 330                 335

Tyr Val Asp Gly Val Glu Val His Asn Ala Lys Thr Lys Pro Arg Glu
```

```
            340                 345                 350
Glu Gln Phe Asn Ser Thr Tyr Arg Val Val Ser Val Leu Thr Val Leu
            355                 360                 365

His Gln Asp Trp Leu Asn Gly Lys Glu Tyr Lys Cys Lys Val Ser Asn
    370                 375                 380

Lys Gly Leu Pro Ser Ser Ile Glu Lys Thr Ile Ser Lys Ala Lys Gly
385                 390                 395                 400

Gln Pro Arg Glu Pro Gln Val Tyr Thr Leu Pro Pro Ser Gln Glu Glu
                405                 410                 415

Met Thr Lys Asn Gln Val Ser Leu Thr Cys Leu Val Lys Gly Phe Tyr
            420                 425                 430

Pro Ser Asp Ile Ala Val Glu Trp Glu Ser Asn Gly Gln Pro Glu Asn
                435                 440                 445

Asn Tyr Lys Thr Thr Pro Pro Val Leu Asp Ser Asp Gly Ser Phe Phe
        450                 455                 460

Leu Tyr Ser Arg Leu Thr Val Asp Lys Ser Arg Trp Gln Glu Gly Asn
465                 470                 475                 480

Val Phe Ser Cys Ser Val Met His Glu Ala Leu His Asn His Tyr Thr
                485                 490                 495

Gln Lys Ser Leu Ser Leu Ser Leu Gly Lys
            500                 505

<210> SEQ ID NO 30
<211> LENGTH: 286
<212> TYPE: PRT
<213> ORGANISM: Artificial Sequence
<220> FEATURE:
<223> OTHER INFORMATION: Synthetic Construct

<400> SEQUENCE: 30

Gly Met Gly Cys Ser Ser Pro Pro Cys Glu Cys His Gln Glu Glu Asp
1               5                   10                  15

Phe Arg Val Thr Cys Lys Asp Ile Gln Arg Ile Pro Ser Leu Pro Pro
                20                  25                  30

Ser Thr Gln Thr Leu Lys Leu Ile Glu Thr His Leu Arg Thr Ile Pro
            35                  40                  45

Ser His Ala Phe Ser Asn Leu Pro Asn Ile Ser Arg Ile Tyr Val Ser
        50                  55                  60

Ile Asp Val Thr Leu Gln Gln Leu Glu Ser His Ser Phe Tyr Asn Leu
65                  70                  75                  80

Ser Lys Val Thr His Ile Glu Ile Arg Asn Thr Arg Asn Leu Thr Tyr
                85                  90                  95

Ile Asp Pro Asp Ala Leu Lys Glu Leu Pro Leu Leu Lys Phe Leu Gly
            100                 105                 110

Ile Phe Asn Thr Gly Leu Lys Met Phe Pro Asp Leu Thr Lys Val Tyr
        115                 120                 125

Ser Thr Asp Ile Phe Phe Ile Leu Glu Ile Thr Asp Asn Pro Tyr Met
    130                 135                 140

Thr Ser Ile Pro Val Asn Ala Phe Gln Gly Leu Cys Asn Glu Thr Leu
145                 150                 155                 160

Thr Leu Lys Leu Tyr Asn Asn Gly Phe Thr Ser Val Gln Gly Tyr Ala
                165                 170                 175

Phe Asn Gly Thr Lys Leu Asp Ala Val Tyr Leu Asn Lys Asn Lys Tyr
            180                 185                 190

Leu Thr Val Ile Asp Lys Asp Ala Phe Gly Gly Val Tyr Ser Gly Pro
```

```
            195                 200                 205
Ser Leu Leu Asp Val Ser Gln Thr Ser Val Thr Ala Leu Pro Ser Lys
    210                 215                 220

Gly Leu Glu His Leu Lys Glu Leu Ile Ala Arg Asn Thr Trp Thr Leu
225                 230                 235                 240

Lys Lys Leu Pro Leu Ser Tyr Arg Glu Asn Ser Phe Lys Leu Leu Pro
                245                 250                 255

Gln Leu Thr Tyr Leu Asp Gly Tyr Asp Arg Asp Asp Lys Glu Gly Gly
            260                 265                 270

Gly Ser Gly Gly Gly Ser His His His His His His His
            275                 280                 285

<210> SEQ ID NO 31
<211> LENGTH: 512
<212> TYPE: PRT
<213> ORGANISM: Artificial Sequence
<220> FEATURE:
<223> OTHER INFORMATION: Synthetic Construct

<400> SEQUENCE: 31

Gly Met Gly Cys Ser Ser Pro Pro Cys Glu Cys His Gln Glu Glu Asp
1               5                   10                  15

Phe Arg Val Thr Cys Lys Asp Ile Gln Arg Ile Pro Ser Leu Pro Pro
            20                  25                  30

Ser Thr Gln Thr Leu Lys Leu Ile Glu Thr His Leu Arg Thr Ile Pro
        35                  40                  45

Ser His Ala Phe Ser Asn Leu Pro Asn Ile Ser Arg Ile Tyr Val Ser
    50                  55                  60

Ile Asp Val Thr Leu Gln Gln Leu Glu Ser His Ser Phe Tyr Asn Leu
65                  70                  75                  80

Ser Lys Val Thr His Ile Glu Ile Arg Asn Thr Arg Asn Leu Thr Tyr
                85                  90                  95

Ile Asp Pro Asp Ala Leu Lys Glu Leu Pro Leu Leu Lys Phe Leu Gly
            100                 105                 110

Ile Phe Asn Thr Gly Leu Lys Met Pro Asp Leu Thr Lys Val Tyr Ser
        115                 120                 125

Thr Asp Ile Phe Phe Ile Leu Glu Ile Thr Asp Asn Pro Tyr Met Thr
130                 135                 140

Ser Ile Pro Val Asn Ala Phe Gln Gly Leu Cys Asn Glu Thr Leu Thr
145                 150                 155                 160

Leu Lys Leu Tyr Asn Asn Gly Phe Thr Ser Val Gln Gly Tyr Ala Phe
                165                 170                 175

Asn Gly Thr Lys Leu Asp Ala Val Tyr Leu Asn Lys Asn Lys Tyr Leu
            180                 185                 190

Thr Val Ile Asp Lys Asp Ala Phe Gly Gly Val Tyr Ser Gly Pro Ser
        195                 200                 205

Leu Leu Asp Val Ser Gln Thr Ser Val Thr Ala Leu Pro Ser Lys Gly
    210                 215                 220

Leu Glu His Leu Lys Glu Leu Ile Ala Arg Asn Thr Trp Thr Leu Lys
225                 230                 235                 240

Lys Leu Pro Leu Ser Leu Ser Phe Leu His Leu Thr Arg Ala Asp Leu
                245                 250                 255

Ser Tyr Pro Ser His Ala Glu Ala Ala Lys Glu Ala Ala Ala Lys
            260                 265                 270

Glu Ala Ala Ala Lys Glu Ala Ala Ala Lys Ala Glu Ser Lys Tyr Gly
```

275                 280                 285
Pro Pro Cys Pro Pro Cys Pro Ala Pro Glu Phe Leu Gly Gly Pro Ser
            290                 295                 300

Val Phe Leu Phe Pro Pro Lys Pro Lys Asp Thr Leu Met Ile Ser Arg
305                 310                 315                 320

Thr Pro Glu Val Thr Cys Val Val Val Asp Val Ser Gln Glu Asp Pro
                325                 330                 335

Glu Val Gln Phe Asn Trp Tyr Val Asp Gly Val Glu Val His Asn Ala
            340                 345                 350

Lys Thr Lys Pro Arg Glu Glu Gln Phe Asn Ser Thr Tyr Arg Val Val
            355                 360                 365

Ser Val Leu Thr Val Leu His Gln Asp Trp Leu Asn Gly Lys Glu Tyr
        370                 375                 380

Lys Cys Lys Val Ser Asn Lys Gly Leu Pro Ser Ser Ile Glu Lys Thr
385                 390                 395                 400

Ile Ser Lys Ala Lys Gly Gln Pro Arg Glu Pro Gln Val Tyr Thr Leu
                405                 410                 415

Pro Pro Ser Gln Glu Glu Met Thr Lys Asn Gln Val Ser Leu Thr Cys
            420                 425                 430

Leu Val Lys Gly Phe Tyr Pro Ser Asp Ile Ala Val Glu Trp Glu Ser
        435                 440                 445

Asn Gly Gln Pro Glu Asn Asn Tyr Lys Thr Thr Pro Pro Val Leu Asp
    450                 455                 460

Ser Asp Gly Ser Phe Phe Leu Tyr Ser Arg Leu Thr Val Asp Lys Ser
465                 470                 475                 480

Arg Trp Gln Glu Gly Asn Val Phe Ser Cys Ser Val Met His Glu Ala
                485                 490                 495

Leu His Asn His Tyr Thr Gln Lys Ser Leu Ser Leu Ser Leu Gly Lys
            500                 505                 510

<210> SEQ ID NO 32
<211> LENGTH: 522
<212> TYPE: PRT
<213> ORGANISM: Artificial Sequence
<220> FEATURE:
<223> OTHER INFORMATION: Synthetic Construct

<400> SEQUENCE: 32

Gly Met Gly Cys Ser Ser Pro Pro Cys Glu Cys His Gln Glu Glu Asp
1               5                   10                  15

Phe Arg Val Thr Cys Lys Asp Ile Gln Arg Ile Pro Ser Leu Pro Pro
                20                  25                  30

Ser Thr Gln Thr Leu Lys Leu Ile Glu Thr His Leu Arg Thr Ile Pro
            35                  40                  45

Ser His Ala Phe Ser Asn Leu Pro Asn Ile Ser Arg Ile Tyr Val Ser
        50                  55                  60

Ile Asp Val Thr Leu Gln Gln Leu Glu Ser His Ser Phe Tyr Asn Leu
65                  70                  75                  80

Ser Lys Val Thr His Ile Glu Ile Arg Asn Thr Arg Asn Leu Thr Tyr
                85                  90                  95

Ile Asp Pro Asp Ala Leu Lys Glu Leu Pro Leu Leu Lys Phe Leu Gly
                100                 105                 110

Ile Phe Asn Thr Gly Leu Lys Met Pro Asp Leu Thr Lys Val Tyr Ser
            115                 120                 125

Thr Asp Ile Phe Phe Ile Leu Glu Ile Thr Asp Asn Pro Tyr Met Thr

```
            130                 135                 140
Ser Ile Pro Val Asn Ala Phe Gln Gly Leu Cys Asn Glu Thr Leu Thr
145                 150                 155                 160

Leu Lys Leu Tyr Asn Asn Gly Phe Thr Ser Val Gln Gly Tyr Ala Phe
                165                 170                 175

Asn Gly Thr Lys Leu Asp Ala Val Tyr Leu Asn Lys Asn Lys Tyr Leu
            180                 185                 190

Thr Val Ile Asp Lys Asp Ala Phe Gly Gly Val Tyr Ser Gly Pro Ser
        195                 200                 205

Leu Leu Asp Val Ser Gln Thr Ser Val Thr Ala Leu Pro Ser Lys Gly
    210                 215                 220

Leu Glu His Leu Lys Glu Leu Ile Ala Arg Asn Thr Trp Thr Leu Lys
225                 230                 235                 240

Lys Leu Pro Leu Ser Leu Ser Phe Leu His Leu Thr Arg Ala Asp Leu
                245                 250                 255

Ser Tyr Pro Ser His Lys Ala Arg Ala Ala Glu Ala Ala Arg Ala Ala
            260                 265                 270

Glu Ala Ala Lys Ala Ala Glu Ala Thr Lys Ala Ala Glu Ala Ala Ala
        275                 280                 285

Lys Ala Ala Lys Ala Glu Ser Lys Tyr Gly Pro Pro Cys Pro Pro Cys
    290                 295                 300

Pro Ala Pro Glu Phe Leu Gly Gly Pro Ser Val Phe Leu Phe Pro Pro
305                 310                 315                 320

Lys Pro Lys Asp Thr Leu Met Ile Ser Arg Thr Pro Glu Val Thr Cys
                325                 330                 335

Val Val Val Asp Val Ser Gln Glu Asp Pro Glu Val Gln Phe Asn Trp
            340                 345                 350

Tyr Val Asp Gly Val Glu Val His Asn Ala Lys Thr Lys Pro Arg Glu
        355                 360                 365

Glu Gln Phe Asn Ser Thr Tyr Arg Val Val Ser Val Leu Thr Val Leu
    370                 375                 380

His Gln Asp Trp Leu Asn Gly Lys Glu Tyr Lys Cys Lys Val Ser Asn
385                 390                 395                 400

Lys Gly Leu Pro Ser Ser Ile Glu Lys Thr Ile Ser Lys Ala Lys Gly
                405                 410                 415

Gln Pro Arg Glu Pro Gln Val Tyr Thr Leu Pro Pro Ser Gln Glu Glu
            420                 425                 430

Met Thr Lys Asn Gln Val Ser Leu Thr Cys Leu Val Lys Gly Phe Tyr
        435                 440                 445

Pro Ser Asp Ile Ala Val Glu Trp Glu Ser Asn Gly Gln Pro Glu Asn
    450                 455                 460

Asn Tyr Lys Thr Thr Pro Pro Val Leu Asp Ser Asp Gly Ser Phe Phe
465                 470                 475                 480

Leu Tyr Ser Arg Leu Thr Val Asp Lys Ser Arg Trp Gln Glu Gly Asn
                485                 490                 495

Val Phe Ser Cys Ser Val Met His Glu Ala Leu His Asn His Tyr Thr
            500                 505                 510

Gln Lys Ser Leu Ser Leu Ser Leu Gly Lys
        515                 520

<210> SEQ ID NO 33
<211> LENGTH: 512
<212> TYPE: PRT
<213> ORGANISM: Artificial Sequence
```

<220> FEATURE:
<223> OTHER INFORMATION: Synthetic Construct

<400> SEQUENCE: 33

```
Gly Met Gly Cys Ser Ser Pro Pro Cys Glu Cys His Gln Glu Glu Asp
1               5                   10                  15

Phe Arg Val Thr Cys Lys Asp Ile Gln Arg Ile Pro Ser Leu Pro Pro
            20                  25                  30

Ser Thr Gln Thr Leu Lys Leu Ile Glu Thr His Leu Arg Thr Ile Pro
        35                  40                  45

Ser His Ala Phe Ser Asn Leu Pro Asn Ile Ser Arg Ile Tyr Val Ser
    50                  55                  60

Ile Asp Val Thr Leu Gln Gln Leu Glu Ser His Ser Phe Tyr Asn Leu
65                  70                  75                  80

Ser Lys Val Thr His Ile Glu Ile Arg Asn Thr Arg Asn Leu Thr Tyr
                85                  90                  95

Ile Asp Pro Asp Ala Leu Lys Glu Leu Pro Leu Leu Lys Phe Leu Gly
            100                 105                 110

Ile Phe Asn Thr Gly Leu Lys Met Pro Asp Leu Thr Lys Val Tyr Ser
        115                 120                 125

Thr Asp Ile Phe Phe Ile Leu Glu Ile Thr Asp Asn Pro Tyr Met Thr
    130                 135                 140

Ser Ile Pro Val Asn Ala Phe Gln Gly Leu Cys Asn Glu Thr Leu Thr
145                 150                 155                 160

Leu Lys Leu Tyr Asn Asn Gly Phe Thr Ser Val Gln Gly Tyr Ala Phe
                165                 170                 175

Asn Gly Thr Lys Leu Asp Ala Val Tyr Leu Asn Lys Asn Lys Tyr Leu
            180                 185                 190

Thr Val Ile Asp Lys Asp Ala Phe Gly Gly Val Tyr Ser Gly Pro Ser
        195                 200                 205

Leu Leu Asp Val Ser Gln Thr Ser Val Thr Ala Leu Pro Ser Lys Gly
210                 215                 220

Leu Glu His Leu Lys Glu Leu Ile Ala Arg Asn Thr Trp Thr Leu Lys
225                 230                 235                 240

Lys Leu Pro Leu Ser Leu Ser Phe Leu His Leu Thr Arg Ala Asp Leu
                245                 250                 255

Ser Tyr Pro Ser His Ala Glu Ala Ala Lys Ala Ala Glu Ala Thr Lys
            260                 265                 270

Ala Ala Glu Ala Ala Lys Ala Ala Lys Ala Glu Ser Lys Tyr Gly
        275                 280                 285

Pro Pro Cys Pro Pro Cys Pro Ala Pro Glu Phe Leu Gly Gly Pro Ser
    290                 295                 300

Val Phe Leu Phe Pro Pro Lys Pro Lys Asp Thr Leu Met Ile Ser Arg
305                 310                 315                 320

Thr Pro Glu Val Thr Cys Val Val Val Asp Val Ser Gln Glu Asp Pro
                325                 330                 335

Glu Val Gln Phe Asn Trp Tyr Val Asp Gly Val Glu Val His Asn Ala
            340                 345                 350

Lys Thr Lys Pro Arg Glu Glu Gln Phe Asn Ser Thr Tyr Arg Val Val
        355                 360                 365

Ser Val Leu Thr Val Leu His Gln Asp Trp Leu Asn Gly Lys Glu Tyr
    370                 375                 380

Lys Cys Lys Val Ser Asn Lys Gly Leu Pro Ser Ser Ile Glu Lys Thr
385                 390                 395                 400
```

```
Ile Ser Lys Ala Lys Gly Gln Pro Arg Glu Pro Gln Val Tyr Thr Leu
                405                 410                 415

Pro Pro Ser Gln Glu Glu Met Thr Lys Asn Gln Val Ser Leu Thr Cys
            420                 425                 430

Leu Val Lys Gly Phe Tyr Pro Ser Asp Ile Ala Val Glu Trp Glu Ser
        435                 440                 445

Asn Gly Gln Pro Glu Asn Asn Tyr Lys Thr Thr Pro Pro Val Leu Asp
    450                 455                 460

Ser Asp Gly Ser Phe Phe Leu Tyr Ser Arg Leu Thr Val Asp Lys Ser
465                 470                 475                 480

Arg Trp Gln Glu Gly Asn Val Phe Ser Cys Ser Val Met His Glu Ala
                485                 490                 495

Leu His Asn His Tyr Thr Gln Lys Ser Leu Ser Leu Ser Leu Gly Lys
            500                 505                 510

<210> SEQ ID NO 34
<211> LENGTH: 498
<212> TYPE: PRT
<213> ORGANISM: Artificial Sequence
<220> FEATURE:
<223> OTHER INFORMATION: Synthetic Construct

<400> SEQUENCE: 34

Gly Met Gly Cys Ser Ser Pro Pro Cys Glu Cys His Gln Glu Glu Asp
1               5                   10                  15

Phe Arg Val Thr Cys Lys Asp Ile Gln Arg Ile Pro Ser Leu Pro Pro
            20                  25                  30

Ser Thr Gln Thr Leu Lys Leu Ile Glu Thr His Leu Arg Thr Ile Pro
        35                  40                  45

Ser His Ala Phe Ser Asn Leu Pro Asn Ile Ser Arg Ile Tyr Val Ser
    50                  55                  60

Ile Asp Val Thr Leu Gln Gln Leu Glu Ser His Ser Phe Tyr Asn Leu
65                  70                  75                  80

Ser Lys Val Thr His Ile Glu Ile Arg Asn Thr Arg Asn Leu Thr Tyr
                85                  90                  95

Ile Asp Pro Asp Ala Leu Lys Glu Leu Pro Leu Leu Lys Phe Leu Gly
            100                 105                 110

Ile Phe Asn Thr Gly Leu Lys Met Pro Asp Leu Thr Lys Val Tyr Ser
        115                 120                 125

Thr Asp Ile Phe Phe Ile Leu Glu Ile Thr Asp Asn Pro Tyr Met Thr
130                 135                 140

Ser Ile Pro Val Asn Ala Phe Gln Gly Leu Cys Asn Glu Thr Leu Thr
145                 150                 155                 160

Leu Lys Leu Tyr Asn Asn Gly Phe Thr Ser Val Gln Gly Tyr Ala Phe
                165                 170                 175

Asn Gly Thr Lys Leu Asp Ala Val Tyr Leu Asn Lys Asn Lys Tyr Leu
            180                 185                 190

Thr Val Ile Asp Lys Asp Ala Phe Gly Gly Val Tyr Ser Gly Pro Ser
        195                 200                 205

Leu Leu Asp Val Ser Gln Thr Ser Val Thr Ala Leu Pro Ser Lys Gly
210                 215                 220

Leu Glu His Leu Lys Glu Leu Ile Ala Arg Asn Thr Trp Thr Leu Lys
225                 230                 235                 240

Lys Leu Pro Leu Ser Leu Ser Phe Leu His Leu Thr Arg Ala Asp Leu
                245                 250                 255
```

Ser Tyr Pro Ser His Gly Gly Gly Gly Gly Gly Gly Glu Ser Lys
             260                 265                 270

Tyr Gly Pro Pro Cys Pro Pro Cys Pro Ala Pro Glu Phe Leu Gly Gly
         275                 280                 285

Pro Ser Val Phe Leu Phe Pro Pro Lys Pro Lys Asp Thr Leu Met Ile
290                 295                 300

Ser Arg Thr Pro Glu Val Thr Cys Val Val Val Asp Val Ser Gln Glu
305                 310                 315                 320

Asp Pro Glu Val Gln Phe Asn Trp Tyr Val Asp Gly Val Glu Val His
             325                 330                 335

Asn Ala Lys Thr Lys Pro Arg Glu Glu Gln Phe Asn Ser Thr Tyr Arg
         340                 345                 350

Val Val Ser Val Leu Thr Val Leu His Gln Asp Trp Leu Asn Gly Lys
     355                 360                 365

Glu Tyr Lys Cys Lys Val Ser Asn Lys Gly Leu Pro Ser Ser Ile Glu
370                 375                 380

Lys Thr Ile Ser Lys Ala Lys Gly Gln Pro Arg Glu Pro Gln Val Tyr
385                 390                 395                 400

Thr Leu Pro Pro Ser Gln Glu Glu Met Thr Lys Asn Gln Val Ser Leu
             405                 410                 415

Thr Cys Leu Val Lys Gly Phe Tyr Pro Ser Asp Ile Ala Val Glu Trp
         420                 425                 430

Glu Ser Asn Gly Gln Pro Glu Asn Asn Tyr Lys Thr Thr Pro Pro Val
     435                 440                 445

Leu Asp Ser Asp Gly Ser Phe Phe Leu Tyr Ser Arg Leu Thr Val Asp
450                 455                 460

Lys Ser Arg Trp Gln Glu Gly Asn Val Phe Ser Cys Ser Val Met His
465                 470                 475                 480

Glu Ala Leu His Asn His Tyr Thr Gln Lys Ser Leu Ser Leu Ser Leu
             485                 490                 495

Gly Lys

<210> SEQ ID NO 35
<211> LENGTH: 270
<212> TYPE: PRT
<213> ORGANISM: Artificial Sequence
<220> FEATURE:
<223> OTHER INFORMATION: Synthetic Construct

<400> SEQUENCE: 35

Gly Met Gly Cys Ser Ser Pro Pro Cys Glu Cys His Gln Glu Glu Asp
1               5                   10                  15

Phe Arg Val Thr Cys Lys Asp Ile Gln Arg Ile Pro Ser Leu Pro Pro
             20                  25                  30

Ser Thr Gln Thr Leu Lys Leu Ile Glu Thr His Leu Arg Thr Ile Pro
         35                  40                  45

Ser His Ala Phe Ser Asn Leu Pro Asn Ile Ser Arg Ile Tyr Val Ser
     50                  55                  60

Ile Asp Val Thr Leu Gln Gln Leu Glu Ser His Ser Phe Tyr Asn Leu
65                  70                  75                  80

Ser Lys Val Thr His Ile Glu Ile Arg Asn Thr Arg Asn Leu Thr Tyr
                 85                  90                  95

Ile Asp Pro Asp Ala Leu Lys Glu Leu Pro Leu Leu Lys Phe Leu Gly
             100                 105                 110

```
Ile Phe Asn Thr Gly Leu Lys Met Phe Pro Asp Leu Thr Lys Val Tyr
            115                 120                 125

Ser Thr Asp Ile Phe Phe Ile Leu Glu Ile Thr Asp Asn Pro Tyr Met
        130                 135                 140

Thr Ser Ile Pro Val Asn Ala Phe Gln Gly Leu Cys Asn Glu Thr Leu
145                 150                 155                 160

Thr Leu Lys Leu Tyr Asn Asn Gly Phe Thr Ser Val Gln Gly Tyr Ala
                165                 170                 175

Phe Asn Gly Thr Lys Leu Asp Ala Val Tyr Leu Asn Lys Asn Lys Tyr
            180                 185                 190

Leu Thr Val Ile Asp Lys Asp Ala Phe Gly Gly Val Tyr Ser Gly Pro
        195                 200                 205

Ser Leu Leu Asp Val Ser Gln Thr Ser Val Thr Ala Leu Pro Ser Lys
210                 215                 220

Gly Leu Glu His Leu Lys Glu Leu Ile Ala Arg Asn Thr Trp Thr Leu
225                 230                 235                 240

Lys Lys Leu Pro Leu Ser Tyr Arg Glu Asn Val Phe Lys Leu Leu Pro
                245                 250                 255

Gln Leu Thr Tyr Leu Asp Gly Tyr Asp Arg Asp Asp Lys Glu
            260                 265                 270

<210> SEQ ID NO 36
<211> LENGTH: 270
<212> TYPE: PRT
<213> ORGANISM: Artificial Sequence
<220> FEATURE:
<223> OTHER INFORMATION: Synthetic Construct

<400> SEQUENCE: 36

Gly Met Gly Cys Ser Ser Pro Pro Cys Glu Cys His Gln Glu Glu Asp
1               5                   10                  15

Phe Arg Val Thr Cys Lys Asp Ile Gln Arg Ile Pro Ser Leu Pro Pro
            20                  25                  30

Ser Thr Gln Thr Leu Lys Leu Ile Glu Thr His Leu Arg Thr Ile Pro
        35                  40                  45

Ser His Ala Phe Ser Asn Leu Pro Asn Ile Ser Arg Ile Tyr Val Ser
    50                  55                  60

Ile Asp Val Thr Leu Gln Gln Leu Glu Ser His Ser Phe Tyr Asn Leu
65                  70                  75                  80

Ser Lys Val Thr His Ile Glu Ile Arg Asn Thr Arg Asn Leu Thr Tyr
                85                  90                  95

Ile Asp Pro Asp Ala Leu Lys Glu Leu Pro Leu Leu Lys Phe Leu Gly
            100                 105                 110

Ile Phe Asn Thr Gly Leu Lys Met Phe Pro Asp Leu Thr Lys Val Tyr
            115                 120                 125

Ser Thr Asp Ile Phe Phe Ile Leu Glu Ile Thr Asp Asn Pro Tyr Met
        130                 135                 140

Thr Ser Ile Pro Val Asn Ala Phe Gln Gly Leu Cys Asn Glu Thr Leu
145                 150                 155                 160

Thr Leu Lys Leu Tyr Asn Asn Gly Phe Thr Ser Val Gln Gly Tyr Ala
                165                 170                 175

Phe Asn Gly Thr Lys Leu Asp Ala Val Tyr Leu Asn Lys Asn Lys Tyr
            180                 185                 190

Leu Thr Val Ile Asp Lys Asp Ala Phe Gly Gly Val Tyr Ser Gly Pro
        195                 200                 205
```

Ser Leu Leu Asp Val Ser Gln Thr Ser Val Thr Ala Leu Pro Ser Lys
    210                 215                 220

Gly Leu Glu His Leu Lys Glu Leu Ile Ala Arg Asn Thr Trp Thr Leu
225                 230                 235                 240

Lys Lys Leu Pro Leu Ser Asp Arg Glu Asn Val Phe Lys Leu Leu Pro
                245                 250                 255

Gln Leu Thr Tyr Leu Tyr Gly Tyr Asp Arg Asp Asp Lys Glu
        260                 265                 270

<210> SEQ ID NO 37
<211> LENGTH: 270
<212> TYPE: PRT
<213> ORGANISM: Artificial Sequence
<220> FEATURE:
<223> OTHER INFORMATION: Synthetic Construct

<400> SEQUENCE: 37

Gly Met Gly Cys Ser Ser Pro Pro Cys Glu Cys His Gln Glu Glu Asp
1               5                   10                  15

Phe Arg Val Thr Cys Lys Asp Ile Gln Arg Ile Pro Ser Leu Pro Pro
                20                  25                  30

Ser Thr Gln Thr Leu Lys Leu Ile Glu Thr His Leu Arg Thr Ile Pro
            35                  40                  45

Ser His Ala Phe Ser Asn Leu Pro Asn Ile Ser Arg Ile Tyr Val Ser
    50                  55                  60

Ile Asp Val Thr Leu Gln Gln Leu Glu Ser His Ser Phe Tyr Asn Leu
65                  70                  75                  80

Ser Lys Val Thr His Ile Glu Ile Arg Asn Thr Arg Asn Leu Thr Tyr
                85                  90                  95

Ile Asp Pro Asp Ala Leu Lys Glu Leu Pro Leu Leu Lys Phe Leu Gly
            100                 105                 110

Ile Phe Asn Thr Gly Leu Lys Met Phe Pro Asp Leu Thr Lys Val Tyr
        115                 120                 125

Ser Thr Asp Ile Phe Phe Ile Leu Glu Ile Thr Asp Asn Pro Tyr Met
    130                 135                 140

Thr Ser Ile Pro Val Asn Ala Phe Gln Gly Leu Cys Asn Glu Thr Leu
145                 150                 155                 160

Thr Leu Lys Leu Tyr Asn Asn Gly Phe Thr Ser Val Gln Gly Tyr Ala
                165                 170                 175

Phe Asn Gly Thr Lys Leu Asp Ala Val Tyr Leu Asn Lys Asn Lys Tyr
            180                 185                 190

Leu Thr Val Ile Asp Lys Asp Ala Phe Gly Gly Val Tyr Ser Gly Pro
        195                 200                 205

Ser Leu Leu Asp Val Ser Gln Thr Ser Val Thr Ala Leu Pro Ser Lys
    210                 215                 220

Gly Leu Glu His Leu Lys Glu Leu Ile Ala Arg Asn Thr Trp Thr Leu
225                 230                 235                 240

Lys Lys Leu Pro Leu Ser Tyr Arg Glu Asn Ser Phe Lys Leu Leu Pro
                245                 250                 255

Gln Leu Thr Tyr Leu Asp Gly Tyr Asp Arg Asp Asp Lys Glu
        260                 265                 270

<210> SEQ ID NO 38
<211> LENGTH: 270
<212> TYPE: PRT
<213> ORGANISM: Artificial Sequence
<220> FEATURE:

<223> OTHER INFORMATION: Synthetic Construct

<400> SEQUENCE: 38

```
Gly Met Gly Cys Ser Ser Pro Pro Cys Glu Cys His Gln Glu Glu Asp
1               5                   10                  15

Phe Arg Val Thr Cys Lys Asp Ile Gln Arg Ile Pro Ser Leu Pro Pro
            20                  25                  30

Ser Thr Gln Thr Leu Lys Leu Ile Glu Thr His Leu Arg Thr Ile Pro
        35                  40                  45

Ser His Ala Phe Ser Asn Leu Pro Asn Ile Ser Arg Ile Tyr Val Ser
    50                  55                  60

Ile Asp Val Thr Leu Gln Gln Leu Glu Ser His Ser Phe Tyr Asn Leu
65                  70                  75                  80

Ser Lys Val Thr His Ile Glu Ile Arg Asn Thr Arg Asn Leu Thr Tyr
                85                  90                  95

Ile Asp Pro Asp Ala Leu Lys Glu Leu Pro Leu Leu Lys Phe Leu Gly
            100                 105                 110

Ile Phe Asn Thr Gly Leu Lys Met Phe Pro Asp Leu Thr Lys Val Tyr
        115                 120                 125

Ser Thr Asp Ile Phe Phe Ile Leu Glu Ile Thr Asp Asn Pro Tyr Met
    130                 135                 140

Thr Ser Ile Pro Val Asn Ala Phe Gln Gly Leu Cys Asn Glu Thr Leu
145                 150                 155                 160

Thr Leu Lys Leu Tyr Asn Asn Gly Phe Thr Ser Val Gln Gly Tyr Ala
                165                 170                 175

Phe Asn Gly Thr Lys Leu Asp Ala Val Tyr Leu Asn Lys Asn Lys Tyr
            180                 185                 190

Leu Thr Val Ile Asp Lys Asp Ala Phe Gly Gly Val Tyr Ser Gly Pro
        195                 200                 205

Ser Leu Leu Asp Val Ser Gln Thr Ser Val Thr Ala Leu Pro Ser Lys
    210                 215                 220

Gly Leu Glu His Leu Lys Glu Leu Ile Ala Arg Asn Thr Trp Thr Leu
225                 230                 235                 240

Lys Lys Leu Pro Leu Ser Tyr Arg Glu Ser Val Phe Lys Leu Leu Pro
                245                 250                 255

Gln Leu Thr Tyr Leu Asp Gly Tyr Asp Arg Asp Asp Lys Glu
            260                 265                 270
```

<210> SEQ ID NO 39
<211> LENGTH: 270
<212> TYPE: PRT
<213> ORGANISM: Artificial Sequence
<220> FEATURE:
<223> OTHER INFORMATION: Synthetic Construct

<400> SEQUENCE: 39

```
Gly Met Gly Cys Ser Ser Pro Pro Cys Glu Cys His Gln Glu Glu Asp
1               5                   10                  15

Phe Arg Val Thr Cys Lys Asp Ile Gln Arg Ile Pro Ser Leu Pro Pro
            20                  25                  30

Ser Thr Gln Thr Leu Lys Leu Ile Glu Thr His Leu Arg Thr Ile Pro
        35                  40                  45

Ser His Ala Phe Ser Asn Leu Pro Asn Ile Ser Arg Ile Tyr Val Ser
    50                  55                  60

Ile Asp Val Thr Leu Gln Gln Leu Glu Ser His Ser Phe Tyr Asn Leu
65                  70                  75                  80
```

```
Ser Lys Val Thr His Ile Glu Ile Arg Asn Thr Arg Asn Leu Thr Tyr
            85                  90                  95

Ile Asp Pro Asp Ala Leu Lys Glu Leu Pro Leu Leu Lys Phe Leu Gly
            100                 105                 110

Ile Phe Asn Thr Gly Leu Lys Met Phe Pro Asp Leu Thr Lys Val Tyr
        115                 120                 125

Ser Thr Asp Ile Phe Phe Ile Leu Glu Ile Thr Asp Asn Pro Tyr Met
        130                 135                 140

Thr Ser Ile Pro Val Asn Ala Phe Gln Gly Leu Cys Asn Glu Thr Leu
145                 150                 155                 160

Thr Leu Lys Leu Tyr Asn Asn Gly Phe Thr Ser Val Gln Gly Tyr Ala
            165                 170                 175

Phe Asn Gly Thr Lys Leu Asp Ala Val Tyr Leu Asn Lys Asn Lys Tyr
            180                 185                 190

Leu Thr Val Ile Asp Lys Asp Ala Phe Gly Gly Val Tyr Ser Gly Pro
        195                 200                 205

Ser Leu Leu Asp Val Ser Gln Thr Ser Val Thr Ala Leu Pro Ser Lys
        210                 215                 220

Gly Leu Glu His Leu Lys Glu Leu Ile Ala Arg Asn Thr Trp Thr Leu
225                 230                 235                 240

Lys Lys Leu Pro Leu Ser Tyr Arg Glu Ser Val Phe Lys Leu Leu Pro
            245                 250                 255

Gln Leu Thr Tyr Leu Glu Gly Tyr Asp Arg Asp Asp Lys Glu
            260                 265                 270
```

UNITED STATES PATENT AND TRADEMARK OFFICE
CERTIFICATE OF CORRECTION

PATENT NO. : 11,479,596 B2
APPLICATION NO. : 17/256296
DATED : October 25, 2022
INVENTOR(S) : Moo Young Song It is certified that error appears in the above-identified patent and that said Letters Patent is hereby corrected as shown below:

In the Specification

Column 15, Line 20, "racy" should be -- rac5 --.

Column 23, Line 62, "1×PBS" should be -- 1X PBS --.

Signed and Sealed this
Twentieth Day of December, 2022

Katherine Kelly Vidal
*Director of the United States Patent and Trademark Office*